(12) United States Patent
Dias Figueiredo et al.

(10) Patent No.: US 11,905,531 B2
(45) Date of Patent: Feb. 20, 2024

(54) RECOMBINANT AAV VECTORS EXPRESSING OSTEOPROTECTIVE GENES, INCLUDING HAS2 AND LUBRICIN, USEFUL IN THE TREATMENT OF OSTEOARTHRITIS AND RELATED JOINT CONDITIONS IN MAMMALS

(71) Applicants: BOEHRINGER INGELHEIM ANIMAL HEALTH USA INC., Duluth, GA (US); GENZYME CORPORATION, Cambridge, MA (US)

(72) Inventors: Monica Dias Figueiredo, Athens, GA (US); Sirkka R M Kyostio-Moore, Ashland, MA (US); Patricia Berthelette, Uxbridge, MA (US)

(73) Assignees: GENZYME CORPORATION, Cambridge, MA (US); BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

(21) Appl. No.: 16/524,645

(22) Filed: Jul. 29, 2019

(65) Prior Publication Data

US 2020/0231940 A1 Jul. 23, 2020

Related U.S. Application Data

(63) Continuation of application No. 15/405,992, filed on Jan. 13, 2017, now abandoned.

(60) Provisional application No. 62/278,243, filed on Jan. 13, 2016.

(51) Int. Cl.

| | | |
|---|---|---|
| *A61K 48/00* | (2006.01) | |
| *C12N 15/86* | (2006.01) | |
| *C12N 15/63* | (2006.01) | |
| *C07H 21/04* | (2006.01) | |
| *C12N 7/00* | (2006.01) | |
| *A61K 38/45* | (2006.01) | |
| *C07K 14/78* | (2006.01) | |
| *C12N 9/10* | (2006.01) | |
| *A01K 67/00* | (2006.01) | |

(52) U.S. Cl.
CPC ............ *C12N 7/00* (2013.01); *A61K 38/45* (2013.01); *A61K 48/005* (2013.01); *C07K 14/78* (2013.01); *C12N 9/1051* (2013.01); *C12N 15/86* (2013.01); *C12Y 204/01212* (2013.01); *C12N 2750/14111* (2013.01); *C12N 2750/14121* (2013.01); *C12N 2750/14143* (2013.01)

(58) Field of Classification Search
CPC ........ C12N 7/00; C12N 15/86; C12N 9/1051; C12N 2750/14111; C12N 2750/14121; C12N 2750/14143; A61K 48/005; A61K 38/45
See application file for complete search history.

(56) References Cited

U.S. PATENT DOCUMENTS

| | | | |
|---|---|---|---|
| 4,797,368 A | 1/1989 | Carter | |
| 5,328,470 A | 7/1994 | Nabel | |
| 5,658,785 A | 8/1997 | Johnson | |
| 5,693,531 A | 12/1997 | Chiorini | |
| 6,315,992 B1 * | 11/2001 | Noh ..................... | C07K 14/495 514/44 R |
| 6,423,514 B1 | 7/2002 | Briskin | |
| 6,566,118 B1 | 5/2003 | Atkinson | |
| 6,989,264 B2 | 1/2006 | Atkinson | |
| 6,995,006 B2 | 2/2006 | Atkinson | |
| 7,338,655 B1 * | 3/2008 | Noh ..................... | A61K 48/00 424/93.1 |
| 7,618,914 B2 | 11/2009 | Sato | |
| 7,618,941 B2 | 11/2009 | Jay | |
| 7,642,236 B2 | 1/2010 | Flannery | |
| 7,846,428 B2 | 12/2010 | Fisher | |
| 7,893,029 B2 | 2/2011 | Flannery | |
| 7,897,571 B2 | 3/2011 | Flannery | |

(Continued)

FOREIGN PATENT DOCUMENTS

| | | |
|---|---|---|
| EP | 1664315 B1 | 5/2012 |
| EP | 1663291 B1 | 6/2012 |

(Continued)

OTHER PUBLICATIONS

Zhang et al. Amelioration of osteoarthritis by intra-articular hyaluronan synthase-2 gene therapy. Medical Hypotheses 69:1111-1113 , (Year: 2007).*

(Continued)

*Primary Examiner* — Quang Nguyen
(74) *Attorney, Agent, or Firm* — MORRISON & FOERSTER LLP

(57) ABSTRACT

The present disclosure relates to recombinant viral vectors, to pharmaceutical compositions comprising such recombinant vectors, and to methods for prevention and treatment of osteoarthritis in mammals. In particular, this disclosure provides adeno-associated virus (AAV) vectors capable of expressing, in a host, osteoprotective/chondroprotective bioactive proteins, including hyaluronan synthase 2 (HAS2) and lubricin (PRG4). Methods of production of these AAV are provided, as are methods of treatment of osteoarthritis in mammalian joints, by the long-term gene expression of osteoprotective/chondroprotective proteins, including HAS2 and PRG4, in both synovial and chondrocyte cells.

12 Claims, 27 Drawing Sheets

Specification includes a Sequence Listing.

(56) References Cited

U.S. PATENT DOCUMENTS

| | | | |
|---|---|---|---|
| 8,097,599 B2 | 1/2012 | Fischer | |
| 8,298,818 B2* | 10/2012 | Boye et al. | |
| 8,420,793 B2 | 4/2013 | Flannery | |
| 8,529,885 B2* | 9/2013 | Tak | A61P 19/02 |
| | | | 435/320.1 |
| 9,061,059 B2* | 6/2015 | Chakraborty et al. | |
| 9,169,492 B2* | 10/2015 | Monhahan et al. | |
| 2003/0108531 A1 | 6/2003 | Moriya | |
| 2006/0240037 A1 | 10/2006 | Fey | |
| 2008/0139458 A1 | 6/2008 | Jay | |
| 2008/0187576 A1* | 8/2008 | Ghivizzani et al. | |
| 2009/0155200 A1 | 6/2009 | Jay | |
| 2012/0114755 A1 | 5/2012 | Amadio | |
| 2013/0116186 A1 | 5/2013 | Jay | |
| 2013/0196930 A1 | 8/2013 | Flannery | |
| 2015/0031083 A1 | 1/2015 | Lee | |
| 2015/0361452 A1 | 12/2015 | Ruan et al. | |
| 2017/0304466 A1* | 10/2017 | Finn et al. | |

FOREIGN PATENT DOCUMENTS

| | | | | |
|---|---|---|---|---|
| JP | 2003500022 A | 1/2003 | | |
| WO | 2000064930 A2 | 11/2000 | | |
| WO | 2008124724 A1 | 10/2008 | | |
| WO | 2010115841 A1 | 10/2010 | | |
| WO | 2014115022 A1 | 7/2014 | | |
| WO | 2014205237 A2 | 12/2014 | | |
| WO | WO-2015035395 A1 * | 3/2015 | ......... | A61K 48/0075 |

OTHER PUBLICATIONS

Wu et al. Self-Complementary recombinant adeno-associated viral vectors: Packaging capacity and the role of Rep proteins in vector purity. Human Gene Therapy 18:171-182, (Year: 2007).*
McCarty, D. Self-complementary AAV Vectors; Advances and Applications. Molecular Therapy 16: 1648-1656, (Year: 2008).*
Gray et al. Optimizing promoters for recombinant adeno-associated virus-mediated gene expression in the peripheral and central nervous system using self-complementary vectors. Human Gene Therapy 22:1143-1153, (Year: 2011).*
Aalbers et al. Advancements in adeno-associated viral gene therapy approaches: exploring a new horizon. F1000 Medicine Reports 2011, 3:17.
Aalbers, C.J. et al. (2015). "Preclinical Potency And Biodistribution Studies Of An AAV Vector Expressing Human Interferon-B (Artio2) For Local Treatment Of Patients With Rheumatoid Arthritis," PLoS One 10:e130612, 17 pages.
Ai, M. et al. (Feb. 2, 2015). "Anti-Lubricin Monoclonal Antibodies Created Using Lubricin-Knockout Mice Immunodetect Lubricin In Several Species And In Patients With Healthy And Diseased Joints," PloS one 10(2): e0116237, 17 pages.
Apparailly, F. et al. (Apr. 2005). "Adeno-Associated Virus Pseudotype 5 Vector Improves Gene Transfer In Arthritic Joints," Human Gene therapy 16(4):426-434.
Asokan, A. et al. (Apr. 2012, e-pub. Jan. 24, 2012). "The AAV Vector Toolkit: Poised at the Clinical Crossroads," Molecular Therapy 20(4):699-708.
Balazs, E.A. (1974). "The Physical Properties Of Synovial Fluid And The Special Role Of Hyaluronic Acid," Disorders of the Knee 2:61-74.
Beevart L, Aalbers CJ, Vierboom MP, et al. Safety, biodistribution, and efficacy of an AAV-5 vector encoding human Interferon-beta (ART-102) delivered via intra-articular injection in rhesus monkeys with collagen-induced arthritis. Hum Gene Ther Clin Dev 2015;26:103-112.
Bennett et al. The effect of robenacoxib on the concentration of C-reactive protein in synovial fluid from dogs with osteoarthritis. BMC Veterinary Research 2013, 9:42.
Blewis, M.E. et al. (Mar. 6, 2007). "A Model Of Synovial Fluid Lubricant Composition In Normal And Injured Joints," Eur Cell Mater 13(1):26-39.

Boissier MC, Lemeiter D, Clavel C, et al. Synoviocyte infection with adeno-associated virus (AAV) is neutralized by human synovial fluid from arthritis patients and depends on AAV serotype. Hum Gene Ther 2007;18:525-535.
Brooks, P.M. (Sep. 2002). "Impact Of Osteoarthritis On Individuals And Society: How Much Disability? Social Consequences And Health Economic Implications," Current opinion in rheumatology 14(5):573-577.
Calcedo R, Franco J, Qin Q, et al. Preexisting neutralizing antibodies to adeno-associated virus capsids in large animals other than monkeys may confound in vivo gene therapy studies. Hum Gene Ther Methods 2015;26:103-105.
Chen, S-H. et al. (Apr. 1994). "Gene Therapy for Brain Tumors: Regression of Experimental Gliomas by Adenovirus-Mediated Gene Transfer in Vivo," Proc. Natl. Acad. Sci. USA 91:3054-3057.
Davidson, B.L. et al. (Mar. 28, 2000). "Recombinant Adeno-Associated Virus Type 2, 4, and 5 Vectors: Transduction of Variant Cell Types and Regions in the Mammalian Central Nervous System," PNAS 97(7):3428-3432.
David-Raoudi, M. et al. (Mar. 2009). "Chondroitin Sulfate Increases Hyaluronan Production By Human Synoviocytes Through Differential Regulation Of Hyaluronan Synthases: Role Of P38 And Akt," Arthritis & Rheumatism: Official Journal of the American College of Rheumatology 60(3):760-770.
Daya et al. Gene Therapy Using Adena-Associated Virus Vectors. Clinical Microbiology Reviews, Oct. 2008, p. 583-593.
Docampo, M.J. et al. (Dec. 2011). "Increased HAS2-Driven Hyaluronic Acid Synthesis In Shar-Pei Dogs With Hereditary Cutaneous Hyaluronosis (Mucinosis)," Veterinary Dermatology 22(6):535-545.
Drag et al. Efficacy of Firocoxib in Preventing Urate-Induced Synovitis, Pain, and Inflammation in Dogs. Vet. Therapeutics, vol. 8, No. 1, Spring 2007.
Elsaid, K.A. et al. (Jun. 2008). "Decreased Lubricin Concentrations And Markers Of Joint Inflammation In The Synovial Fluid Of Patients With Anterior Cruciate Ligament Injury," Arthritis & Rheumatism: Official Journal of the American College of Rheumatology 58(6):1707-1715.
Evans, C.H. et al. (1994). "Gene Therapy For Arthritis" in Gene Therapeutics: Methods and Applications of Direct Gene Transfer. Birkhauser: Boston, MA, 320-343.
Evans, C.H. et al. (Aug. 2009). "Progress And Prospects: Genetic Treatments For Disorders Of Bones And Joints," Gene Therapy 16(8):944-952.
Evans, C.H. et al. (Feb. 2009, e-pub Jan. 30, 2009). "Gene Therapy Of The Rheumatic Diseases: 1998 to 2008," Arthritis Research & Therapy 11(1):1-12.
Flannery et al. Prevention of Cartilage Degeneration in a Rat Model of Osteoarthritis by Intraarticular Treatment With Recombinant Lubricin. Arthritis & Rheumatism vol. 60, No. 3, Mar. 2009, pp. 840-847.
Flannery, C.R. et al. (Jan. 27, 1999). "Articular Cartilage Superficial Zone Protein (SZP) Is Homologous To Megakaryocyte Stimulating Factor Precursor And Is A Multifunctional Proteoglycan With Potential Growth-Promoting, Cytoprotective, And Lubricating Properties In Cartilage Metabolism," Biochemical And Biophysical Research Communications 254(3):535-541.
Frisbie, D.D. et al. (Jan. 2002). "Treatment Of Experimental Equine Osteoarthritis By In Vivo Delivery Of The Equine Interleukin-1 Receptor Antagonist Gene," Gene Therapy 9(1):12-20.
Gao, G-P., et al. (Sep. 3, 2003). "Novel Adeno-Associated Viruses From Rhesus Monkeys As Vectors For Human Gene Therapy," Proceedings of the National Academy of Sciences 99(18):11854-11859.
Goodrich et al. Optimization of scAAVIL-1 ra In Vitro and In Vivo to Deliver High Levels of Therapeutic Protein for Treatment of Osteoarthritis. Mol. Therapy-Nucleic Acids (2013) 2, e70.
Guo, N. et al. (Apr. 27, 2007). "A Rapid Transient Increase In Hyaluronan Synthase-2 Mrna Initiates Secretion Of Hyaluronan By Corneal Keratocytes In Response To Transforming Growth Factor β," Journal of Biological Chemistry 282(17):12475-12483.

(56) References Cited

OTHER PUBLICATIONS

Hemphill, D.D. et al. (Jul. 29, 2014). "Adeno-Associated Viral Vectors Show Serotype Specific Transduction Of Equine Joint Tissue Explants And Cultured Monolayers," Scientific Reports 4:5861, 7 pages.
Hidaka et al. Acceleration of cartilage repair by genetically modified chondrocytes over expressing bone morphogenetic protein-?. Journal of Orthopaedic Research 21 (2003) 573-583.
Hurlbut, G.D. et al. (Nov. 2010). "Preexisting Immunity And Low Expression In Primates Highlight Translational Challenges For Liver-Directed AAV8-Mediated Gene Therapy," Molecular Therapy 18(11):1983-1994.
Hurtig et al. BMP-7 Gene Therapy for Mitigation of Post-traumatic Osteoarthritis in Sheep. European Cells and Materials vol. 16. Suppl. 4, 2008 (p. 52).
Hurtig et al. BMP-7 Protects against Progression of Cartilage Degeneration after Impact Injury. Journal of Orthopaedic Research May 2009.
Hyc, A. et al. (Oct. 2009). "Pro-And Anti-Inflammatory Cytokines Increase Hyaluronan Production By Rat Synovial Membrane In Vitro," International Journal Of Molecular Medicine 24(4):579-585.
Itano N, Sawai T, Yoshida M, et al. Three isoforms of mammalian hyaluronan synthases have distinct enzymatic properties. J Biol Chem 1999;274:25086-25092.
Jelic et al. Regeneration of Articular Cartilage Chondral Defects by Osteogenic Protein-1 (Bone Morphogenetic Protein-?) in Sheep. Growth Factors. vol. 19, pp. 101-113.
Keiser, N.W. et al. (Nov. 2011). "Unique Characteristics Of AAV1, 2, And 5 Viral Entry, Intracellular Trafficking, And Nuclear Import Define Transduction Efficiency In Hela Cells," Human Gene Therapy 22(11):1433-1444.
Kwiecinski, J.J. et al. (Nov. 2011). "The Effect Of Molecular Weight On Hyaluronan's Cartilage Boundary Lubricating Ability-Alone And In Combination With Proteoglycan 4," Osteoarthritis and Cartilage 19(11):1356-1362.
Kyostio-Moore et al. Local gene delivery of heme oxygenase-1 by adeno-associated virus into osteoarthritic mouse joints exhibiting synovial oxidative stress. Osteoarthritis and Cartilage 21 (2013) 358-367.
Kyostio-Moore, S. et al. (Dec. 2015). "Overexpression Of Cystatin C In Synovium Does Not Reduce Synovitis Or Cartilage Degradation In Established Osteoarthritis," Arthritis Research & Therapy 17(5):1-16.
Lee, H.H. et al. (Apr. 2013). "Persistence, Localization, And External Control Of Transgene Expression After Single Injection Of Adeno-Associated Virus Into Injured Joints." Human Gene Therapy 24(4):457-466.
Li, P. et al. (Nov. 2012). "Hylan GF 20 Maintains Cartilage Integrity And Decreases Osteophyte Formation In Osteoarthritis Through Both Anabolic And Anti-Catabolic Mechanisms," Osteoarthritis and Cartilage 20(11):1336-1346.
Loeser, R.F. (Oct. 2013). "Osteoarthritis Year In Review 2013: Biology," Osteoarthritis and Cartilage 21(10):1436-1442.
Marshall KW, Manolopoulis V, Mancer K, et al. Amelioration of disease severity by intraarticular hylan therapy in bilateral canine osteoarthritis 2000:18:416-425.
Mason JB, Vandenberghe LH, Xiao R, Wilson JM, Richardson DW. Influence of serotype, cell type, tissue composition, and time after inoculation on gene expression in recombinant adeno-associated viral vector-transduced equine joint issues. Am J Vet Res 2012:73:1178-1185.
Mastbergen & Lafeber. Animal Models of Osteoarthritis—Why Choose a Larger Model? Touch Briefings 2009.
Matthews, G.L. et al. (Sep. 1, 2011). "Emerging Drugs For Osteoarthritis," Expert Opinion On Emerging Drugs 16(3):479-491, 17 pages.
Mease, P.J. et al. (Aug. 2009, e-pub Aug. 4, 2008). "Local Delivery Of A Recombinant Adenoassociated Vector Containing A Tumour Necrosis Factor A Antagonist Gene In Inflammatory Arthritis: A Phase 1 Dose-Escalation Safety And Tolerability Study." Annals Of The Rheumatic Diseases 68(8):1247-1254.
Mietzsch, M. et al. (Mar. 2014). "Differential Adeno-Associated Virus Serotype-Specific Interaction Patterns With Synthetic Heparins And Other Glycans." Journal Of Virology 88(5):2991-3003.
Miltner, O. et al. (Sep. 2002). "Efficacy Of Intraarticular Hyaluronic Acid In Patients With Osteoarthritis—A Prospective Clinical Trial," Osteoarthritis And Cartilage 10(9):680-686.
Mingozzi et al. Prevalence and pharmacological modulation of humoral immunity to AAV vectors in gene transfer to synovial tissue. Gene Therapy (2013) 20, 417-424.
Momberger, T. S. et al. (Dec. 2005). "Hyaluronan Secretion By Synoviocytes Is Mechanosensitive," Matrix Biology 24(8):510-519, 18 pages.
Moreland LW. Intra-articular hyaluronan (hyaluronic acid) and hylans for the treatment of osteoarthritis: mechanism of action. Arthritis Res Ther 2003:5:54-67.
Nishida Y et al. Antisense inhibition of hyaluronan synthase-2 in human articular 25 chondrocytes inhibits proteoglycan retention and matrix assembly. JBC 1999, 274:1893-21899.
Okada. Efficient AAV Vector Production System: Towards Gene Therapy For Duchenne Muscular Dystrophy. Chapter 17.
Ortved, K.F. et al. (Feb. 2015, e-pub. Dec. 2, 2014). "Implantation of rAAV5-IGF-I Transduced Autologous Chondrocytes Improves Cartilage Repair in Full-thickness Defects in the Equine Model," Molecular Therapy 23(2):363-373.
Passini, M.A. et al. (Jun. 2003). "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of B-Glucuronidase-Deficient Mice," J. Virol. 77(12):7034-7040.
Payne, K.A. et al. (Aug. 2011). "Single Intra-Articular Injection Of Adeno-Associated Virus Results In Stable And Controllable In Vivo Transgene Expression In Normal Rat Knees." Osteoarthritis and Cartilage 19(8):1058-1065.
Pechan, P. et al. (Jan. 2009, e-pub. Jul. 17, 2008). "Novel Anti-VEGF Chimeric Molecules Delivered by AAV Vectors for Inhibition of Retinal Neovascularization," Gene Ther. 16(1):10-16.
Plickert et al. Hyaluronic acid concentrations in synovial fluid of dogs with different stagesof osteoarthritis. Res Vet Sci. Jun. 2013;94(3):728-34. doi: 10.1016/j.rvsc.2012.11.007. Epub Dec. 20, 2012.
Pritzker. Animal models for osteoarthritis: processes, problems and prospects. Annals of the Rheumatic Diseases 1994; 53: 406-420.
Rai et al. Conditioning and Scaffolding of Chondrocytes: Smart Steps Towards Osteoarthritis Gene Therapy. Chapter 9. Gene Therapy Application edited by Prof. Chunsheng Kang. 2011.
Rapti et al. Neutralizing Antibodies Against AAV Serotypes 1, 2, 6, and 9 in Sera of Commonly Used Animal Models. Molecular Therapy vol. 20 No. 1, 73-83 Jan. 2012.
Rhee, D.K. et al. (Sep. 2, 2005). "Consequences Of Disease-Causing Mutations On Lubricin Protein Synthesis, Secretion, And Post-Translational Processing," Journal of Biological Chemistry 280(35):31325-31332.
Ruan et al. Rubbing Arthritis the Wrong Way. Sci. Transl. Med. 5, 176ra34 (2013).
Sarzi-Puttini, P. et al. (2005). "Osteoarthritis: An Overview Of The Disease And Its Treatment Strategies," Seminars In Arthritis And Rheumatism. vol. 35. No. 1. WB Saunders, 10 pages.
Schmid, T.M. et al. (2002). "Superficial Zone Protein (SZP) Is An Abundant Glycoprotein In Human Synovial Fluid With Lubricating Properties," The Many Faces Of Osteoarthritis, Birkhäuser: Basel, 159-161.
Sharkey. The Challenges of Assessing Osteoarthritis and Postoperative Pain in Dogs. The AAPS Journal (2013).
Shin et al. Humoral Immunity to AAV-6, 8, and 9 in Normal and Dystrophic Dogs. Human Gene Therapy 23:287-294 (Mar. 2012).
Smith Jr., G.N. et al. (Jun. 1998). "Effect Of Intraarticular Hyaluronan Injection In Experimental Canine Osteoarthritis," Arthritis & Rheumatism: Official Journal Of The American College Of Rheumatology 41(6):976-985.

(56) References Cited

OTHER PUBLICATIONS

Swann, D.A. et al. (Jan. 1985). "The Molecular Structure And Lubricating Activity Of Lubricin Isolated From Bovine And Human Synovial Fluids," Biochemical Journal 225(1):195-201.

Vugmeyster, Y. et al. (Mar. 2012). "Disposition Of Human Recombinant Lubricin In Naive Rats And In A Rat Model Of Post-Traumatic Arthritis After Intra-Articular Or Intravenous Administration," The AAPS Journal 14(1):97-104.

Waller et al. Genetic Rescue of Lubricin-Null Mouse Knees Attenuates Cartilage Damage. ORS 2014 Annual Meeting Abstracts.

Waller et al. Role of lubricin and boundary lubrication in the prevention of chondrocyte apoptosis. www.pnas.org/cgi/doi/10.1073/pnas.1219289110.

Watanabe, K. et al. (Sep. 20, 1996). "Molecular Identification Of A Putative Human Hyaluronan Synthase," Journal of Biological Chemistry 271(38):22945-22948.

Watson et al. scAAV-mediated gene transfer of interleukin-1-receptor antagonist to synovium and articular cartilage in large mammalian joints.

Yoshida, M. et al. (Oct. 2004). "Expression Analysis Of Three Isoforms Of Hyaluronan Synthase And Hyaluronidase In The Synovium Of Knees In Osteoarthritis And Rheumatoid Arthritis By Quantitative Real-Time Reverse Transcriptase Polymerase Chain Reaction," Arthritis Res Ther 6(6):R514, 7 pages.

Zhang et al. Angiopoiesis and bone regeneration via coexpression of the hVEGF and hBMP genes from an adeno-associated viral vector in vitro and in vivo. Acta Pharmacologica Sinica (2010) 31: 821-830.

Zhang, D.-W., et al. (Jan. 2007). "Amelioration Of Osteoarthritis By Intra-Articular Hyaluronan Synthase 2 Gene Therapy," Medical Hypotheses 69(5):1111-1113.

Zhen et al. Inhibition of TGF-13 signaling in mesenchymal stem cells of subchondral bone attenuates osteoarthritis. Nature Medicine. accepted Feb. 21, 2013; published online May 19, 2013; doi:10.1038/nm.3143.

Casal, M. et al. (Mar. 2006, e-pub Dec. 7, 2005). "Large Animal Models And Gene Therapy," Eur J Hum Genet. 14(3):266-272.

Felsberg, P.J. (Sep.-Oct. 2002). "Overview Of Immune System Development In The Dog: Comparison With Humans," Hun Exp Toxicol. 21(9-10):487-492.

Robbins, P.D. et al. (1994). "Gene Therapy For Arthritis," ILAR Journal 36(3-4):53-56.

Frisbie, D.D. (2012). "Gene Therapy for Osteoarthritis," Equine Orthopaedic Research Center, College of Veterinary Medicine and Biological Science, and Molecular, Cellular & Tissue Engineering, Department of Mechanical Engineering, School of Biomedical Engineering, pp. 551-552, Abstract only.

Molecular Therapy (May 2008). "Biology of AAV Vector Transduction," The American Society of Gene Therapy 16(Supp 1):S1-S389.

NCBI (Nov. 6, 2012). "HAS2 Hyaluronan Synthase 2 [Felis Catus]," NCBI, Accession No. XP 004000138, retrieved on Mar. 16, 2022, 3 pages.

Yang, Q. et al. (Apr. 2007). "Cloning and Expression of Human Hyaluronan Synthase-2 in HEK 293 Cells," Science Technology and Engineering 7(8):1671-1819, 4 pages. (English Abstract Only).

Sun, Y et al. (2006). "Mapping Lubricin In Canine Musculoskeletal Tissues," Connective Tissue Research 47(4):215-221.

Sun, Y. et al. (Sep. 2006). "Expression And Mapping Of Lubricin In Canine Flexor Tendon," Journal Of Orthopaedic Research 24(9):1861-1868.

* cited by examiner

MQWKILPIYLLLLSVFLIQQVSSQDLPSCAGRCGEGYSRDAICNCDYNCQHY
MECCPDFKKACTVELSCKGRCFESFARGRECDCDSDCKKYGKCCPDYEDFCG
RVHNPTSPPSSKTAPPSPGASQTIKSTAKRSPKAPNKKKTKKVIESEEITEE
HSVSENQESSSSSSSSSTIRKIKSSKNSAANKELKKKPKVKDNKKERTPKK
KPPPEPPVVDEAGSGLDNGDIKLTPTPDIPTTQRNKVTTSPKFTTGKPINPK
PSLPPNTDTSKETSSTPNKETTVKSKETLANKETSSKAKEKITSAKETRSAE
KTPAKDFVPTTKAPVKSTPKAESTTKSPAPTTTKEPTPTTTKKPAPTTPKKP
APTTPKEPVPTTTKGPPTTPKKPEPTTPKDPAPTTTKEPTPTTPKKPAPTTK
EPVPITTKEPEPTTPKKPEPTTPKEPAPTTPKEPVPTTTKEPEPTTPKEPAP
TTPKEPAPTTPKEPVPTTTKEPPTTPKKPEPTTPKEPAPTTPKEPVPTTTKE
PEPTTPKELAPTTPKEPAPTTPKEPVPTTTKEPPTTPKKPEPTTPKEPAPTT
PKEPAPTTPKEPPTTPKKPEPTTPKEAAPTTKKPAATTPKEPAPTITKEPAP
TTPNKPEPTTPKEPVPTTPKEPEPTPPKEPAPTTTKDPAPTSPKEPTPTAPK
EPVPTAPKEPEPMAPKKPVPTAPKQPTPTTPKEPSPTVPKEPEPMAPKEPVP
TAPKKPAPTAPKDPAPTAPKEPEPTAPNKESAPTTSKEQVPITTKEPTPKLP
KEPAPASLETPAPTTSDAFTTTTMEPPTTPKNPAESTPKFPAEPTPKPLEN
SPKEPVVPITKAPEVTKPEMTTTAKDKTTEKDIIPEITTAVPKITTQETATP
TEETTTESKTSTTTQVTSTTSSKNTPKATTLAPKVMTATQKTTTTEETMNKP
EETTAVPKDTATSTKVSTPRPRKPTKAPKKPTSTKKPNTIPKRKKPKTTPTP
PKMTTSTMPKLHPTSSVEAMLQTTTSPNQRPNSEIVEVNPNEDTDAAGKKPH
MFPRPPVLTPIFIPGTDILVRGSNQDIAINPMLSDETNLCNGKPVDGLTTLR
NGTMVAFRGHYFWMLSPSNPPSPPRKITEVWGIPSPIDTVFTRCNCEGKTFF
FKGSQYWRFTNDIKDAGYPKQIVKGFGGLNGRIVAALSIAKYKDRPESVYFF
KRGGSVQQYTYKQEPIKKCTGRRPAINYPVGETTQVRRRRFERAIGPSQTH
TIRIHYSPIRVSYQDKGFLHNEVKMSSQWRGFPNVVTSAIALPNIRKPDGYD
YYAFSRNQYYNIDVPSRTARVVTTRFGRTLSNIWYNCP*

*FIG. 9*

| SEQ ID NO | Type | Description |
|---|---|---|
| 1 | DNA | Canine hyaluronic acid synthase 2 (cHAS2) - GenBank XM_539153.3 |
| 2 | Protein | cHAS2 polypeptide (translation of SEQ ID NO: 1 and 3) |
| 3 | DNA | Codon-optimized cHAS2 |
| 4 | DNA | Full-length Canine lubricin |
| 5 | Protein | Full-length Canine Lubricin protein - translation of SEQ ID NO: 4 |
| 6 | DNA | Codon-optimized truncated Lubricin (cLub) |
| 7 | Protein | Truncated codon-optimized cLub polypeptide - translation of SEQ ID NO: 6 |
| 8 | DNA | BGH-Forward Primer |
| 9 | DNA | BGH-Reverse Primer |
| 10 | DNA | BGH probe |
| 11 | Protein | Homo sapiens proteoglycan 4 (PRG4), transcript variant A, amino acid |
| 12 | DNA | Homo sapiens proteoglycan 4 (PRG4), transcript variant A, mRNA |

*FIG. 15*

```
Identities         Positives          Gaps
980/1413(69%)      1063/1413(75%)     83/1413(5%)

SEQ05    1  MQWKILPIYLLLL-SVFLIQQVSSQDLPSCAGRCGEGYSRDAICNCDYNCQHYMECCPDF   59
            M WK LPIYLLLL SVF+IQQVSSQDL SCAGRCGEGYSRDA CNCDYNCQHYMECCPDF
SEQ16    1  MAWKTLPIYLLLLLSVFVIQQVSSQDLSSCAGRCGEGYSRDATCNCDYNCQHYMECCPDF   60

SEQ05   60  KKACTVELSCKGRCFESFARGRECDCDSDCKKYGKCCPDYEDFCGRVHNPTSPPSSKTAP  119
            K+ CT ELSCKGRCFESF RGRECDCD+ CKKY KCCPDYE FC VHNPTSPPSSK AP
SEQ16   61  KRVCTAELSCKGRCFESFERGRECDCDAQCKKYDKCCPDYESFCAEVHNPTSPPSSKKAP  120

SEQ05  120  PSPGASQTIKSTAKRSPKAPNKKKTKKVIESEEITEEHSVSENQESSSSSSSSSS---TIR  177
            P  GASQTIKST KRSPK PNKKKTKKVIESEEITEEHSVSENQESSSSSSSSSS   TIR
SEQ16  121  PPSGASQTIKSTTKRSPKPPNKKKTKKVIESEEITEEHSVSENQESSSSSSSSSSSSTIR  180

SEQ05  178  KIKSSKNSAANKELKKKPKVKDNKKERTPKKKPPPEPPVVDEAGSGLDNGDIKLTPTPDI  237
            KIKSSKNSAAN+EL+KK KVKDNKK RT KK  P  P VVDEAGSGLDNGD K+T TPD
SEQ16  181  KIKSSKNSAANRELQKKLKVKDNKKNRTKKKPTPKPE-VVDEAGSGLDNGDFKVT-TPDT  238

SEQ05  238  PTTQRNKVTTSPKFTTGKPINPKPSLPPNTDTSKETSSTPNKETTVKSKETLANKETSS-  296
              TTQ NKV+TSPK TT KPINP+PSLPPN+DTSKETS T NKETTV++KET   + +S
SEQ16  239  STTQHNKVSTSPKITTAKPINPRPSLPPNSDTSKETSLTVNKETTVETKETTTTNKQTST  298

SEQ05  297  KAKEKITSAKETRSAEKTPAKDFVPTTKAPVKSTPKAESTTKSPAPTTTKEPTPTTTKKP  356
               KEK TSAKET+S EKT AKD  PT+K   K TPKAE+TTK PA TT KEPTPTT K+P
SEQ16  299  DGKEKTTSAKETQSIEKTSAKDLAPTSKVLAKPTPKAETTTKGPALTTPKEPTPTTPKEP  358

SEQ05  357  APTTPK-------KPAPTTPKEPVPTTTKGPPTTPKKPEPTTPKDPAPTTTKEPTPTTPK  409
            A TTPK       K APTTPKEP PTTTK  PTTPK+P PTT K+PAPTT KEP PTT K
SEQ16  359  ASTTPKEPTPTTIKSAPTTPKEPAPTTTKSAPTTPKEPAPTTTKEPAPTTPKEPAPTTTK  418

SEQ05  410  KPAPTTPKEPVPITTKEPEPTTPKKPEPTTPKEPAPTTP--------------KEPVPT  454
            +PAPTT K  P T KEP PTTPKKP PTTPKEPAPTTP              KEP PT
SEQ16  419  EPAPTTTKS-APTTPKEPAPTTPKKPAPTTPKEPAPTTPKEPTPTTPKEPAPTTKEPAPT  477

SEQ05  455  TTKEPEPTTPKEPAPTTPKEPAPTTPKEPVPTTTKEP-PTTPKKPE---------------  499
            T KEP PT PK+PAPTTPKEPAPTTPKEP PTTTKEP PTTPK+P
SEQ16  478  TPKEPAPTAPKKPAPTTPKEPAPTTPKEPAPTTTKEPSPTTPKEPAPTTTKSAPTTTKEP  537

SEQ05  500  -PTTPKEPAPTTPKEPVPTTTKEPEPTTPKELAPTTPKEPAPTTPKEPVPTTTKEPPTTP  558
             PTT K  APTTPKEP PTTTKEP PTTPKE APTTPK+PAPTTPKEP PTT KEP   T
SEQ16  538  APTTTKS-APTTPKEPSPTTTKEPAPTTPKEPAPTTPKKPAPTTPKEPAPTTPKEPAPTT  596

SEQ05  559  KKPEPTTPK-EPAPTTPKEPAPTTP--------KEPPTTPKKPEPTTPKEAAPTTKKPA  608
             K    T    EPAPTTPKE APTTP        K  PTTP+KP PTTP+E APTT +
SEQ16  597  TKKPAPTTPKEPAPTTPKETAPTTPKKLTPTTPEKLAPTTPEKPAPTTPEELAPTTPEEP  656

SEQ05  609  ATTP---------KEPAPTITKEPAPTTPNKPEPTTPKEPVPTTPKEPEPTPPKEPAPTT  659
              T          K  AP  KEPAPTTP +P PTTPKEP PTTPKE  PT PK  APTT
SEQ16  657  TPTTPEEPAPTTPKAAAPNTPKEPAPTTPKEPAPTTPKEPAPTTPKETAPTTPKGTAPTT  716
```

*FIG. 16*

```
SEQ05   660  TKDPAPTSPKEPTPTAPKEPVPTAPKEPEPMAPKKPVPTAPKQPTPTTPKEPSPTVPKEP   719
             K+PAPT+PK+P   APKE  PT  KEP      KP PT  PK    PTTPKEP+PT PKEP
SEQ16   717  LKEPAPTTPKKP---APKELAPTTTKEPTSTTSDKPAPTTPKGTAPTTPKEPAPTTPKEP   773

SEQ05   720  EPMAPKEPVPTAPKKPAPTAPKDPAP--TAPKEPEPTAPNKES--APTTSKEQVPITTKE   775
             P   PK   PT  K+PAPT PK PAP   AP    +         APTT KE  P T KE
SEQ16   774  APTTPKGTAPTTLKEPAPTTPKKPAPKELAPTTTKGPTSTTSDKPAPTTPKETAPTTPKE   833

SEQ05   776  PTPKLPKEPAPASLETPAPTTSDAFTTTTTMEPPTTPKNPAESTPKFPAEPTPKPLENSP   835
             P P   PK+PAP + ETP PTTS+  T TTT EP T  K+P ESTP+  AEPTPK LENSP
SEQ16   834  PAPTTPKKPAPTTPETPPPTTSEVSTPTTTKEPTTIHKSPDESTPELSAEPTPKALENSP   893

SEQ05   836  KEPVVPITKAPEVTKPEMTTAKDKTTEKDIIPEITTAVPKITTQETATPTEETTTESKT   895
             KEP VP TK P  TKPEMTTAKDKTTE+D+     T        +    T E TTESK
SEQ16   894  KEPGVPTTKTPAATKPEMTTAKDKTTERDLRTTPETTTAAPKMTKETATTTEKTTESKI   953

SEQ05   896  STTTQVTSTTSSKNT-PKATTLAPKVMTA-----TQKTTTTEETMNKPEETTAVPKDTAT   949
             +  TT   ++T++++T P    T    A      T+KT TT E MNKPEET A PKD AT
SEQ16   954  TATTTQVTSTTTQDTTPFKITTLKTTTLAPKVTTTKKTITTTEIMNKPEET-AKPKDRAT   1012

SEQ05   950  STKVSTPRPRKPTKAPKKPTSTKKPNTIPKRKKPKTTPTPPKMTTSTMPKLHPTSSV-EA   1008
             ++K +TP+P+KPTKAPKKPTSTKKP T+P+  +KPKTTPTP KMT STMP+L+PTS + EA
SEQ16  1013  NSKATTPKPQKPTKAPKKPTSTKKPKTMPRVRKPKTTPTPRKMT-STMPELNPTSRIAEA   1071

SEQ05  1009  MLQTTTSPNQRPNSEIVEVNP-NEDTDAA-GKKPHMFPRPPVLTPIFIPGTDILVRGSNQ   1066
             MLQTTT PNQ PNS++VEVNP +ED   A G+ PHM  RP V P    P  D L R  NQ
SEQ16  1072  MLQTTTRPNQTPNSKLVEVNPKSEDAGGAEGETPHMLLRPHVFMPEVTPDMDYLPRVPNQ   1131

SEQ05  1067  DIAINPMLSDETNLCNGKPVDGLTTLRNGTMVAFRGHYFWMLSPSNPPSPPRKITEVWGI   1126
              I INPMLSDETN+CNGKPVDGLTTLRNGT+VAFRGHYFWMLSP +PPSP R+ITEVWGI
SEQ16  1132  GIIINPMLSDETNICNGKPVDGLTTLRNGTLVAFRGHYFWMLSPFSPPSPARRITEVWGI   1191

SEQ05  1127  PSPIDTVFTRCNCEGKTFFFKGSQYWRFTNDIKDAGYPKQIVKGFGGLNGRIVAALSIAK   1186
             PSPIDTVFTRCNCEGKTFFFK SQYWRFTNDIKDAGYPK I KGFGGL G+IVAALS AK
SEQ16  1192  PSPIDTVFTRCNCEGKTFFFKDSQYWRFTNDIKDAGYPKPIFKGFGGLTGQIVAALSTAK   1251

SEQ05  1187  YKDRPESVYFFKRGGSVQQYTYKQEPIKKCTGRRPAINYPVYGETTQVRRRRFERAIGPS   1246
             YK+ PESVYFFKRGGS+QQY YKQEP++KC GRRPA+NYPVYGETTQVRRRRFERAIGPS
SEQ16  1252  YKNWPESVYFFKRGGSIQQYIYKQEPVQKCPGRRPALNYPVYGETTQVRRRRFERAIGPS   1311

SEQ05  1247  QTHTIRIHYSPIRVSYQDKGFLHNEVKMSSQWRGFPNVVTSAIALPNIRKPDGYDYYAFS   1306
             QTHTIRI YSP R++YQDKG LHNEVK+S  WRG PNVVTSAI+LPNIRKPDGYDYYAFS
SEQ16  1312  QTHTIRIQYSPARLAYQDKGVLHNEVKVSILWRGLPNVVTSAISLPNIRKPDGYDYYAFS   1371

SEQ05  1307  RNQYYNIDVPSRTARVVTTRFGRTLSNIWYNCP   1339
             ++QYYNIDVPSRTAR +TTR G+TLS +WYNCP
SEQ16  1372  KDQYYNIDVPSRTARAITTRSGQTLSKVWYNCP   1404
```

*FIG. 16 (Cont'd)*

RECOMBINANT AAV VECTORS EXPRESSING OSTEOPROTECTIVE GENES, INCLUDING HAS2 AND LUBRICIN, USEFUL IN THE TREATMENT OF OSTEOARTHRITIS AND RELATED JOINT CONDITIONS IN MAMMALS

CROSS-REFERENCE TO RELATED APPLICATIONS

This application is a continuation of U.S. patent application Ser. No. 15/405,992, filed on Jan. 13, 2017 (now abandoned), which claims priority to U.S. provisional application No. 62/278,243, filed on Jan. 13, 2016, each of which is herein incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is MER 16-291 SEQ Listing_ST25.txt. The text file is 57.6 KB; it was created on Jan. 13, 2016; and it is being submitted electronically via EFS-Web, concurrent with the filing of the specification.

FIELD OF THE INVENTION

The present invention relates to recombinant vectors, to pharmaceutical compositions comprising such recombinant vectors, and to methods for prevention and/or treatment of acute and/or chronic joint conditions, including osteoarthritis, in mammals. In particular, the invention relates to adeno-associated virus (AAV) vectors capable of expressing, in a host, a bioactive polypeptide belonging to the hyaluronan synthase 2 (HAS2) and lubricin (PRG4) family of proteins. Accordingly, the invention relates to the field of genetic engineering and provides an adeno-associated virus (AAV)-based biological delivery and expression system for use in the treatment of osteoarthritis in human or mammalian joints by long-term gene expression of HAS2 and LUB in synovial and chondrocyte cells.

SUMMARY OF THE INVENTION

Osteoarthritis (OA) is a degenerative joint disease that occurs in mammalian joints and constitutes a severe economical and medical problem (Matthews, G. L., and Hunter, D. J. (2011). Expert Opin. Emerging Drugs 1-134 Brooks P M. Curr Opin Rheumatol 2002; 14: 573-577). Cartilage is the tough connective tissue that covers the ends of bones in joints. It provides for a relatively frictionless, highly lubricated surface between rigid bones and allows for a smooth movement. During OA development, cartilage is partially or completely lost due to abnormal or excessive wearing, which leads to exposed bone ends that rub against each other resulting in inflammation, pain, swelling or loss of mobility. Currently, the detailed reasons for the initial cartilage loss that leads to OA are not known, but there is a strong correlation between the incidence and age, obesity and joint overuse such as excessive athletic activity.

In dogs, osteoarthritis (OA) is one of the most common causes of lameness, and it is estimated to affect approximately 20 percent of dogs over the age of one year. No curative treatment is currently available for OA, so medical treatment has largely targeted symptom alleviation rather than re-establishment of cartilage. An analgesic treatment usually involves steroids and non-steroidal anti-inflammatory drugs (NSAIDS), which have shown efficacy in the treatment of OA for some decades. However, while these drugs can suppress joint inflammation, many of them are known to have deteriorating effects on the cartilage, which further worsens the underlying process of OA development. In addition to traditional analgesic and anti-inflammatory therapies, direct administration of naturally-occurring osteoprotective compounds has been used to alleviate OA symptoms, varying degrees of success. For example, hyaluronic acid (HA) has been widely used to restore viscoelasticity and lubrication of affected joints. Also, polysulphated glycosaminoglycans (PSGAGs), injected via the intra-articular or intramuscular route, and orally-administered glucosamine and chondroitin sulphate have shown some efficacy.

However, the foregoing drugs must be administered frequently, sometimes even in combination with each other, to achieve meaningful alleviation of symptoms. These frequent joint injections are laborious/costly, bear the risk for infections, and cause a great deal of stress for the patient or animal. And while surgical approaches have also been developed, these have generally shown low efficacy in dogs and horses, and are typically only performed in severe advanced-stage subjects.

In addition to delivering supplements/drugs, several groups have attempted to improve OA symptoms by delivering viscoelastic/viscoprotective polypeptides, nucleic acids encoding same, or polypeptides or nucleic acids capable of expressing in a host the means for producing a viscoprotective protein (e.g., an enzyme). Approaches of greater interest include the use of lubricin polypeptides (Flannery, U.S. Pat. No. 7,642,236 B2), tribonectins (U.S. Pat. No. 7,618,914 B2, to Rhode Island General Hospital), and hyaluronan synthase (U.S. Pat. No. 6,423,514, to Millennium Pharmaceuticals).

Some of these efforts may be characterized as "gene therapy," the basic concepts of which are well established (Evans C H, Robbins PD. Gene therapy for arthritis, In: Wolff J A (ed.). Gene Therapeutics: Methods and Applications of Direct Gene Transfer. Birkhauser: Boston, 1994, pp 320-343). Recently, one group has tried to treat osteoarthritis by the in vivo delivery of the interleukin-1 receptor antagonist (Il-1Ra) gene (US 2015/0031083 A1, to Baylor College of Medicine; and see Frisbie, D D et al., Gene Therapy (2002)).

The Arthrogen company has used AAV to express human interferon beta (to reduce inflammatory cytokine) in the context of rheumatoid arthritis (RA). Unlike OA, inflammatory signaling plays a significant role in the pathology of RA, and so blocking this signal is a key therapeutic approach. That said, another group, pursuing a possible link between inflammation and OA, used recombinant AAV2 to express an IL1 receptor antagonist, in the context of equine OA (Goodrich et al., Molecular Therapy-Nucleic Acids (2013) 2, e70).

However, none of these approaches has proven universally effective, and there remain significant unmet needs as to relief of pain and suffering for OA patients. It follows that there is a clear and yet unmet medical need for more efficacious and sustained treatments that are at the same time also cost effective in the long run.

Accordingly, as described in detail herein, Applicants successfully demonstrated for the first time that recombinant adeno-associated virus (rAAV) vectors could deliver cDNAs encoding therapeutic agents by a single intra-articular injection into a mammalian joint to facilitate local and continuous production of the agent in vivo in synoviocytes and chondrocytes.

Applicants have also isolated and sequenced, for the first time, a full length canine lubricin cDNA (SEQ ID NO:4).

The present invention provides rAAV vectors that express in vivo, in a mammalian host, therapeutically effective amounts of osteo-protective and/or osteo-regenerative gene products.

In aspects, the rAAV may contain cDNA encoding for an agent with disease-modifying, lubricating, anti-inflammatory and pain relief properties.

In aspects, the rAAV vector is a vector derived from an AAV serotype, including without limitation, AAV1, AAV2, AAV3, AAV4, AAV5, AA6, AAV7, AAV8, AAV9, AAVrh.8, and AAVrh.10. In some embodiments, the nucleic acid in the AAV comprises an ITR of AAV1, AAV2, AAV3, AAV4, AAV5, AAV6, AAV7, AAV8, AAV9, AAVrh.8, or AAVrh.10. In further embodiments, the rAAV particle comprises capsid proteins of AAV1, AAV2, AAV3, AAV4, AAV5, AA6, AAV7, AAV8, AAV9, AAVrh.8, or AAVrh.10. In some embodiments, the ITR and capsid are derived from the same AAV serotype. In other embodiments, the ITR and capsid are derived from different AAV serotypes. In some embodiments, the rAAV vectors may be AAV2 or AAV capsid serotypes. In some related embodiments, the rAAV2 and rAAV5 vectors contain at least one ITR that is derived from AAV2.

In aspects embodiments, the rAAV vectors encode hyaluronic acid synthase-2 (HAS2) or variant thereof. In some embodiments, the HAS2 is human HAS2. In other embodiments, the HAS2 is canine HAS2. In some embodiments, the HAS2 is codon-optimized HAS2.

Glycosaminoglycan hyaluronan acid (HA) is a non-sulfated glycosaminoglycan consisting of repeating glucuronic acid and N-acetylglucosamine residues linked by beta-1-3 and beta-1-4 glycosidic bonds. It provides multiple biological functions including wound healing, cell migration, malignant transformation and tissue turnover. HA is synthesized by various cell types including endothelial cells, fibroblasts and smooth muscle cells and has been detected in tissues such as connective, epithelial and neural tissues. In the joint space, HA is made by synoviocytes that secrete HA into synovial fluid as well as by chondrocytes. The synovial fluid HA provides lubrication, tissue hydration, structural integrity and scaffold for matrix proteins and biomechanics as well as plays a role in joint homeostasis. The biological effects of HA in the joint are determined by its concentration and molecular weight. It can be synthesized ranging from 5000 Da to 10,000 000 Da. The lower molecular weight HA (<500 kDa) is involved in receptor-mediated activation of angiogenesis, malignancy and inflammation while the higher molecular weight HA provides lubrication in the joint.

The sizes and concentration of joint HA is regulated both by its rate of synthesis and degradation. Degradation of HA is mediated by hyaluronidases that cleave HA into smaller fragments that drain into lymphatic system for clearance. Three enzymes, named as hyaluronan synthase (HAS) 1, 2, and 3 have been described for HA production and reside at the inner surface of plasma membrane of synoviocytes. Of these, HAS2 has been shown to be responsible for production of high molecular weight HA (Itano et al. 1999). It has been reported that the high molecular weight HA levels are decreased in osteoarthritic joints both in human patients and animal OA models (Plickert et al., 2013). This is likely due to both reduced synthesis of HA and increased degradation of HA by the hyaluronidases. Of the HA synthases, HAS2 and 3 are expressed in human cartilage and of these, HAS2 expression is reduced in human OA. HA levels are also reduced due to increased levels of HA degrading enzyme, hyaluronidase 2 (Yoshida et al.). The HAS2 promoter has been reported to be responsive to various pro- and anti-inflammatory mediators with conflicting effects reported. These include TGFβ, primary epidermal growth factor, TNF alpha and retinoic acid (Guo, Kanter el al, 2007, Hyc et al., 2009). Down-regulation by inflammatory mediators in diseased joint is expected to reduce HAS2 expression resulting decreased HA levels and can differentially affect various HAS isoforms (David-Raoudi et al., 2009). In contrast, mechanical stimulation (Momberger et al. 2005) or cartilage components such as chondroitin sulfate have been reported to stimulate HA production (Momberger et al., 2005, David-Raoudi et al., 2009). HA production results in pericellular location as well as secretion into extracellular space. It is not clear what regulates the extent of secretion. However, typically about 80% of the HA is secreted while the remainder remains associated with producing cells. This cell-associated HA is important for assembly of matrix proteins; blocking HAS2 synthesis results in decreased cell-associated matrix and increased release of proteoglycans (i.e. aggrecan) into media furthermore confirming major role of HAS2 as major enzyme synthesizing HA in chondrocytes (Nishida et al. 1999).

In aspects embodiments, the rAAV vectors encode lubricin or a variant thereof. In some embodiments, the lubricin is human lubricin. In other embodiments, the lubricin is canine lubricin. In some embodiments, the lubricin is codon-optimized lubricin.

Lubricin (PRG4), which is a large mucin glycoprotein made by joint synovial lining cells and cartilage chondrocytes and provides a protective lubrication for cartilage surfaces (Flannery 1999, Schmidt 2001, Waller 2013). Lubricin along with HA is also an important lubricant in the synovial fluid providing shock-absorbing properties. Lack of lubricin in mouse models and in a rare human genetic disease results in cartilage degeneration characteristic of osteoarthritis (OA) (Rhee 2005, Ruan 2013). Decreased synthesis of lubricin has also been demonstrated in human OA patients and various animal OA models (Elsaid, 2008). Intra-articular lubricin supplementation with recombinant lubricin has been shown to improve cartilage pathology (Flannery 2009).

In some embodiments, the rAAV vectors may be AAV2 or AAV5 capsid serotypes encoding canine codon-optimized hyaluronic acid synthase-2 (HAS2).

In aspects, the rAAV vector is administered via intra-articular delivery. In embodiments, the rAAV are administered via a single intra-articular delivery. In another embodiment, following the intra-articular administration, in vivo production and secretion of the cognate therapeutic agent from the rAAV-transduced cells may persist for at least about 6 months.

In some embodiments, the rAAV vector contains an expression cassette containing an ubiquitous promoter and a codon-optimized and species-matched transgene (see e.g. FIG. 1A).

In another aspect, the disclosure provides a method of using the rAAV vectors to express in vivo in an animal's joint osteo-protective and/or osteo-regenerative gene products.

All references cited herein, including patent applications and publications, are incorporated by reference in their entirety.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 9 shows the complete amino acid sequence of canine lubricin (SEQ ID NO: 5). The boxed area indicates location of exon 6 (mucin domain). The underlined amino acids (378 to 782) are deleted in the shortened canine lubricin (hereinafter "cLubi" or "cLubico"), and the locations of KEPAPTT-like repeats (potential O-linked glycosylation sites) are in bold. When a sequence name ends in "co," it means the cDNA sequence has been "codon-optimized." Similarly, "nonco" means non-codon-optimized.

FIG. 15 is a table presenting of summary of SEQ ID NOs.

FIG. 16 is an alignment of canine and human lubricin.

DETAILED DESCRIPTION OF THE INVENTION

Figure 1A:
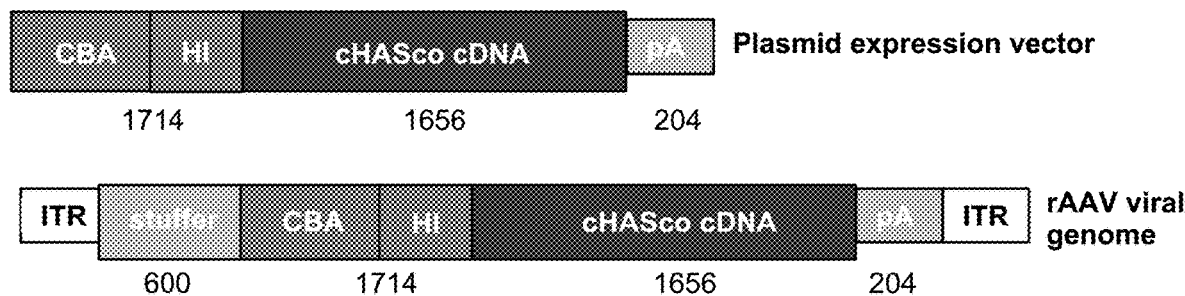
FIG. 1A is a diagram showing the HAS expression cassette in a plasmid (top) and rAAV viral vector (bottom).

Osteoarthritis (OA) is one of the most common causes of lameness in mammals, and in dogs and is estimated to affect approximately 20% of dogs >1 year old. OA is a progressive and degenerative disease resulting in pain, inflammation and reduced joint mobility. Novel safe and efficacious therapies that improve joint lubrication and reduce inflammation and pain are needed to manage OA. As disclosed herein, Applicants discovered that recombinant adeno-associated virus (rAAV) vectors can be used to deliver genes encoding therapeutic agents by a single intra-articular injection with the goal to provide local and continuous production of the agent in the joint. rAAV vectors were generated with AAV2 and AAV5 capsid serotypes and encoding canine codon-optimized hyaluronic acid (HA) synthase-2 (HAS2).

Twenty-two adult healthy dogs, seronegative for AAV2 and AAV5 capsids received rAAV2 (1, 5 and $10 \times 10^{11}$ vg/joint), rAAV5 ($5 \times 10^{11}$ vg/joint) or PBS (control) via intra-articular injection. No adverse clinical signs were observed following the 28-day study. Histopathological analysis showed minimal synovial inflammation in joints treated with rAAV5 and no significant changes in the rAAV2 treatment groups. Vector genomes (VG) were detected in the synovium of all the rAAV-treated joints and in the majority of cartilage samples. The rAAV5 vectors resulted in higher VG detection and mRNA expression compared to rAAV2 in both tissues. A preliminary analysis also showed a trend of increased HA levels in the synovial fluid of the treated joints. In summary, our study demonstrated gene transfer to canine joint tissues and an acceptable safety profile with rAAV2 and rAAV5 vectors encoding HAS2 when administered by single intra-articular injection in a limited number of dogs.

Canine HA synthase 2. In an aspect of the invention, the disclosure provides a recombinant adeno-associated virus (rAAV) vector comprised of AAV capsid and a single-stranded DNA genome. Viral capsids according to the disclosure may confer uptake of the vector into joint cells, with subsequent transport to the cell's nucleus, resulting in expression of a therapeutic gene. In some embodiments, the DNA genome contains one or more AAV inverted terminal repeats (ITRs) flanking one or more expression cassette(s), for expressing in vivo in an animal host the therapeutic gene. In some embodiments of the invention, no viral genes will be present or expressed from the rAAV genome.

In some embodiments of the invention, once the rAAV has been administered to an animal and is taken up by the animal's cells, the rAAV genome will persist as an extra-chromosomal episome. In some embodiments, the rAAV of the disclosure may persist long-term in the joint cells; for example, but not limited to more than about 1 month, 2 months, 3 months, 4 months, 5 months, 6 months, 7 months, 8 months, 9 months, 10 months, 11 months, 1 year, 2 years, or 3 years. The episomal rAAV will continue to express, resulting in the production and secretion of the therapeutic agent into synovial fluid, thereby providing a local and continuous production of the agent directly into the joint. The selected transgene product may promote joint health by increasing joint lubrication, reducing pain and cartilage degradation and the like.

In a another aspect of the invention, the disclosure provides a method of treating an animal in need thereof comprising the step of administering to the animal a therapeutically effective amount of a rAAV according to the disclosure. In some embodiments, the method comprises administering to canines the proposed product directly into its affected joint. In some embodiments, a single treatment is sufficient to affect significant improvement in the animal's condition.

In other embodiments, the treatment is repeated. In some embodiments, the treatment is repeated within 2-3 weeks of the first administration, and in other embodiments, the second administration is given greater than 3 weeks after the first. In some related embodiments, the second dose comprises administration of a rAAV with the same therapeutic gene and the rAAV comprises the same serotype capsid as the first treatment, and in other related embodiments, the second dose comprises administration of a rAAV with the same therapeutic gene but the rAAV comprises a different serotype capsid as the first dose. In some embodiments, the rAAV has a serotype 5 capsid. In related embodiments, where repeated administration is desired, the first dose may comprise administration of a rAAV having a serotype 5 capsid and the second dose may comprise administration of a rAAV having a serotype 5 capsid.

In aspects, overexpression of the HAS2 protein in the osteoarthritic joint elevates levels of HA in synovial fluid and improves joint health by increasing lubricating, anti-inflammatory and pain relief properties of HA. Overexpression of HAS2 has been shown to result in elevated levels of HA in the culture media by various cell types in vitro. This has been demonstrated using CHO, 293, and COS cells either as stable transfectant or transient transfection. To provide overexpression of HA in the joint in vivo, the HAS2 cDNA can be delivered to cartilage and/or synovium, the normal sites of HA synthesis by using rAAV vector encoding HAS2 expression cassette. Not wishing to be bound by any theory, gene transfer to cells will provide HAS2 expression cassette for sustained expression of HAS2 and subsequent production of HA. As the therapeutic vector will contain a ubiquitous promoter, it will not be subject to down-regulation by inflammatory mediators present in the osteoarthritic joint unlike the endogenous HAS2 promoter. When the vector is administered by intra-articular injection it can result in transduction of various cell types, the major cell types being synoviocytes. Lastly, the HAS2 protein alone has been shown to be sufficient to synthesize HA and no other associated proteins or components are thought to be necessary for HA production in vitro (Yoshida et al.).

Canine lubricin. In aspects, lubricin production in osteoarthritic joints is increased by intra-articular delivery of recombinant adeno-associated virus (rAAV) vector encoding lubricin as a potential treatment for canine osteoarthritis (OA). Lubricin is a large secreted glycoprotein that functions as a lubricant and protects cartilaginous surfaces in a joint. A Described herein is the discovery and generation of cDNA for a full-length canine lubricin that was used to design a shortened and codon-optimized version of canine lubricin (cLub1co). The latter was then used to construct various lubricin expressing plasmids. The plasmids were characterized for lubricin mRNA and protein production after transfection into HEK293 cells. The data showed both production of lubricin mRNA and secreted lubricin from each construct. rAAV vectors were generated with cLub1co expression cassette and demonstrated the feasibility of rAAV/cLub1 vector production. HEK293 cells infected with this construct synthesized and secreted canine lubricin.

The methods and compositions described herein can also be used for therapeutic treatment of osteoarthritis. The terms "therapy" or "therapeutic treatment", as they relate to osteoarthritis, and as they are used herein and in the field of veterinary medicine, relate to treating, or supporting and/or accelerating treatment of, subjects that are already suffering from, or are recovering from (e.g., are in the recovery phase) osteoarthritis, or treatments aimed at slowing down and/or reversing cartilage loss in subjects diagnosed as having, or at being at risk of, osteoarthritis. A critical objective of therapy is to reduce the risk of an evolution towards cartilage and bone loss. As used herein, a subject is said to suffer from osteoarthritis, or be at risk of developing osteoarthritis, if the subject is reasonably expected to suffer a progressive cartilage loss associated with osteoarthritis. Whether a particular subject suffers of osteoarthritis, or is at risk of developing osteoarthritis, can readily be determined by one with ordinary skill in the relevant veterinary or medical art.

The methods and compositions described herein may also be used for preventative treatment of osteoarthritis. The terms "prevention", "prophylaxis", "preventative treatment" and "prophylactic treatment", as they relate to osteoarthritis, and as they are used herein and in the field of human and veterinary medicine, relate to the treatment of either healthy subjects or subjects suffering from an unrelated disease, but who are considered to be at risk of osteoarthritis.

Described herein are therapies and preventative treatments for osteoarthritis that utilize pharmaceutical compositions comprising vectors capable of expressing HAS or Lubricin polypeptides in vivo and methods and compositions for inducing a sustained increase in joint hyaluronic acid or lubricin concentrations, to reduce or eliminate cartilage loss.

As used herein, a pharmaceutical composition is said to have "therapeutic efficacy", or to be "therapeutically effective", if administration of that amount of the composition is sufficient to cause a significant improvement of the clinical signs or measurable markers of the disease in a mammalian subject suffering from osteoarthritis. As used herein, a pharmaceutical composition is said to have "prophylactic efficacy" or to be "an effective", if administration of that amount of the composition is sufficient to prevent the development of osteoarthritis in a subject.

Also described herein is a vector capable of expressing, in vivo in a host, a HAS or lubricin polypeptide, or variants or fragments or combinations thereof. In embodiments, the HAS or lubricin polypeptides for use in the present invention are genetically matched to the intended target species (e.g., vectors encoding canine HAS2 are delivered to canines suffering from OA).

By way of illustration of "variants," "derivatives," and the like described herein include, but are not limited to, HAS and lubricin variants, derivatives, and the like that are encoded by nucleotide sequences that are not exactly the same as the nucleotide sequences disclosed herein, but wherein the changes in the nucleotide sequences do not change the encoded amino acid sequence, or result in conservative substitutions of amino acid residues, deletion of addition of one or a few amino acids, substitution of amino acid residues by amino acid analogues that do not significantly affect the properties of the encoded polypeptides (e.g., the variant or derivative has more than about 10%, 20%, 30%, 40%, 50%, 60%, 70%, 80%, 90%, 95%, 99% or 100% of the desired activity of wild type polypeptide), and the like. Examples of conservative amino acid substitutions include glycine/alanine substitutions; valine/isoleucine/leucine substitutions; asparagine/glutamine substitutions; aspartic acid/glutamic acid substitutions; serine/threonine/methionine substitutions; lysine/arginine substitutions; and phenylalanine/tyrosine/tryptophan substitutions. Other types of substitutions, variations, additions, deletions and derivatives that result in functional HAS or lubricin derivatives, are also described herein, and one of skill in the art would readily know how to make, identify, or select such variants or derivatives, and how to test for HAS or lubricin activity of those variants or derivatives. One of skill in the art may optimize the expression of the HAS or lubricin polypeptides of the invention; for example, but not limited to removing cryptic splice sites, adapting the codon usage by introducing a Kozak consensus sequence before the start codon, changing the codon usage or combination thereof to improve expression.

The vector for use in the present invention may comprise a nucleic acid sequence encoding a canine HAS2 polypeptide comprising the amino acid sequence set forth in SEQ ID NO: 2. In some embodiments, the canine HAS2 polypeptide is a canine HAS2 variant having at least 90%, at least 91%, at least 92%, at least 93%, at least 94%, at least 95%, at least 96%, at least 97%, at least 98% or at least 99% homology or identity to SEQ ID NO: 2.

The vector for use in the present invention may comprise a nucleic acid sequence encoding a canine lubricin polypeptide comprising the amino acid sequence set forth in SEQ ID NO: 7. In some embodiments, the canine lubricin polypeptide is a canine lubricin variant having at least 90%, at least 91%, at least 92%, at least 93%, at least 94%, at least 95%, at least 96%, at least 97%, at least 98% or at least 99% homology or identity to SEQ ID NO: 7.

Sequence identity or homology may be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990, 87, 2264-2268, modified as in Karlin & Altschul, Proc. Natl. Acad. Sci. USA 1993,90, 5873-5877.

Another example of a mathematical algorithm used for comparison of sequences is the algorithm of Myers & Miller, CABIOS 1988, 4, 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988, 85, 2444-2448.

In general, comparison of amino acid sequences may be accomplished by aligning an amino acid sequence of a polypeptide of a known structure with the amino acid sequence of a the polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

The terms "protein", "polypeptide" and "polypeptide fragment" are used interchangeably herein to refer to polymers of amino acid residues of any length.

As used herein the term "polynucleotide" is used to refer to a polymeric form of nucleotides of any length, which contain deoxyribonucleotides or ribonucleotides.

The term "vector", as used herein, refers to a recombinant DNA or RNA plasmid or virus that comprises a heterologous polynucleotide to be delivered to a target cell, such as in vivo. The heterologous polynucleotide may comprise a sequence of interest for purposes of therapy, and may optionally be in the form of an expression cassette. As used herein, a "vector" need not be capable of replication in the ultimate target cell or subject.

The term "recombinant" as used herein means a polynucleotide semisynthetic, or synthetic origin, which either does not occur in nature or is linked to another polynucleotide in an arrangement not found in nature.

The term "heterologous" as used herein derived from a genetically distinct entity from the rest of the entity to which it is being compared. For example, a polynucleotide may be placed by genetic engineering techniques into a plasmid or vector derived from a different source, and is thus a heterologous polynucleotide. A promoter removed from its native coding sequence and operably linked to a coding sequence other than the native sequence is accordingly a heterologous promoter.

The polynucleotides for use according to the invention may comprise additional sequences, such as additional coding sequences within the same transcription unit, controlling elements such as promoters, ribosome binding sites, transcription terminators, polyadenylation sites, additional transcription units under control of the same or different promoters, sequences that permit cloning, expression, homologous recombination, and transformation of a host cell, and any such construct as may be desirable to provide embodiments of this invention.

In an aspect, the disclosure provides a method of treating a mammalian subject suffering from, or at risk of developing, osteoarthritis (OA), comprising administering to said mammalian subject a therapeutically effective amount of an adeno-associated virus (AAV) containing a nucleic acid sequence encoding an osteo-protective or osteo-regenerative polypeptide and operably linked to a promoter, wherein the polypeptide is expressed in vivo in the mammalian subject and, in an amount effective to alleviate or prevent the symptoms of OA. In some embodiments, the administration is via the intra-articular route.

In some embodiments, the polypeptide may encode a hyaluronic acid synthase (HAS), including HAS2 (HAS2), a lubricin, an Interleukin-1 Receptor (IL-1R) antagonist, an Insulin-like growth factor 1 (IGF-1), a fibroblast growth factor 2 (FGF-2), a Transforming growth factor beta 1 (TGFβ1), a Bone Morphogenetic protein 7 (BMP7), a Glucosamine-fructose-6-phosphate aminotransferase (GFAT), an Interleukin 10 (IL-10), a heme oxygenase-1 HO-1, biologically active truncations thereof, or combinations thereof. In an embodiment, the mammalian subject may be a human, a canine or a feline. In a particular embodiment, the subject is a canine.

In some embodiments, the mammalian subjects are suffering from, or are at risk of developing chronic osteoarthritis.

In other embodiments, the polypeptide is canine HAS2 or canine lubricin. In a some embodiments, the nucleic acid sequence encoding the HAS2 polypeptide has a sequence having at least 90% identity to the sequence as set forth in SEQ ID NO: 3, or the nucleic acid sequence encoding the lubricin polypeptide has a sequence having at least 90% identity to the sequence as set forth in SEQ ID NO: 6.

In some embodiments, the HAS2 polypeptide comprises the amino acid sequence set forth in SEQ ID NO: 2. In some embodiments, the HAS2 polypeptide has an amino acid sequence selected from a polypeptide having at least 90% identity to the sequence as set forth in SEQ ID NO: 2, a fragment, a variant, and a homolog thereof having, each exhibiting HAS activity in vivo in the subject. "HAS activity" means production of biologically active hyaluronic acid.

In some embodiments, the AAV vector comprises from 5' to 3' the following elements: 5' AAV ITR, stuffer, CBA, intron (IN), cHAS2 codon-optimized cDNA, polyadenylation signal (pA), and 3' AAV ITR.

In some embodiments, the lubricin polypeptide comprises the amino acid sequence set forth in SEQ ID NO: 7. In other embodiments, the lubricin polypeptide has an amino acid sequence selected from a polypeptide having at least 90% identity to the sequence as set forth in SEQ ID NO: 7, a fragment, a variant, and a homolog thereof having, each exhibiting lubricin activity in vivo in the subject. "Lubricin activity" means providing lubrication in substantially the same way, and substantially to the same extent, as endogenously-produced lubricin. Such lubricating activity may be measured according to techniques known in the art (see e.g. Swan, D A et al. Biochem J. 1985 Jan. 1; 225(1): 195-201).

In some embodiments, the promoter may be selected from the group consisting of a CMV IE promoter, a RSV promoter, an HSV-1 TK promoter, a SV40 early promoter, a SV40 late promoter, an adenovirus major late promoter, a phosphoglycerate kinase gene promoter, a metallothionein gene promoter, an α-1 antitrypsin gene promoter, an albumin gene promoter, a collagenase gene promoter, an elastase I gene promoter, a CBA promoter, a β-actin gene promoter, a β-globin gene promoter, a γ-globin gene promoter, an α-fetoprotein gene promoter, and a muscle creatine kinase (CK) gene promoter.

In still other embodiments, the AAV comprises an AAV2 or an AAV5 capsid.

In another aspect, the disclosure provides a method of increasing the production of hyaluronic acid in both the chondrocytes and/or synoviocytes of a mammal (e.g., human or canine animal). In an embodiment, the method may comprise the steps of administering the recombinant AAV ("rAAV") comprising a rAAV vector genome, wherein the rAAV vector genome comprises nucleic acid encoding a HAS2 to a mammal (e.g., human or canine), allowing sufficient time for the HAS2 enzyme to be expressed and subsequently catalyze the production of additional hyaluronic acid, thereby increasing the level of hyaluronic acid in the mammal.

The disclosure also provides a method of increasing the production of a lubricin polypeptide in both the chondrocytes and/or synoviocytes of a mammal (e.g., human or canine animal). In an embodiment, the method may comprise the steps of administering the rAAV comprising a rAAV vector genome, wherein the rAAV vector genome comprises nucleic acid encoding a lubricin to a mammal (e.g., human or canine animal), allowing sufficient time for the lubricin to be expressed, thereby increasing the level of lubricin in the canine.

In an embodiment, the HAS2 is produced in sufficient quantity following administration of an rAAV comprising nucleic acid encoding a HAS2 to treat or prevent the symptoms of OA in a mammal (e.g., a human or a canine).

In another embodiment, the lubricin is produced in sufficient quantity following administration of an rAAV comprising nucleic acid encoding lubricin to treat or prevent the symptoms of OA in a mammal (e.g., a human or a canine).

In an embodiment, the HA levels are restored to levels found in healthy a mammal (e.g., a human or a canine). The skilled person may consult a variety of references to understand what levels of HA are found in healthy animals (e.g., Smith, G N et al. Arthritis Rheum. 1998; 41:976-985; Balazs E et al. Disorders of the Knee. Philadelphia: J B Lippincott; 1982. pp. 61-74).

In another embodiment, the lubricin levels are restored to levels found in healthy a mammal (e.g., a human or a canine).

In another aspect, the disclosure provides a method of treating a canine suffering from, or at risk of developing, OA, comprising, administering to said canine a therapeutically effective amount of an AAV vector containing a nucleic acid sequence encoding an HAS2 or lubricin polypeptide operably linked to a promoter. In another embodiment, the disclosure provides a method of treating a human suffering from, or at risk of developing, OA, comprising, administering to said human a therapeutically effective amount of an AAV vector containing a nucleic acid sequence encoding a HAS2 or lubricin polypeptide operably linked to a promoter.

In some embodiments, the nucleic acid sequence encoding the HAS2 polypeptide has at least 90% identity to the nucleic acid sequence as set forth in SEQ ID NO: 3, or the nucleic acid sequence encoding the lubricin polypeptide has at least 90% identity to the nucleic acid sequence as set forth in SEQ ID NO: 6.

In some embodiments, the AAV encodes a HAS2 polypeptide comprising an amino acid sequence set forth in SEQ ID NO: 2 or comprises an amino acid sequence at least 90% identical to the amino acid sequence set forth in SEQ ID NO: 2. In some embodiments, the AAV encodes a lubricin polypeptide comprising an amino acid sequence set forth in SEQ ID NO: 7 or comprises an amino acid sequence at least 90% identical to the amino acid sequence set forth in SEQ ID NO: 7.

In any embodiment, the promoter may be selected from a CMV IE promoter, a RSV promoter, an HSV-1 TK promoter, a SV40 early promoter, a SV40 late promoter, an adenovirus major late promoter, a phosphoglycerate kinase gene promoter, a metallothionein gene promoter, an α-1 antitrypsin gene promoter, an albumin gene promoter, a collagenase gene promoter, an elastase I gene promoter, a β-actin gene promoter, a CBA promoter, a β-globin gene promoter, a γ-globin gene promoter, an α-fetoprotein gene promoter, and a muscle creatine kinase gene promoter.

In another aspect, the disclosure provides a method of preventing the development of OA in a mammalian subject at risk thereof, comprising, administering to said canine a prophylactically effective amount of a rAAV comprising a rAAV vector genome comprising a nucleic acid sequence encoding a HAS2 or lubricin polypeptide operably linked to a promoter. In an embodiment, the nucleic acid sequence encoding the HAS2 polypeptide has at least 90% identity to the nucleic acid sequence as set forth in SEQ ID NO: 3, or the nucleic acid sequence encoding the lubricin polypeptide has at least 90% identity to the nucleotide sequence set forth in SEQ ID NO: 6. In another embodiment, the nucleic acid encodes a HAS2 polypeptide comprising the amino acid sequence set forth in SEQ ID NO: 2, or the nucleic acid encodes a lubricin polypeptide comprising the amino acid sequence set forth in SEQ ID NO: 7. In an embodiment, the promoter may be selected from the group consisting of a CMV IE promoter, a RSV promoter, an HSV-1 TK promoter, a SV40 early promoter, a SV40 late promoter, an adenovirus major late promoter, a phosphoglycerate kinase gene promoter, a metallothionein gene promoter, an α-1 antitrypsin gene promoter, an albumin gene promoter, a collagenase gene promoter, an elastase I gene promoter, a β-actin gene promoter, a β-globin gene promoter, a γ-globin gene promoter, an α-fetoprotein gene promoter, and a muscle creatine kinase gene promoter. In some embodiments, the rAAV vector comprises CBA-cHAS2co-BGH. In other embodiments, the rAAV vector comprises pITR/minCBA-HIb-cLub1co-BGH.

In another aspect, the disclosure provides a recombinant plasmid vector comprising a nucleic acid sequence encoding a canine HAS2 or lubricin polypeptide operably linked to a promoter. In some embodiments, the nucleic acid sequence encoding the HAS2 polypeptide has at least 90% identity to the nucleic acid sequence set forth in SEQ ID NO: 3, or the nucleic acid sequence encoding the lubricin polypeptide has at least 90% identity to the nucleic acid sequence set forth in SEQ ID NO: 6. In a some embodiments, the nucleic acid encodes a HAS2 polypeptide comprising the amino acid sequence set forth in SEQ ID NO: 2, or the nucleic acid encodes a lubricin polypeptide comprising the amino acid sequence set forth in SEQ ID NO: 7.

In an aspect, the disclosure provides a pharmaceutical composition comprising a recombinant viral vector encoding and expressing in vivo in a mammalian host HAS or lubricin, and optionally one or more pharmaceutically acceptable carrier, excipient, or vehicle.

In another aspect, the disclosure provides a method of treating a mammalian subject suffering from, or at risk of developing, osteoarthritis, comprising, intra-articularly administering to said mammalian subject a therapeutically effective amount of the above-detailed pharmaceutical compositions. In an embodiment, the subject is human or canine.

In another aspect, the disclosure provides an adeno-associated virus (AAV)-based biological delivery and expression system for use in the treatment or prevention of OA in human or mammalian joints. In some embodiments, the method is accomplished by long-term gene expression of human or mammalian HAS2 or lubricin in synovial and/or chondrocyte cells, following delivery of rAAV comprising a nucleic acid sequence encoding human or mammalian HAS2 or lubricin, left and right AAV inverted terminal repeats (L ITR and R ITR), the AAV packaging signal and optionally non-viral, non-coding stuffer nucleic acid sequences. In some embodiments, the expression of the human or mammalian HAS2 or lubricin gene within synovial and/or chondrocyte cells is regulated by an inflammation-inducible promoter, which is located upstream of the reading frame of the nucleic acid sequence encoding for human or mammalian HAS2 or lubricin and which is specifically activated by increased levels of immune stimulatory substances.

In some embodiments, the inflammation-inducible promoter is selected from the following: an NF-KB promoter, an interleukin 6 (Il-6) promoter, an interleukin-1 (11-1) promoter, a tumor necrosis factor (TNF) promoter, a cyclooxygenase 2 (COX-2) promoter, a complement factor 3 (C3) promoter, a serum amyloid A3 (SAA3) promoter, a macrophage inflammatory protein-1a (MIP-1a) promoter and hybrid constructs thereof. In some embodiments, the rAAV vector genome comprises a nucleic acid sequence set forth in SEQ ID NO: 3, SEQ ID NO: 6, or a biologically effective variant thereof. In some embodiments, the AAV system comprises nucleic acid encoding a marker gene that allows monitoring of the vector genome in the synovial and chondrocyte cells. In some embodiments, the vector comprises a nucleic acid sequence set forth in SEQ ID NO: 3, SEQ ID NO: 6 or a conserved sequence thereof encoding for the same amino acids. In some embodiments, the rAAV vector genome comprises nucleic acid encoding the HAS2 polypeptide set forth in SEQ ID NO: 2 or the lubricin polypeptide set forth in SEQ ID NO: 7. The rAAV vector genome may comprise a nucleic acid molecule having at least 80% or 90% sequence identity with the nucleic acid sequence set forth in SEQ ID NO: 3. In other embodiments, the rAAV vector genome comprises a nucleic acid molecule having at least 80% or 90% sequence identity with the nucleic acid sequence set forth in SEQ ID NO: 6.

In some embodiments of the AAV system, the system comprises a nucleic acid sequence encoding for human or mammalian HAS2 or lubricin, left and right AAV inverted terminal repeats (L ITR and R ITR), a packaging signal and optionally non-viral, non-coding stuffer nucleic acid sequences, wherein the expression of the human or mammalian HAS2 or lubricin gene within synovial and/or chondrocyte cells is regulated by an inflammation-inducible promoter, which is specifically activated by increased levels of immune stimulatory substances, for the treatment or prevention of osteoarthritis (OA).

Viral Particles and Methods of Producing Viral Particles

Also provided herein are viral particles comprising a nucleic acid encoding a HAS2 or lubricin. Viral vectors can be used for delivery of a nucleic acid encoding a HAS2 or lubricin for expression of the protein in a target cell within a particular location (e.g., a joint). Many species of virus are known, and many have been studied for purposes of delivering nucleic acids to target cells. The exogenous nucleic acid can be inserted into a vector such as an adeno-associated virus (AAV), In some embodiments, the viral particle is a recombinant AAV particle comprising a nucleic acid comprising one or two AAV ITRs and a sequence encoding a HAS2 or lubricin described herein flanked by one or two ITRs. The nucleic acid is encapsidated in the AAV particle. The AAV particle also comprises capsid proteins. In some embodiments, the nucleic acid comprises operatively linked components in the direction of transcription, control sequences including transcription initiation and termination sequences, and the protein coding sequence(s) of interest (e.g., nucleic acid encoding a fusion protein). These components are flanked on the 5' and 3' end by functional AAV ITR sequences. By "functional AAV ITR sequences" it is meant that the ITR sequences function as intended for the rescue, replication and packaging of the AAV virion. See Davidson et al., *PNAS*, 2000, 97(7)3428-32; Passini et al., *J. Virol.*, 2003, 77(12):7034-40; and Pechan et al., *Gene Ther.*, 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, Hum. *Gene Ther.*, 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., *PNAS*, 2002, 99(18): 11854-6; Gao et al., *PNAS*, 2003, 100(10):6081-6; and Bossis et al., *J. Virol.*, 2003, 77(12):6799-810. Use of any AAV serotype is considered within the scope of the present invention. In some embodiments, a rAAV vector is a vector derived from an AAV serotype, including without limitation, AAV1, AAV2, AAV3, AAV4, AAV5, AA6, AAV7, AAV8, AAV9, AAVrh.8, and AAVrh.10. In some embodiments, the nucleic acid in the AAV comprises an ITR of AAV1, AAV2, AAV3, AAV4, AAV5, AAV6, AAV7, AAV8, AAV9, AAVrh.8, or AAVrh.10. In further embodiments, the rAAV particle comprises capsid proteins of AAV1, AAV2, AAV3, AAV4, AAV5, AA6, AAV7, AAV8, AAV9, AAVrh.8, or AAVrh.10.

Different AAV serotypes are used to optimize transduction of particular target cells or to target specific cell types within a particular target (e.g., a joint). A rAAV particle can comprise viral proteins and viral nucleic acids of the same serotype or a mixed serotype. For example, a rAAV particle can comprise AAV2 capsid proteins and at least one AAV2 ITR or it can comprise AAV2 capsid proteins and at least one AAV5 ITR. In another example, a rAAV particle can comprise AAV5 capsid proteins and at least one AAV2 ITR. Any combination of AAV serotypes for production of a rAAV particle is provided herein as if each combination had been expressly stated herein.

The rAAV particles can be produced using methods know in the art. See, e.g., U.S. Pat. Nos. 6,566,118, 6,989,264, 6,995,006. In practicing the invention, host cells for producing rAAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV vectors are purified and formulated using standard techniques known in the art.

In some aspects, a method is provided for producing any rAAV particle as disclosed herein comprising (a) culturing a host cell under a condition that rAAV particles are produced, wherein the host cell comprises (i) one or more AAV package genes, wherein each said AAV packaging gene encodes an AAV replication or encapsidation protein; (ii) an rAAV pro-vector comprising a nucleic acid encoding any fusion protein disclosed herein flanked by at least one AAV ITR, and (iii) an AAV helper function; and (b) recovering the rAAV particles produced by the host cell. In some embodiments, said at least one AAV ITR is selected from the group consisting of AAV1, AAV2, AAV3, AAV4, AAV5, AA6, AAV7, AAV8, AAV9, AAVrh.8, and AAVrh.10 ITR. In some embodiments, said encapsidation protein is selected from the group consisting of AAV1, AAV2, AAV3, AAV4, AAV5, AA6, AAV7, AAV8, AAV9, AAVrh.8, and AAVrh.10 capsid protein. In a further embodiment, the rAAV particles are purified. The term "purified" as used herein includes a preparation of rAAV particles devoid of at least some of the other components that may also be present where the rAAV particles naturally occur or are initially prepared from. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) present in a solution, or by infectivity, or it can be measured in relation to a second, potentially interfering substance present in the source mixture, such as contaminants, including production culture contaminants or in-process contaminants, including helper virus, media components, and the like.

Also provided herein are pharmaceutical compositions comprising a rAAV particle comprising a nucleic acid encoding HAS2 or lubricin of the invention and a pharmaceutically acceptable carrier. The pharmaceutical compositions may be suitable for a variety of modes of administration described herein, including for example systemic or localized administration. A pharmaceutical composition of a rAAV comprising a nucleic acid encoding HAS2 or lubricin described herein can be introduced systemically, e.g., by intravenous injection, by catheter, see U.S. Pat. No. 5,328, 470, or by stereotactic injection, Chen et al., 1994, PNAS, 91: 3054-3057. In some embodiments, the pharmaceutical compositions comprising a rAAV described herein and a pharmaceutically acceptable carrier is suitable for administration to human. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

REFERENCES

All publications, patents, and patent applications cited herein are hereby incorporated by reference in their entirety for all purposes.

Aalbers C J et al. 2015. Preclinical potency and biodistribution studies of an AAV vector expressing human interferon-b (ARTI02) for local treatment of patients with rheumatoid arthritis. PLoS One 2015, 10:e130612.

Ai, M et al. Anti-lubricin monoclonal antibodies created using lubricin-knockout mice immunodetect lubricin in several species and in patients with healthy and diseased joints. PLOS 2015. 10:e0116237

Apparailly F et al. Adeno-associated virus pseudotype 5 vector improves gene transfer in arthritic joints. Hum Gene Ther 2005; 16: 426-434.

Asokan A, Smulski R J. 2012. The AAV vector toolkit: poised at the clinical crossroads. Molecular Therapy 20:699-708.

Blewis M E et al. 2007. A model of synovial fluid lubricant composition in normal and injured joints. European Cells and Materials 13:26-39.

Calcedo R et al. 2015. Preexisting neutralizing antibodies to adeno-associated virus capsids in large animals other than monkeys may confound in vivo gene therapy studies. Human Gene Therapy Methods 26:103-105.

Clark, K R et al. (1999). Highly purified recombinant adeno-associated virus vectors are biologically active and free of detectable helper and wild-type viruses Hum Gene Ther 10: 1031-1039.

David-Raoudi M et al. Chondroitin sulfate increases hyaluronan production by human synoviocytes through differential regulation of hyaluronan synthases. Arthritis & Rheumatism 2009, 60:760-770.

Elsaid K A et al. Decreased lubricin concentrations and markers of inflammation in the synovial fluid of patients with anterior cruciate ligament injury. Arthritis & Rheumatism 2008, 58:1707-1715.

Evans C H et al. 2009. Gene therapy of the rheumatic diseases: 1998 to 2008. Arthritis Research Therapy 11:209

Evans C H et al. 2009. Progress and Prospects: genetic treatments for disorders of bones and joints. Gene Therapy 16:944-952.

Flannery C R et al. Prevention of cartilage degeneration in a model of osteoarthritis by intraarticular treatment with recombinant lubricin. Arthritis & Rheumatism 2009, 60:840-847.

Flannery et al. 1999: Articular cartilage superficial zone protein (SZP) is homologous to megakaryocyte stimulating factor precursor and is a multifunctional proteoglycan with potential growth-promoting, cytoprotective, and lubrication properties in cartilage metabolism. Biochem Biophys Res Comm, 254:535-41

Goodrich L R et al. 2013. Optimization of scAAVIL-1ra in vitro and in vivo to deliver high levels of therapeutic protein for treatment of osteoarthritis. Molecular Therapy-Nucleic Acids 2:e70.

Guo N et al. A rapid increase in hyaluronan synthase-2 mRNA initiates secretion of hyaluronan by corneal keratocytes in response to transforming growth factor beta. J Biol Chem 2007, 282:12475-83.

Hemphill D D et al. 2014. Adeno-associated viral vectors show serotype specific transduction of equine joint tissue explants and cultured monolayers. Scientific Reports 4:5861-5868.

Hunter D J, Matthews G. Emerging drugs for osteoarthritis. 2011. Expert Opin Emerg Drugs 16:479-491.

Hurlbut G D et al. 2010. Preexisting immunity and low expression in primates highlight translational challenges for liver-directed AAV8-mediated gene therapy. Molecular Therapy 18:1983-1994.

Hyc A et al. Pro- and anti-inflammatory cytokines increase hyaluronan production by rat synovial membrane in vitro. Intern J Molec Medicine 2009, 24:579-585.

Itano N et al. 1999. Three isoforms of mammalian hyaluronan synthases have distinct enzymatic properties. JBC 1999, 274:25086-92.

Itano N et al. 1999. Three isoforms of mammalian hyaluronan synthases have distinct enzymatic properties. JBC 1999, 274:25086-92.

Keiser N W et al., Engelhardt. 2011. Unique characteristics of AAV1, 2, and 5 viral entry, intracellular trafficking and nuclear import define transduction efficiency in HeLa cells. Hum Gene Ther 22:1433-1444.

Kwiecinski et al. 2011: The effect of molecular weight on hyaluronan's cartilage boundary lubricating ability—alone and in combination with proteoglycan 4. Osteoarthritis Cartilage 19:1356-62.

Kyostio-Moore S et al. 2015. Over-expression of cystatin C in synovium does not reduce synovitis or cartilage degradation in established osteoarthritis. Arthritis Res Ther 17:5-21.

S. Kyostio-Moore et al. Local gene delivery of heme oxygenase-1 by adeno-associated virus into osteoarthritic mouse joints exhibiting synovial oxidative stress. Osteoarthritis and Cartilage Volume 21, Issue 2, February 2013, Pages 358-367.

Lee H H et al. Persistence, localization, and external control of transgene expression after single injection of adeno-associated virus into injured joints. Hum Gene Ther 2013, 24:457-466.

Li P et al. Hylan G-F 20 maintains cartilage integrity and decreases osteophyte formation in osteoarthritis through both anabolic and anti-catabolic mechanisms. Osteoarthritis Cartilage 2012, 20:1336-46.

Loeser R F. Osteoarthritis year in review 2013: biology. Osteoarthritis and Cartilage, 21:1436-1442.

Mease P J et al. 2009. Local delivery of a recombinant adeno-associated vector containing a tumor necrosis factor alpha antagonist gene in inflammatory arthritis: a Phase 1 dose-escalation safety and tolerability study. Ann Rheum Dis 68:1247-1254.

Mietzsch M et al. 2014. Differential adeno-associated virus serotype-specific interaction patterns with synthetic heparins and other glycans. J Virology 88:2992-3003.

Miltner O et al. Efficacy of intraarticular hyaluronic acid in patients with osteoarthritis—a prospective clinical study. Osteoarthritis Cartilage 2002, 10:680-6.

Mingozzi F et al. 2013. Prevalence and pharmacological modulation of humoral immunity to AAV vectors in gene transfer to synovial tissue. Gene Therapy 20:417-424.

Momberger T S et al. Hyaluronan secretion by synoviocytes is mechanosensitive. Matrix Biology 2005, 24:510-519.

Nishida Y et al. Antisense inhibition of hyaluronan synthase-2 in human articular chondrocytes inhibits proteoglycan retention and matrix assembly. JBC 1999, 274:1893-21899.

Ortved K F et al. Implantation of rAAV5-IGF-I transduced autologous chondrocytes improves cartilage repair in full-thickness defects in the equine model. Mol Ther 2015, 23:363-373.

Payne K A et al. Single intra-articular injection of adeno-associated virus results in stable and controllable in vivo transgene expression in normal rat knees. Osteoarthritis Cartilage 2011, 19:1058-1065.

Plickert H D et al. Hyaluronic acid concentrations in synovial fluid of dogs with different stages of osteoarthritis. Research in Veterinary Science 2013, 94:728-734.

Rapti K et al. 2012. Neutralizing antibodies against AAV serotypes 1, 2, 6, and 9 in sera of commonly used animal models. Molecular Therapy 20:73-83.

Rhee D K et al. Consequences of disease-causing mutations on lubricin protein synthesis, secretion, and post-translational processing. JBC 2005, 280:3125-3132.

Ryan M Z C et al. Proteoglycan 4 expression protects against the development of osteoarthritis. Sci Transl Med 2013, 5:176ra34.

Sarzi-Puttini P et al. Osteoarthritis: an overview of the disease and its treatment strategies. Semin. Arthritis Rheum 2005, 35:1-10.

Schmid T et al. 2001. Superficial zone protein (SZP) is an abundant glycoprotein in human synovial fluid and serum. Trans Orthop Res Soc 26:82.

Sharkey M. The challenges of assessing osteoarthritis and postoperative pain in dogs. 2013. The AAPS Journal 15:598-607

Vugmeyster Y et al. Disposition of human recombinant lubricin in naïve rats and in a rat model of post-traumatic arthritis after intra-articular or intravenous administration. AAPS J 2012, 14:97-104.

Waller K A et al. Role of lubricin and boundary lubrication in the prevention of chondrocyte apoptosis. PNAS 2013.

Watanabe K and Yamaguchi Y. Molecular identification of a putative human hyaluronan synthase. JBC 1996, 271: 22945-48

Watanabe, S et al. Adeno-associated virus mediates long-term gene transfer and delivery of chondroprotective IL-4 to murine synovium. Molecular Ther 2000; 2: 147-151.

Watson R S et al. scAAV-mediated gene transfer of interleukin-1-receptor antagonist to synovium and articular cartilage in large mammalian joints. Gene Therapy 20:670-677.

Yoshida M et al. Expression analysis of three isoforms of hyaluronan synthase and hyaluronidase in the synovium of knees in osteoarthritis and rheumatoid arthritis by quantitative real-time reverse transcriptase polymerase chain reaction. Arthritis Research Therapy 2004, 6:R514-R520.

EXAMPLES

Example 1—HAS2 AAV Vector Construction and Evaluation

Example 1a—Overview rAAV vectors containing codon-optimized canine HAS2 cDNA and a ubiquitous promoter were generated and packaged into AAV2 or AAV5 capsids. Large-scale vector lots were generated by triple transfection method and purified by CsCl gradient. Vector yields were quantitated by qPCR to the bovine growth hormone (BGH) polyA site (pA). A total of 4 lots were generated for AAV2/HAS2 (of which 3 were pooled for in vivo studies, $2 \times 10^{13}$ DRP/total). Two lots were generated for AAV5/HAS2 ($5 \times 10^{12}$ DRP/total) to test consistency of production yields and obtain sufficient amount of virus.

Twenty-two adult healthy dogs, seronegative for AAV2 and AAV5 capsids, received rAAV2 (1, 5 and $10 \times 10^{11}$ vg/joint), rAAV5 ($5 \times 10^{11}$ vg/joint) or PBS (control) via intra-articular injection. No adverse clinical signs were observed following the 28-day study. Histopathological analysis showed minimal synovial inflammation in joints treated with rAAV5 and no significant changes in the rAAV2 treatment groups. Vector genomes (VG) were detected in the synovium of all the rAAV-treated joints and in the majority of cartilage samples. The rAAV5 vectors resulted in higher VG detection and mRNA expression compared to rAAV2 in both tissues. A trend of increased HA levels in the synovial fluid of the treated joints was noted. In summary, the disclosed results demonstrated gene transfer to canine joint tissues and an acceptable safety profile with rAAV2 and rAAV5 vectors encoding HAS2 when administered by single intra-articular injection to canines.

Example 1b—Methods

Cloning and generation of HA expression vector. Canine HAS2 gene (GenBank XM 539153.3; SEQ ID NO: 1) was codon-optimized for expression in canines by algorithm from GeneArt/Invitrogen. The codon-optimized canine HAS2 cDNA (1656 bp; SEQ ID NO:3) was synthesized with flanking NheI-NsiI restriction enzyme sites This fragment was then cloned into a plasmid containing ubiquitous chicken b-actin promoter (CBA), a hybrid intron and a bovine growth hormone (BGH) polyA (pA). The resulting pCBA-HI-cHAS2-BGHpA plasmid was purified using maxi kit (Qiagen) for expression analyses.

Expression of cHAS2 in vitro and production of HA. A plasmid vector containing cHAS2 was transfected into 293 cells and the conditioned media and cell lysates were collected into 250 µl of RIPA buffer plus protease inhibitors 3 days later. Cell lysates were spun to remove cell debris and 30 µl of the cell lysate was loaded on a 4-12% nu-page gel and run in 1× Mops buffer. The protein gel was transferred to a nitrocellulose membrane and probed with anti-HAS2 (se-34-068; Santa Cruz Biotechnology) in 5% milk in PBS-T 0.1% tween-20 overnight at 4° C. A donkey anti-goat secondary antibody (at 1:5000 dilution) was used as secondary antibody. Beta actin detection was used to show equal loading of cell lysates.

Quantitation of HA levels and molecular weight in vitro cultures. The production of HA by HAS2 expressing cells was evaluated by transfecting pCBA-HI-cHAS2-BGHpA into 293 cells (in Optimem or complete medium). The conditioned media was quantitated for HA levels using HA test kit (Corgenix, Inc.). This kit contains a HA-binding protein derived from aggrecan. The molecular weight of HA was assessed by running concentrated conditioned media on agarose gel. Various HA size markers were run in parallel (Select-HA HiLadder, Hyalose, Austin, TX). A similar gel was run in parallel followed by digestion of hyaluronidase for 24 h. Both gels were stained with All-stain.

Generation of rAAV vector with cHAS. The cHAS2 expression cassette was cloned into a AAV ITR-containing plasmid to generate expression cassette flanked by AAV inverted terminal repeats (pre-viral plasmid pDC627) to construct psITR/CBA-HI-cHAS2-BGHpA. A 600 bp stuffer DNA (chromosome 16 P1 clone 96.4B) was included upstream of expression cassette to generate viral vector genome of 4500 bp total. To test packaging of the cHAS2 expression cassette containing plasmid, 293 cells were seeded at $8 \times 10^5$ cells/well (6-well plates) and the following day transfected with psITR/CBA-HI-cHAS2-BGHpA, or psp70/EGFP, pHLP-19cap2 or p5repCMVcap5 plasmids and pAdHELP in duplicates (Promega CaPO$_4$ kit). Cells were collected 3 days later and the lysates were titered for BGHpA copies using qPCR analysis and primer/probe to BGHpA sequences (SEQ ID NOs:12-14). A plasmid containing BGHpA was used as a standard. The rAAV virus yields were expressed as amount of DNase resistant particles (DRP) per cell. Large scale vector production was performed using triple transfection of psITR/CBA-HI-cHAS2-BGH, pIM45BD rep-cap plasmid for AAV2 vectors and pHLP19-cap5 for AAV5 vectors, and pAdHELP. The vector was purified by CsCl and resulting vector lot titered using TaqMan analysis and primer/probe to BGHpA sequences (Applied Biosystems/Life Technologies).

Efficacy of rAAV/cHAS2 in rabbit chondrocytes and synoviocytes in vitro. The ability of the vector to transduce joint cell types such as primary synoviocytes and chondrocytes was tested using rabbit cells. The cells were infected with 1 e5 DRP/cell and cultured for 3 days. The cell lysates were collected for HAS2 protein detection by Western blot and culture media was quantitated for HA levels as described above. To test the effect of HA production on matrix degrading proteases, inflammatory cytokines and cartilage structural protein production in disease conditions, the cells were first infected with rAAV vectors followed by IL-1b stimulation 24 h later. After 24 h, both cells and culture media were collected for mRNA analysis and HA production.

rAAV/cHAS2 evaluation in normal canine joints. Mixed breed dogs were used (male and females, 8-10 kg). Canines with serum titer of <4 or 4 to AAV2 and/or AAV5 capsids were used for the study. rAAV2 and AAV5 vectors encoding for cHAS2 were administered (AAV2: 1, 5 and $10 \times 10^{11}$, AAV5, $5 \times 10^{11}$ DRP/joint) by intra-articular route. PBS was used as negative control. Animals were observed for clinical signs (pain, lameness, swelling of the injected joint and other abnormalities) once daily for 7 days prior to injections, twice daily for 7 days after injection and then once daily for the duration of the study. Animals were sacrificed 4 weeks later. Whole blood samples were collected −7, 1, 14 and 28 days after vector administration for white blood cell (WBC) counts. Synovial fluid (SF) samples were collected on days −7, day 14 and day 28 for quantitation of HA levels. Synovial tissue, cartilage and liver samples were collected for DNA and RNA isolation. cHAS2 vector genome and mRNA copies were determined by qPCR analysis using BGHpA primer/probe sets (Applied Biosystems/Life Technologies). For histological analysis, the medial side of the knee (tibia, femur, synovium) was embedded in paraffin and sectioned. Sections were stained with toluidine blue and examined by a board certified veterinary pathologists. Cartilage was evaluated for severity of cartilage lesions and proteoglycan loss (scoring: 0-5). Synovial pathology was scored for density of inflammatory cells (scoring: 0-5) as no synovial thickening was observed.

Example 1c—Results

Codon-optimization and generation of HAS2 expression cassette. Mammalian HAS2 is a highly conserved protein. For example, the human and canine amino acid sequence for HAS2 contains only 2 amino acid differences (99.3% identity). Similarly, only 3 amino acids are different between canine and rabbit HAS2 (99.5%). At the DNA level, the similarity between canine and human HAS2 synthase cDNA is 93.9%. As codon-optimization can improve by gene expression, the canine HAS2 GenBank sequence (XM 539153.3) was optimized by GeneArt/Invitrogen. This resulted in a nucleotide sequence having 78% similarly to the original GenBank sequence. The GC content of the optimized cDNA was increased from 44.4% to 59.0%. This cDNA was used to generate ubiquitous expression plasmid with a CBA promoter to allow constitutive expression of HAS2 unlike to endogenous promoter (FIG. 1A). The CBA promoter is less influenced by various pro- and anti-inflammatory cytokines.

Figure 1B:
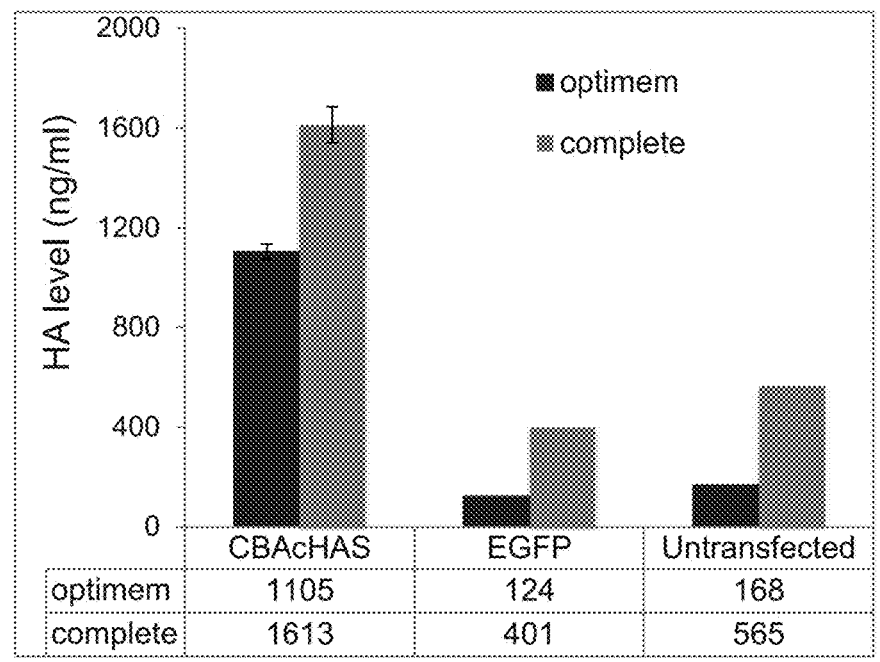
FIG. 1B is a graph showing production of HA from cells transfected with cHAS2 expression plasmid. The cHAS expression plasmid was transfected into 293 cells and conditioned media harvested 3 days later and HA levels in the media were quantitated using an HA-binding protein-based detection system. Abbreviations: CBAcHAS2, HAS2 expression plasmid. EGFP, EGFP expression plasmid. untransfected, negative control cells. "Optimem"=cells grown in serum-free media. "Complete"=cells grown in serum-containing media.
Figure 1C:
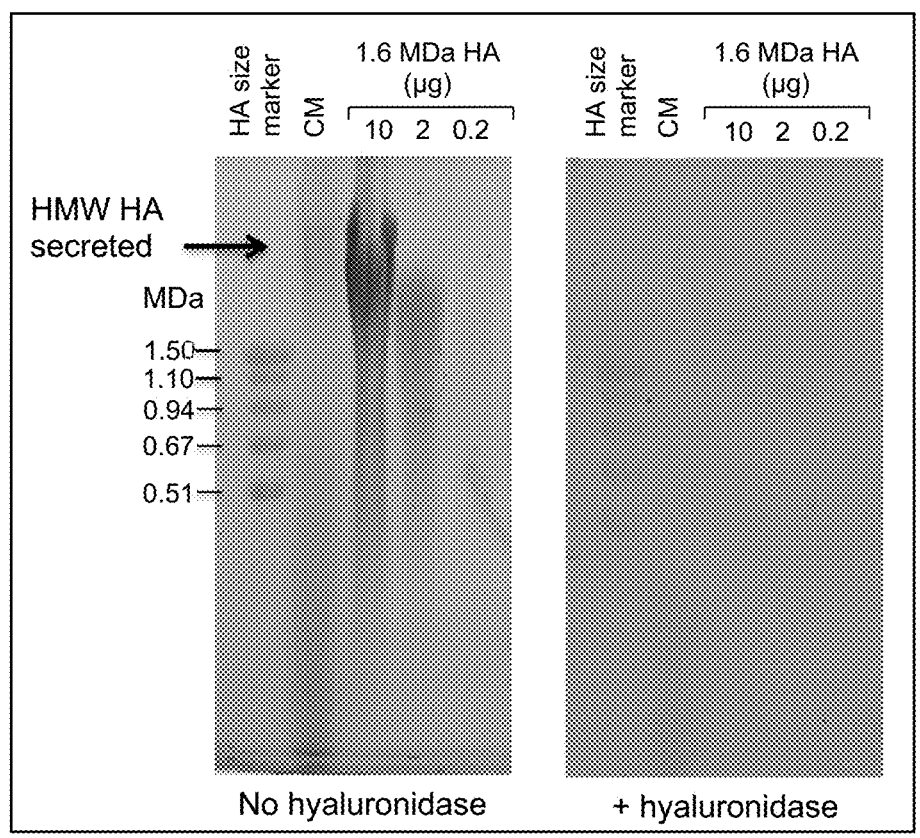
FIG. 1C are images of agarose gels used to separate components of conditioned media from the cHAS-transfected 293 cells (+ or − hyaluronidase treatment for 24 h), confirming expression of HA. Abbreviations: CM, conditioned media. MDa, molecular weight size or markers.

HAS2 expression and HA production in vitro. To test the expression of HAS2 protein in vitro, 293 cells were transfected with two clones (#1 and 2) of CBA-HI-cHAS2-BGHpA plasmid vectors followed by analysis of cell lysates for HAS2 protein (a membrane protein) by Western blot. Cells transfected with the expression plasmid showed a band at 64 kDa that is the expected size of cHAS (not shown). We next evaluated whether over-expression of HAS2 protein in 293 cells resulted in increased detection of HA in the culture media indicating both production and secretion of HA across the cell membrane. The HA levels in media from cells transfected with pCBA-cHAS2 were increased by 6.5- and 9-fold compared to untransfected and CBA-EGFP transfected cells, respectively (FIG. 1B). The data thus confirmed that over-expression of cHAS2 in cells resulted in increased HA levels in the extracellular compartment. The size of HA produced in vitro was evaluated on agarose gel. The data showed a high molecular weight HA in the conditioned media obtained from cells transfected with HAS2 expression cassette. The size of this material was larger than 1.5 Mega Dalton (MDa) (based on estimation with HA molecular weight markers). This material disappeared after digestion with hyaluronidase indicating material was HA (FIG. 1C).

Figure 2A:
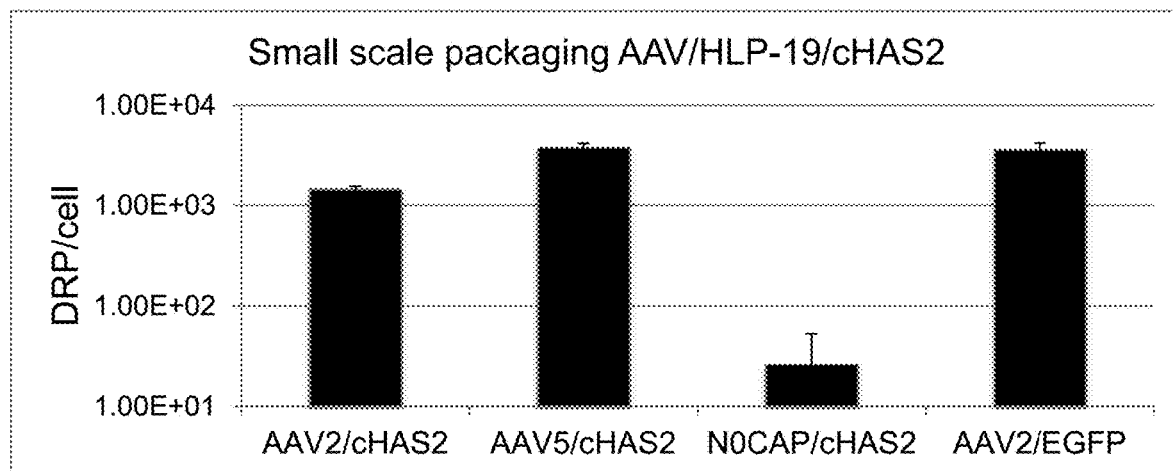
FIG. 2A is a graph showing rAAV vector production from a small-scale packaging of cHAS2 into rAAV2 and AAV5 vectors using triple transfection method. Packaging of EGFP expression cassette into AAV2 is shown as positive control and packing of cHAS in the absence of capsid plasmid as a negative control. The rAAV yield is shown as the amount of DNA resistant particles (DRP) per cell.
Figure 2B:
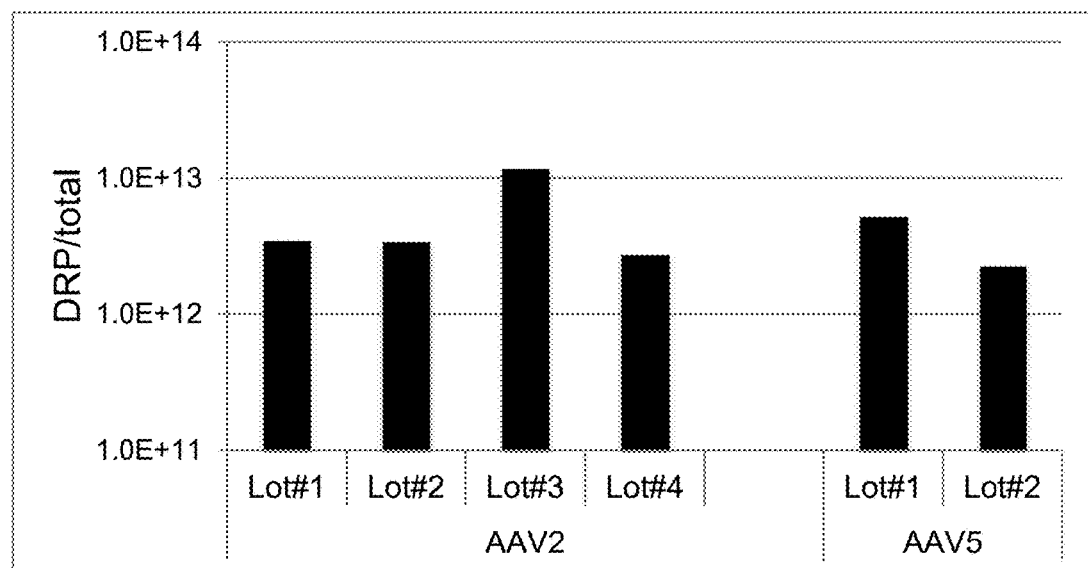
FIG. 2B is a graph showing rAAV vector yields from a large scale vector production by triple transfection. Examples of total titers obtained for multiple vector lots obtained are shown.
Figure 2C:
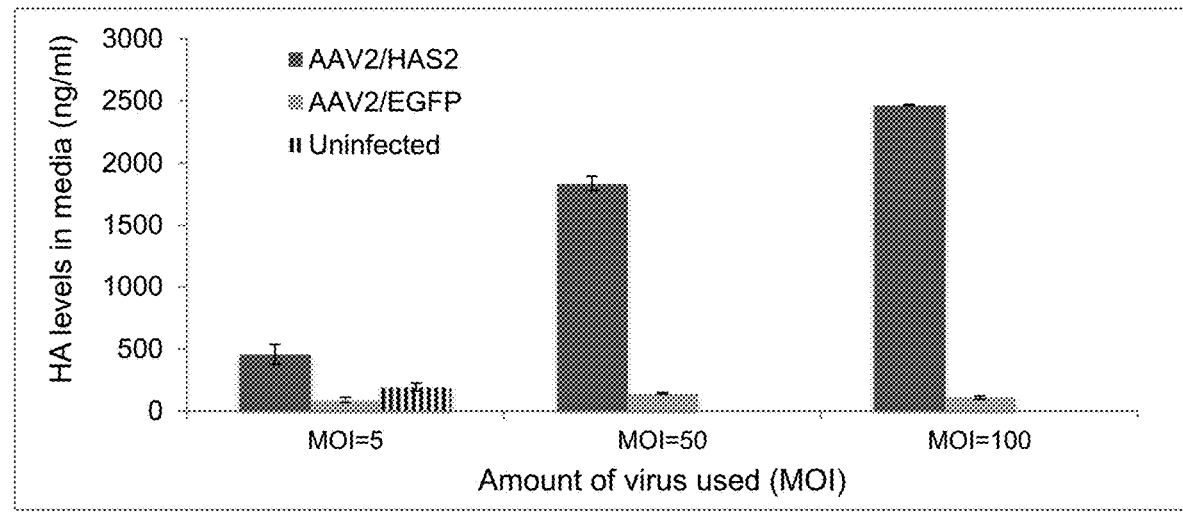
FIG. 2C is a graph showing the potency of AAV2/HAS2 vectors in vitro. The 293 cells were infected by various MOIs and HA levels in conditioned media were quantitated 3 days later.
Figure 2D:
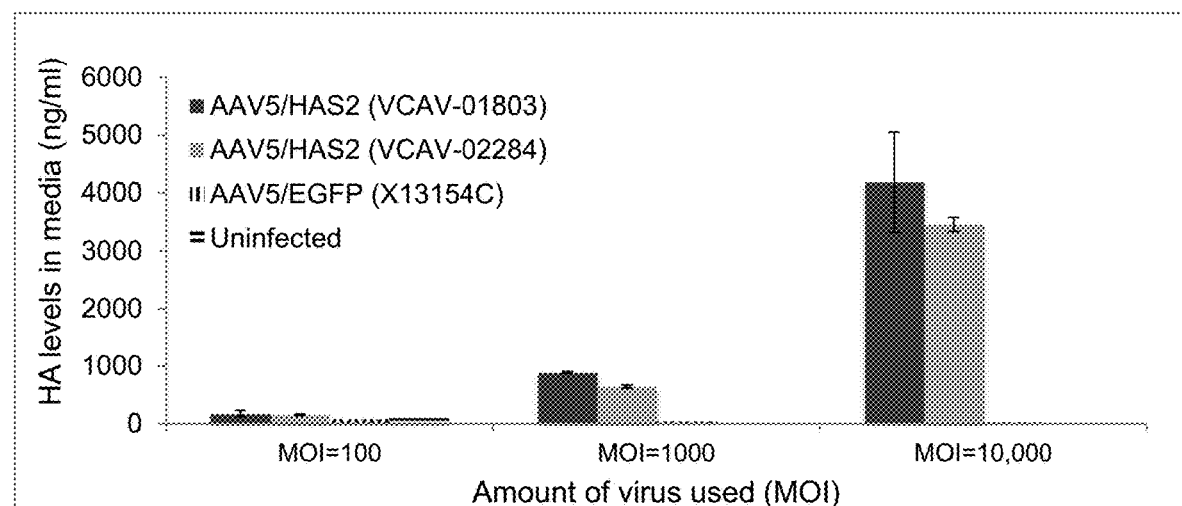
FIG. 2D is a graphs showing the potency of AAV5/HAS2 vectors in vitro.
Figure 3A:
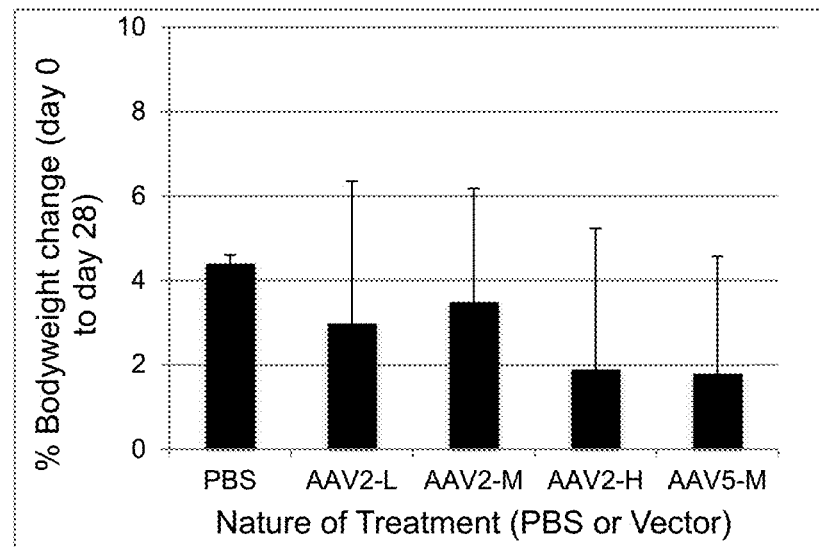
FIG. 3A is a graph showing changes in bodyweight post intra-articular injection of rAAV/HAS2 vectors in normal canine joints.
Figure 3B:
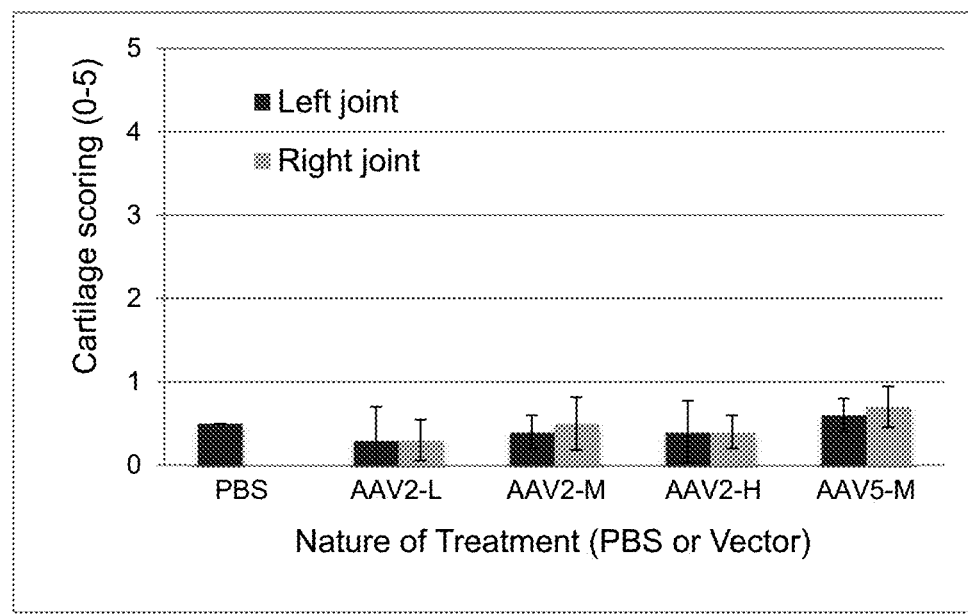
FIG. 3B is a graph showing Cartilage scoring.
Figure 3C:
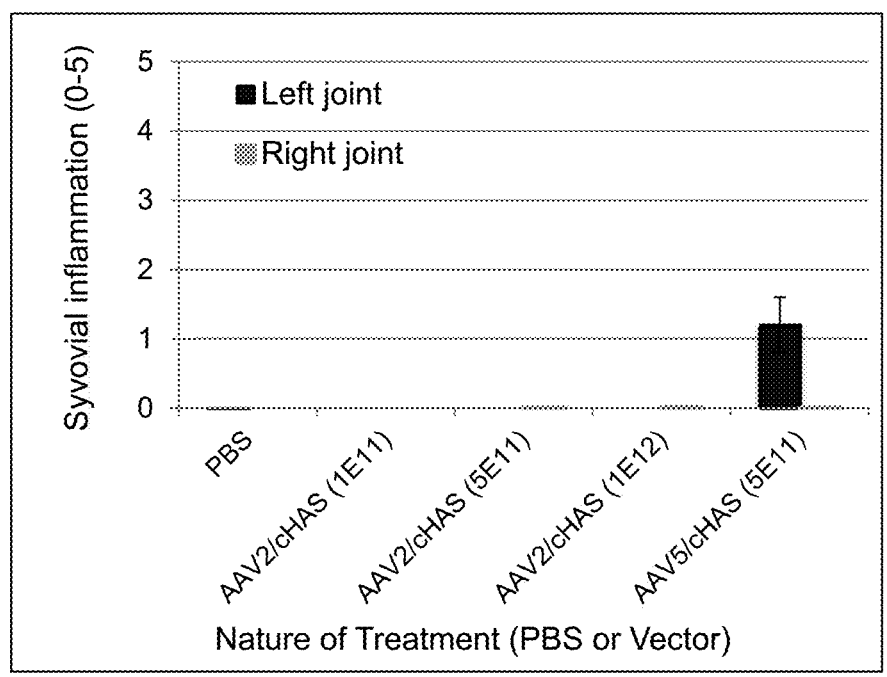
FIG. 3C is a graph showing synovial scoring.

Generation of rAAV vectors with HAS2 expression cassette. The cHAS2co expression cassette was subsequently cloned into plasmid with AAV ITRs. A schematic of the resulting viral genome is shown in FIG. 1A. The ability to generate rAAV vectors with AAV2 and AAV5 capsids and HAS2 cDNA was tested in a small-scale packaging experiment (FIG. 2A) followed by larger scale vector production. Both AAV2 and AAV5 vectors could be generated using standard triple transfection methods (FIG. 2B). The potency of this material was tested by infecting 293 cells and analyzing production of HA levels in the culture media. Both AAV2 and AAV5 vectors resulted in dose-responsive increase of HA in the culture media (FIGS. 2C, D).

rAAV/HAS2 vector evaluation+ in normal canine joint. rAAV2 and AAV5 vectors with cHAS2 were delivered into joints of normal dogs by intra-articular administration and the animals were evaluated for 28 days. No adverse clinical signs, bodyweight changes (FIG. 3A), lameness or death were observed during the study. Some animals had elevated white blood cell (WBC) counts on day–7 potentially due to stress of shipping. In general, WBC counts on Days 1, 14 and 28 were within normal limits. Histological evaluation of knees from PBS-, AAV-injected (left) and contralateral (uninjected) showed very minimal proteoglycan loss and cartilage degeneration (score range 0-0.5; maximum score 5) (FIG. 3B). These minimal changes were typical age-related spontaneous changes. Minor synovial changes were observed for PBS- and AAV2-treated and contralateral joints (FIG. 3C). Minimal to mild synovitis (generally extended into joint capsule and medial collateral ligament) were seen in all left knees of males and females treated with AAV5 vector (no synovitis observed in the contralateral joint). Thus, overall the treatment was well tolerated with little adverse effect observed.

Figure 4A:
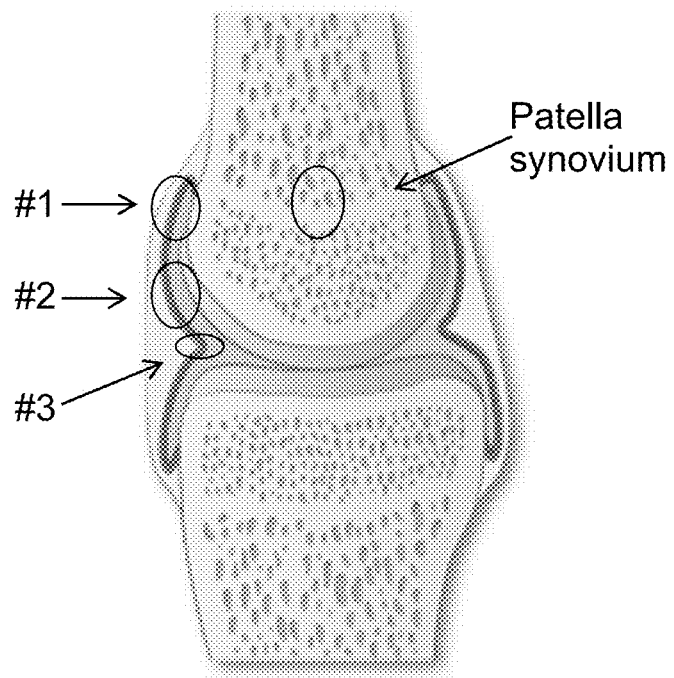
FIG. 4A is a diagram showing the locations of sample collection for the canine synovium rAAV vector quantitation.
Figure 4B:
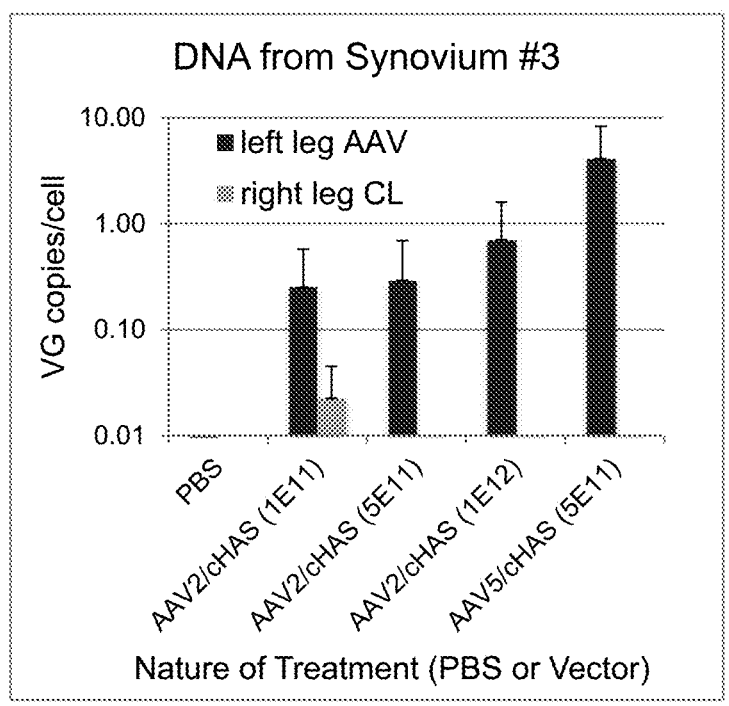
FIG. 4B is a graph showing quantitation of vector genome copies in synovial sample #3.
Figure 6A:
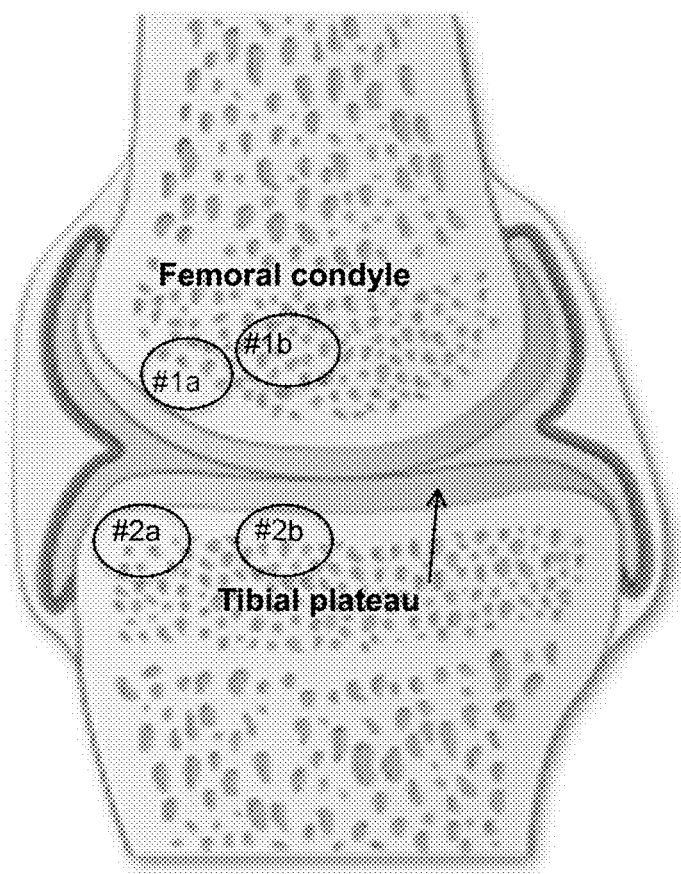
FIG. 6A is a diagram showing the locations of femoral condyle and tibial plateau samples collected to detect rAAV vector and mRNA in cartilage.

Tissue samples collected from synovium and cartilage were analyzed for detection of viral genomes (FIGS. 4A, 6A). Synovial samples collected closest to the injection site, sample #3, showed the presence of vector genomes in all of the AAV-treated joints (FIG. 4B). AAV2-treated joints contained roughly 0.01 to 2 vector genomes (VG)/cell. Interestingly, minor dose response was observed with AAV2 despite 10-fold difference between the low and high dose groups. Joints treated with AAV5 vectors showed higher and a more consistent detection with a range of 1 to 12 copies/cell. In some contralateral (un-injected) joints a low level of VGs was detected which was more pronounced in the low AAV2-treatment group and more sporadic in higher AAV2 doses and AAV5 groups (not shown).

Figure 4C:
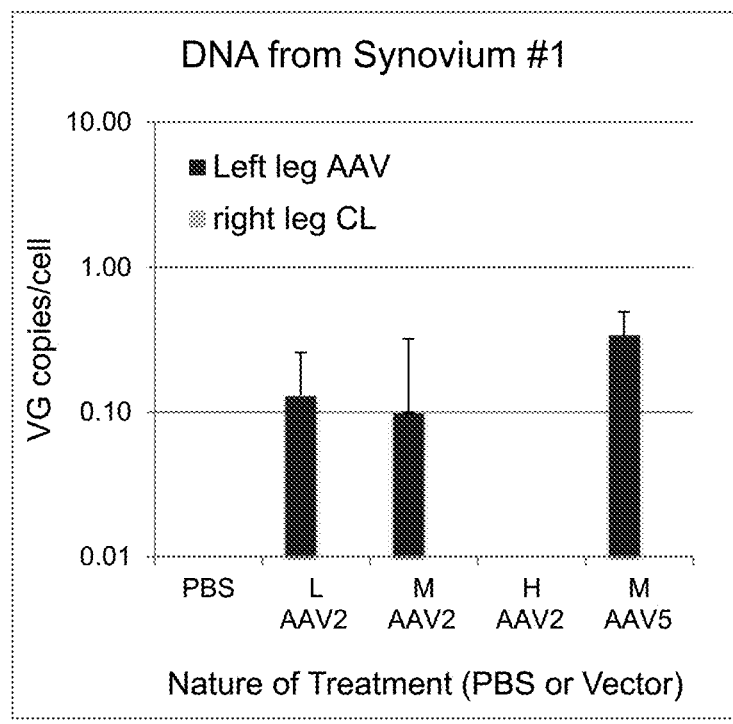
FIG. 4C is a graph showing vector genome copies in synovial sample #1. The vector dose for AAV2 and AAV5 is shown as L=low, M=medium and H=high (as in FIGS. 3A-C). All tissue samples were collected 28 days after rAAV vector delivery and analyzed by qPCR to BGHpA.

Synovium sample collected further up from the injection site, sample #1, was analyzed to evaluate AAV spread in the joint (FIG. 4C). Joints injected with AAV2 low dose showed a more consistent detection of VGs. These levels were comparable to those measured in synovium sample #3. In the AAV5 treatment group, all synovium #1 samples had consistently detectable VGs (within 3-fold). These, however, were lower than VG levels detected in synovium #3 therefore demonstration location dependent transduction.

Figure 5A:
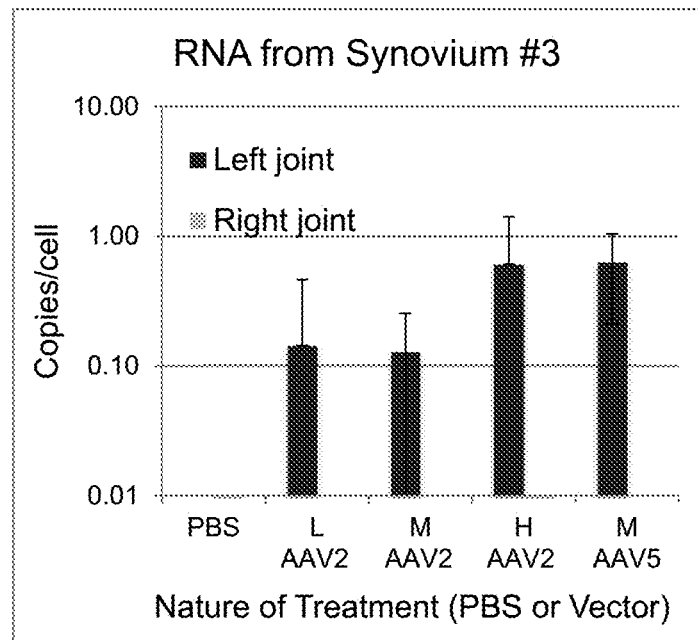
FIG. 5A is a graph showing vector derived cHAS expression in synovium sample #3.
Figure 5B:
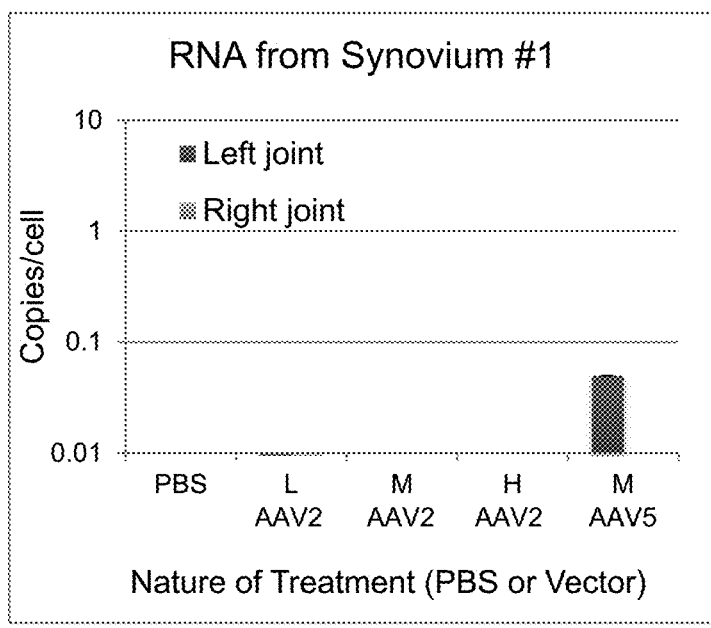
FIG. 5B is a graph showing vector mRNA in synovial sample #1.
Figure 5C:
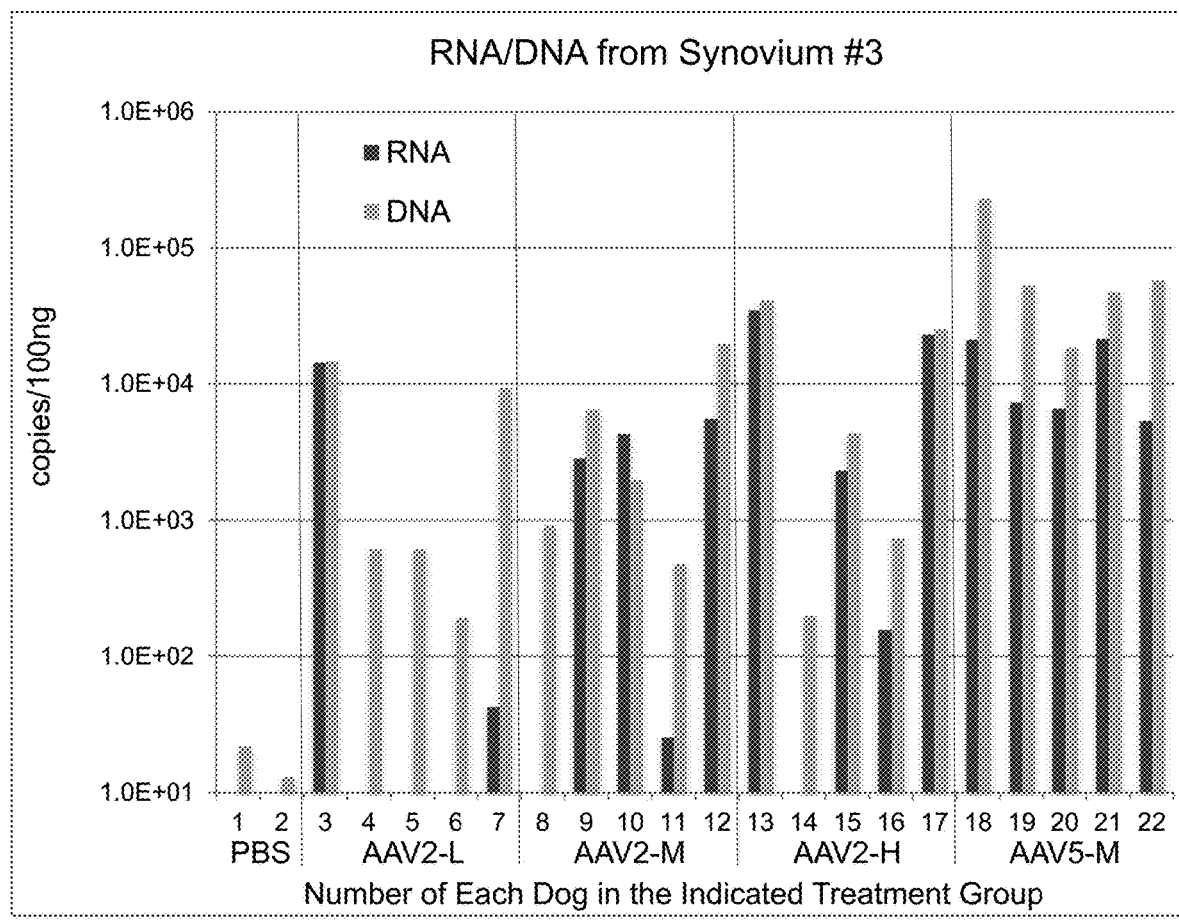
FIG. 5C is a graph showing vector genome and vector derived mRNA in each individual dog analyzed using synovial sample #3. Vector dose for AAV2 and AAV5 is shown as L=low, M=medium and H=high. All tissue samples were collected 28 days after rAAV vector delivery and analyzed by qPCR to BGHpA.

Expression from vector genome was analyzed by quantitating vector derived mRNA. For synovial sample #3, expression was detected in 2/5, 4/5 and 4/5 of the AAV2-treated low, medium and high groups while all AAV5 treated joints had detectable mRNA copies (FIG. 5A). Vector expression was also detected for AAV5 vectors in synovium #1 though the levels were lower similar to reduced detection of VGs at this location (FIG. 5B). The detection of mRNA correlated well with VG detection; the mRNA and VG DNA in each individual injected joint in synovium sample #3 is shown as an example (FIG. 5C).

Figure 6B:
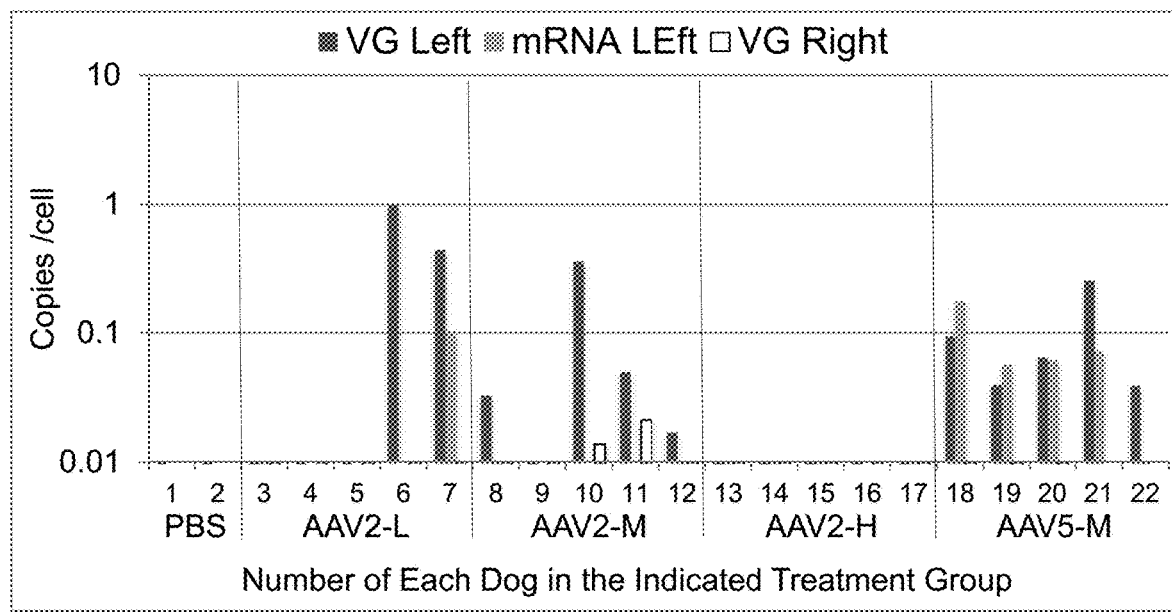
FIG. 6B is a graph showing vector genome and vector derived mRNA in each individual dogs analyzed using femoral condyle sample #1. Additionally, vector genome copies in contralateral (un-injected right joint) are shown (with the exception of sample #22, which was not tested).
Figure 6C:
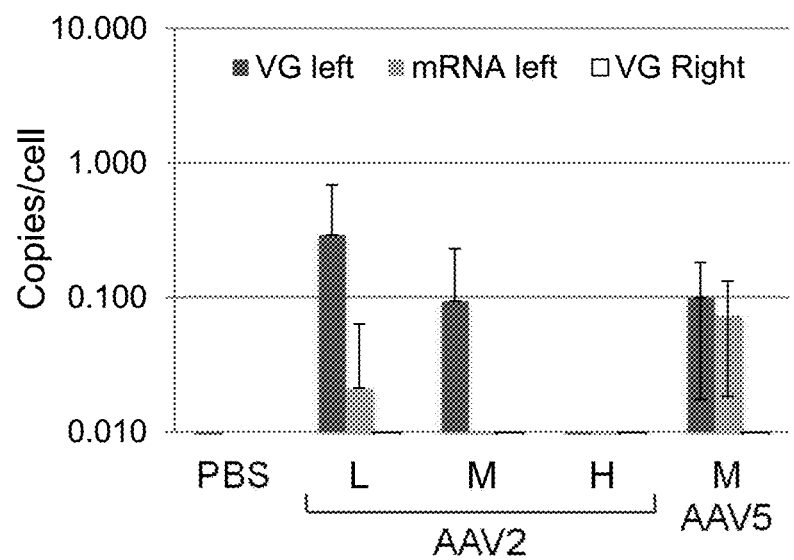
FIG. 6C is a graph showing the average of vector genome (injected and un-injected joints) and mRNA copies in each group. Vector dose for AAV2 and AAV5 is shown as L=low, M=medium and H=high (see FIG. 3). All tissue samples were collected 28 days after rAAV vector delivery and analyzed by qPCR to BGHpA.
Figure 6D:
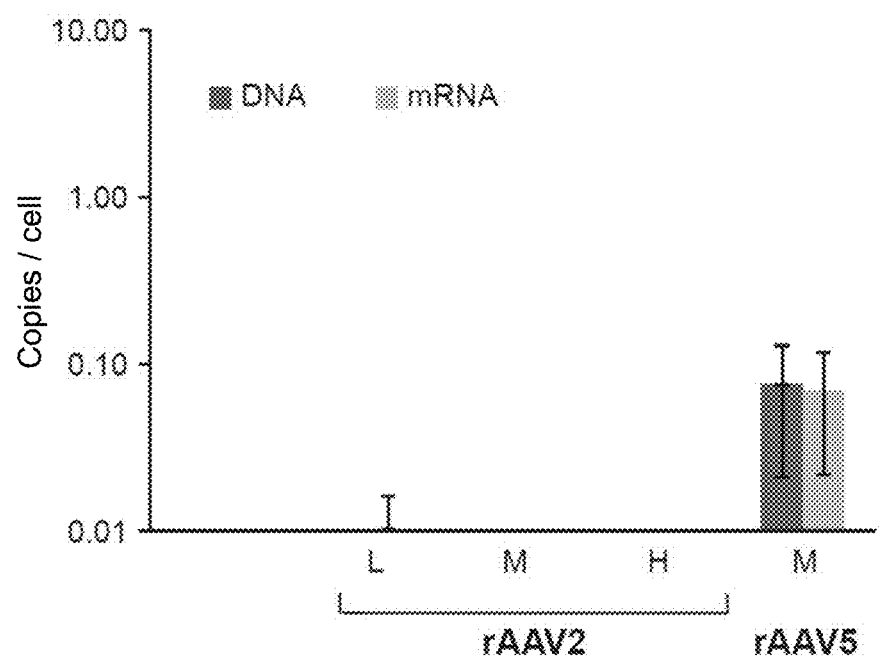
FIG. 6D is a graph showing the average of vector genome (PBS or vector-injected joints) and mRNA copies in tibial plateau cartilage in each group.

Vector genome detection in canine cartilage. Cartilage samples collected from femoral condyles and tibial plateaus were analyzed for detection of viral genomes (VGs; FIG. 6A). Vector DNA and mRNA detected in each individual injected joint and a group average in femoral condyles is shown as an example (FIG. 6B, C). The data showed that the AAV5 vector was present in a consistent manner in cartilage and showed comparable levels of vector derived transcripts. A comparable dose of AAV2 vector (medium) resulted in similar VG levels as AAV5 vector but showed approximately 100-fold lower mRNA levels. Additionally, AAV2 VG copies appeared to have a reverse correlation to vector dose. rAAV5-injected joints also showed vector detection and expression in cartilage samples collected from the tibial plateau while none was detected in rAAV2-treated joints (FIG. 6D) All vectors resulted in minimal vector DNA detection in the contralateral (un-injected) joints.

Figure 7A:
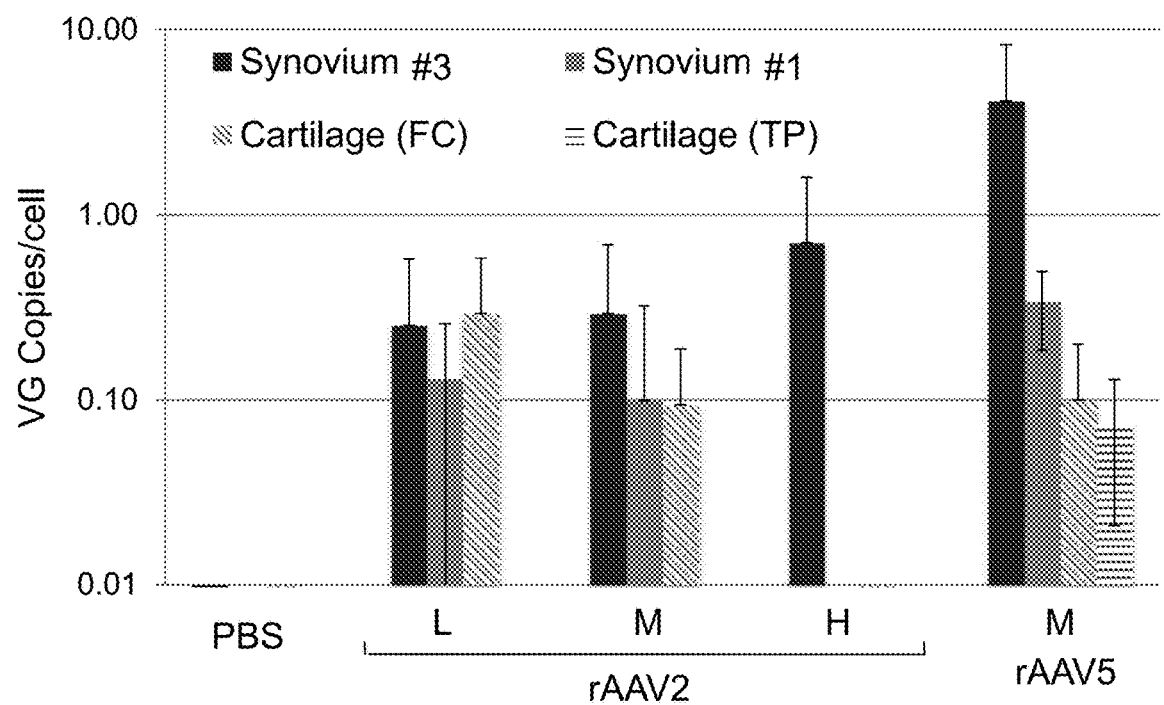
FIG. 7A is a graph showing vector genomes in synovium (samples #3 and #1) and cartilage (femoral condyle and tibial plateau) in each treatment group in tissues collected from the left stifle joints. The values shown in FIGS. 7A and 7B represent group average±standard deviation (n=5/group).
Figure 7B:
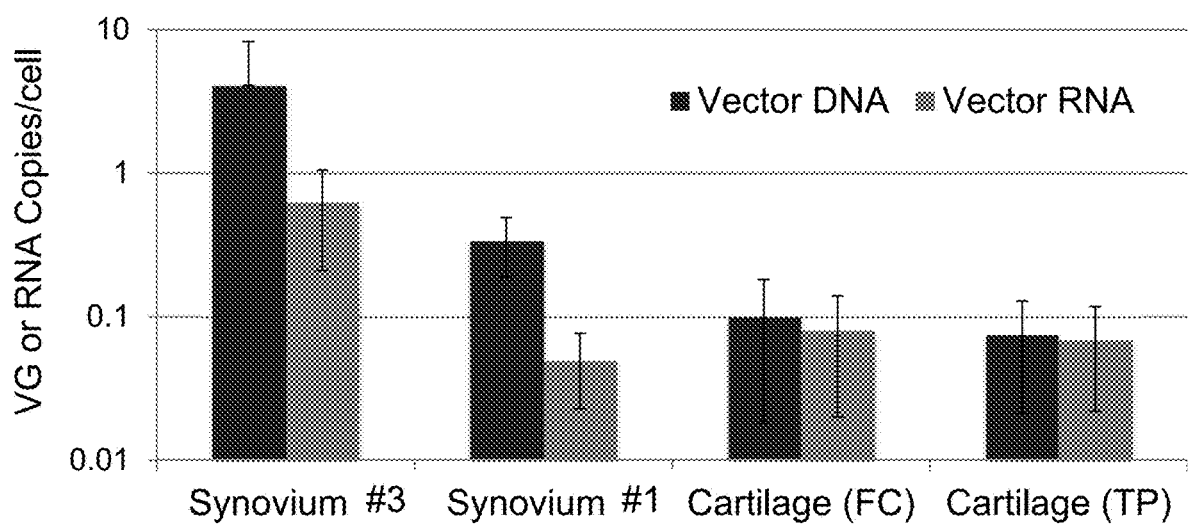
FIG. 7B is a graph showing quantitation of vector genomes and mRNA from the rAAV5/HAS2 vector in various tissues.

The synovial and cartilage results are summarized in FIG. 7A. For synovial gene transfer, AAV5 vectors resulted in approximately 10-fold higher vector DNA copies in both synovial sample locations compared to that of AAV2 vector. Gene transfer to cartilage was 10 to 20-fold lower than that of synovium by AAV5, while AAV2 vector genomes were observed at similar levels both in the synovium and cartilage. The rAAV5 vector derived genome and mRNA detection are summarized in FIG. 7B showing consistent gene transfer and expression by rAAV5/HAS2 vector in all tissue samples examined. Applicants deem this result to be highly unexpected.

Figure 8A:
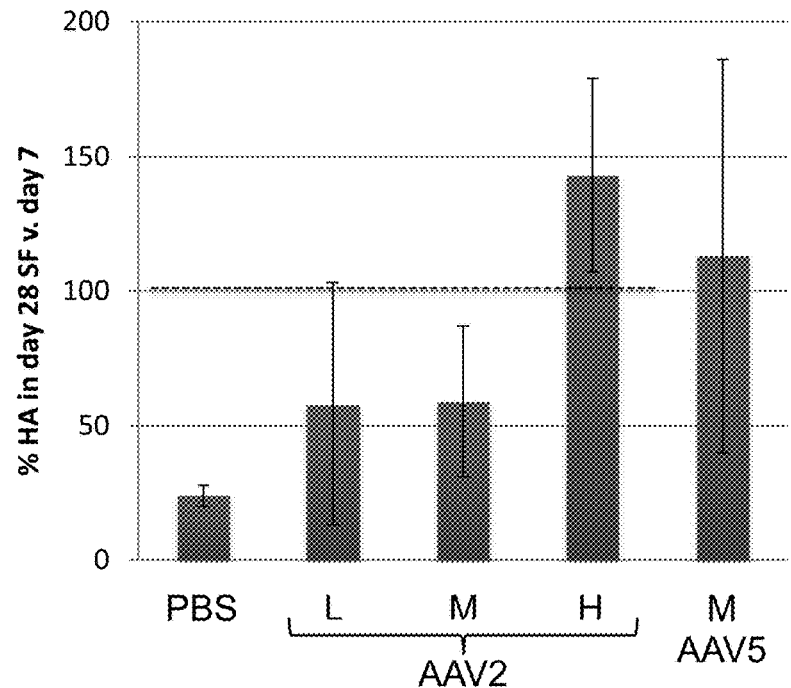
FIG. 8A is a graph showing the HA levels in canine synovial fluids. The HA levels were quantitated in SF samples collected on days −7 (baseline) and day 28. The HA levels in each animal were normalized to baseline levels and expressed as % of HA on day 28 compared to week before vector administration.
Figure 8B:
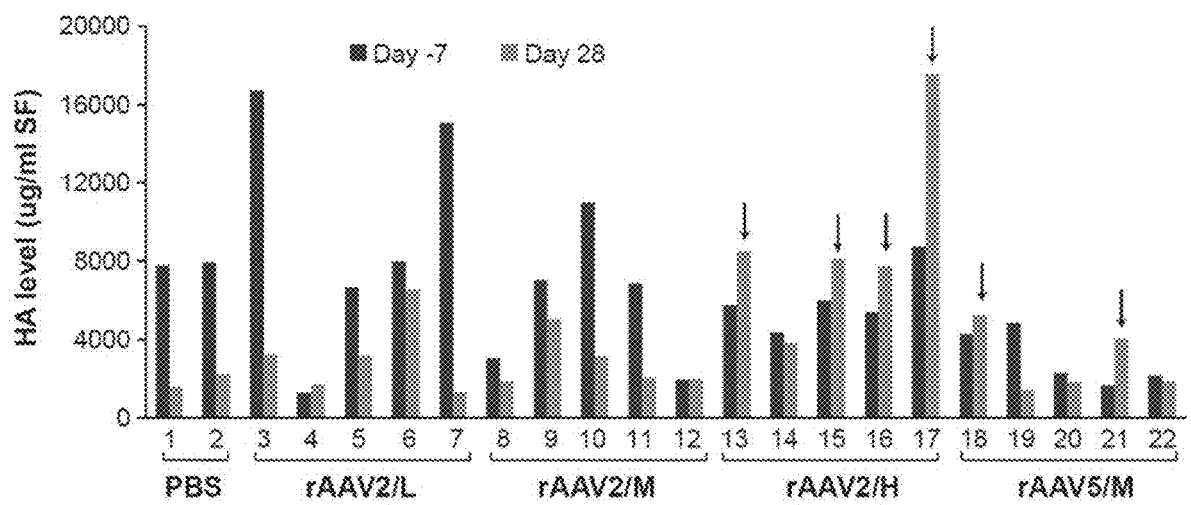
FIG. 8B is a graph showing the HA levels in canine synovial fluids at day −7 (baseline) and day 28. Arrows indicate animals with higher HA levels on day 28 compared to baseline (before treatment).

Analysis of HA levels in synovial fluids. To determine whether any changes in HA levels in synovial fluids could be detected after rAAV vector administration, the synovial HA levels were quantitated in samples collected on days −7 (baseline) and day 28. As high level of variation was detected among the animals, the HA levels in each animal were normalized to baseline levels in each animal. The data showed that compared to PBS-treated animals, both AAV2/high and AAV5/medium doses on average increased HA levels in synovial fluids (FIGS. 8A & 8B).

Example 1d—Conclusions

To provide overexpression of HA in the joint in vivo, Applicants generated rAAV vectors with two capsid serotypes. The choice of AAV capsid serotype is important as any pre-existing neutralizing antibodies in target species can neutralize the therapeutic vector and hence block gene transfer by rAAV vectors. The results disclosed herein showed that the majority of the dogs analyzed had low levels of neutralizing antibodies to both AAV2 and AAV5 capsids. As such, Applicants tested AAV2 and AAV5 capsid localization directly in the target tissue, namely canine knee joint, after intra-articular injection. Since HA expression is expected to be beneficial both for synoviocytes and chondrocytes, vector genome copies were quantitated in canine synovial and cartilage samples, respectively. The data showed that AAV2 provided very inconsistent gene transfer to canine synovial and cartilage tissues in vivo and showed little dose-response effect, the reasons of which are unclear. Similar experiments performed in rabbit OA joints demonstrated very consistent rAAV2 vector genome detection with a comparable vector dose (Kyostio-Moore 2015). In contrast to AAV2 vector, AAV5 vector genomes were detected in a consistent manner in both tissue types (n=5/group).

Importantly, detection of AAV5 in cartilage samples was surprising and unexpected since cartilage has been reported as difficult to transduce in in vivo conditions, due to extensive extracellular matrix and currently, there are no other reports on detection of AAV5 in cartilage of large animals after intra-articular delivery. In addition, the instantly disclosed canine studies produced unpredictably high levels of rAAV5 vector in canine synovial tissue, which were also about 2-logs higher in synovium compared to that in cartilage, indicating a preference for canine synovial lining by AAV5. This preferential expression pattern likewise could not have been predicted in advance of this disclosure.

In addition to detecting the high level of vector, recombinant HAS2 expression by mRNA analysis was confirmed in canine synovial and cartilage tissues, indicating that the CBA promoter was functional in both tissue types. Further, detection of transcripts by AAV5 in cartilage samples confirmed that chondrocytes were transduced by the vector rather than the virus being sequestered in the extracellular matrix of cartilage. For AAV2, comparable levels of vector genomes and transcripts were also observed in the synovial lining. However, the mRNA expression from AAV2 vectors was surprisingly approximately 100-fold lower than detection of corresponding vector genomes in cartilage samples, suggesting that some of the vector remained outside the chondrocytes, possibly retained to the extracellular matrix. These critical differences could only be appreciated after Applicants conducted significant non-routine experimentation.

Though the vectors were administered only to one joint in each animal, vector genomes were occasionally detected in the contralateral un-injected joint. This was mostly observed in the synovial samples obtained from AAV2-treated joints. However, none of the animals with vector genomes observed in the contralateral joints had any detectable HAS2 transcripts in these joints.

In summary, the data disclosed herein indicate that AAV5 capsid provides good gene transfer via intra-articular delivery to the canine joint. This is based on low pre-existing humoral immunity to AAV5 in subjects and ability to transduce joint tissues after intra-articular injection. Injections into joints can provide gene transfer not only to synovial lining but also to cartilage chondrocytes. Both tissue types will benefit from the increased HA synthesis afforded by the disclosed gene delivery compositions and methods: synovium, by the increased ability to provide lubrication in synovial fluid; and cartilage, by serving as a scaffold for increased matrix attachment and hence improved cartilage health. These results indicate that overexpression of HA by AAV-mediated HAS2 gene transfer to the disease site will decrease OA pathology and pain.

Example 2—Lubricin AAV Vector Construction and Evaluation

Example 2a—Overview

Recently, it has been demonstrated that intra-articular injections of recombinant lubricin protein reduced cartilage degeneration in a rat OA model (Flannery 2006). However, recombinant lubricin administered into joints had a very short half-life in the synovial fluids with the majority protein being cleared within 72 h (Vugmeyster 2011). As such, repeated intra-articular injections would be required which is laborious, stressful and costly. In contrast to HAS2 (see Example 1), lubricin is encoded by a large cDNA and contains multiple DNA repeats in its mucin-like domain making it difficult to fit into rAAV vectors and to express in high levels, respectively. To avoid this problem, Applicants generated a shortened canine lubricin cDNA to optimize small expression cassettes for increased lubricin production. Importantly, prior to this disclosure, neither the full-length canine lubricin sequence nor the shortened form as disclosed herein were known.

Briefly, Applicants generated a cDNA for a full-length canine lubricin that was subsequently used to design a shortened and codon-optimized version of canine lubricin (cLub1co). The latter was then used to construct various lubricin expressing plasmids. The plasmids were characterized for lubricin mRNA and protein production after transfection into HEK293 cells. The data showed both production of lubricin mRNA and secreted lubricin from each construct. Lastly, Applicants generated rAAV vectors with cLub1 expression cassette and demonstrated the feasibility of rAAV/cLub1 vector production. HEK293 cells infected with this construct synthesized and secreted canine lubricin.

Example 2b—Methods

Cloning of canine lubricin. Since no canine full-length lubricin cDNA exists in GenBank (incomplete sequence: GenBank no. ABD38836.1), a complete canine cDNA was obtained from custom synthesized canine cartilage cDNA library. To accomplish this, overlapping fragments were generated using qPCR with various primers. The full-length cDNA (SEQ ID NO:4) was then used to design a shortened form of canine lubricin (cLub1) similar to a published shorter version of human lubricin (Flannery 2009). This canine shorter lubricin contained a deletion in a sequence encoding amino acids 378 to 782. The shortened lubricin sequence was codon-optimized (cLub1co) and synthesized (GeneArt/Invitrogen). The cLubco fragment (KpnI blunt to PmeI) was cloned into the Mfe (blunted)—PmeI site of a plasmid containing a CMV enhancer, chicken β-actin promoter and shortened hybrid intron (HIb)(min CBA), and bovine growth hormone (BGH) polyadenylation (pA) site. The ligation reaction was transformed into E. coli Stable II cells and grown at 30° C. to minimize DNA rearrangements. Resulting clones were analyzed by restriction enzyme analyses and the cloning junctions were analyzed by DNA sequencing. Additional constructs were generated that contained 6× histidine (6×His) codons and modifications in two "ATG" sequences present in the intron sequence. Expression plasmids were used for analysis of lubricin expression in vitro.

Expression analysis for canine lubricin. Lubricin expression plasmids were transfected into HEK293 cells using Lipofectamine 2000 (Invitrogen) and cells were grown for 72 h. To analyze lubricin mRNA expression, the cells were collected and transcript levels were measured by real-time (RT) qPCR assay using primers/probe specific to BGH pA (7500 Real-Time PCR System; Applied Biosystems, Foster City, CA). For analysis of protein production, the culture media were collected and concentrated approximately 20- to 30-fold (100 k MWCO filter, Millipore). Samples were run on a 4-12% Bis-Tris gel or 3-8% Tris-acetate (NuPAGE; Thermo Fisher Scientific) SDS-PAGE gel (reduced) in MOPS or Tris-acetate buffer, respectively. Lubricin was detected by Western blot using a mouse anti-lubricin antibody (9G3, Millipore) (Ai 2015) and a goat anti-mouse-HRP as a secondary antibody (Jackson ImmunoResearch Laboratories, West Grove, PA).

Generation of AAV/cLub1co. The cLub1 expression cassette was cloned into a AAV inverted terminal repeats (ITRs) containing plasmid to generate expression cassette flanked by AAV ITRs (previral plasmid pDC627) to construct psITR/minCBA-HI-cLub1co-BGHpA. To test the packaging of the cLub1 expression cassette containing plasmid, 293 cells were seeded at 8×10$^5$ cells/well (6-well plates) and the following day transfected with psITR/minCBA-HI-cLub1co-BGHpA, or psp70/EGFP, pHLP-19cap2 (AAV2) or p5repCMVcap5 (AAV5) plasmids and pAdHELP (Promega CaPO$_4$ kit) to package vectors into AAV2 or AAV5 capsids. Cells were collected 3 days later and the lysates were quantitated for vector yield by qPCR assay (7500 Real-Time PCR System) using primer/probes specific to BGH pA sequences (Applied Biosystems/Life Technologies) and a standard curve of serially diluted linearized plasmid DNA containing BGH pA. The rAAV virus yields were expressed as amount of DNase-resistant particles (DRP) per cell (Clark 1999).

Research scale vector production was performed using triple transfection of psITR/minCBA-HI-cLub1co-BGH, pHLP19-cap5 for AAV5 vectors, and pAdHELP. The vectors were purified by CsCl gradient and yields quantitated as described above (University of Massachusetts Medical School, Worcester, MA).

Example 2c—Results

Generation of short canine lubricin. As the canine lubricin sequence present in GenBank was missing a large portion of exon 6 (encoding 857 amino acids), a full-length canine lubricin cDNA (4017 bp, not including the stop codon; SEQ ID NO:4) was generated that encoded for a protein with total of 1339 amino acids (SEQ ID NO: 5; FIG. 9), which is slightly smaller than human sequence of 1404 amino acids). At the amino acid level the canine lubricin sequence had 79% identity to that of human lubricin (SEQ ID NO:11; FIG. 16).

Figure 10:
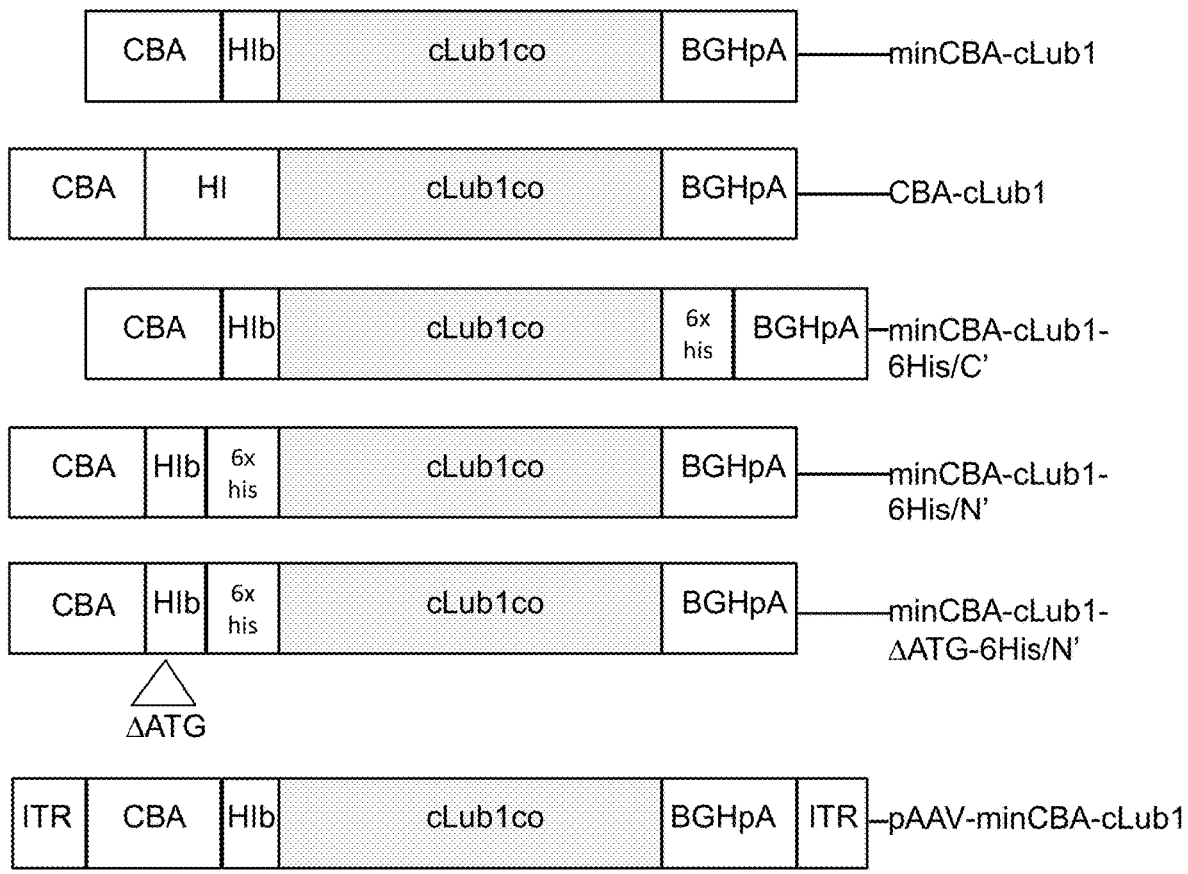
FIG. 10 is a diagram showing the plasmids generated and used in the experiments. The plasmids contain a shortened (i.e. an engineered internal deletion), codon-optimized canine lubricin sequence (cLub1co), promoter (minCBA or CBA) and a BGHpA site. Some constructs contain a N- or C-terminal His-tag (C-term) and a modification of ATG (potential start codons) removed from the intron sequence. A pre-viral AAV lubricin plasmid also contains flanking ITR sequences at both ends.

Since the full-length canine lubricin was too large to fit into the rAAV vector due to a packaging limit, a shortened version of canine lubricin was generated. This shorter version of canine lubricin, "Lub1," was generated by deleting a sequence coding for amino acids 378 to 782 in the mucin-like domain and resulted in a 2949 bp long cDNA (SEQ ID NO: 6) that encoded for 983 amino acids (SEQ ID NO: 7). Despite deletion of large portion of mucin-like domain, approximately ten KEPAPTT-like peptide repeats remained. Importantly, none of these are identical to the canonical human repeat sequence, but even if they had been, a skilled person could not have predicted whether delivery of the shortened canine Lub1 would be effective in treating OA. These repeats are thought to be important for lubrication properties as they are potential O-linked oligosaccharide attachment sites. The codon-optimization of this shorter lubricin (Lub1co; SEQ ID NO: 6) increased the GC content from 44% to 60% and had 74% nucleotide similarity to the original canine DNA sequence. This shorter canine cDNA was then used to generate a plasmid expression cassette with minCBA promoter, cLub1co and BGHpA (FIG. 10). Expression plasmids with 6×His-tags and modifications in putative ATG nucleotide sequences in the intron region (to minimize false translational start sites) were also made.

Figure 11A:
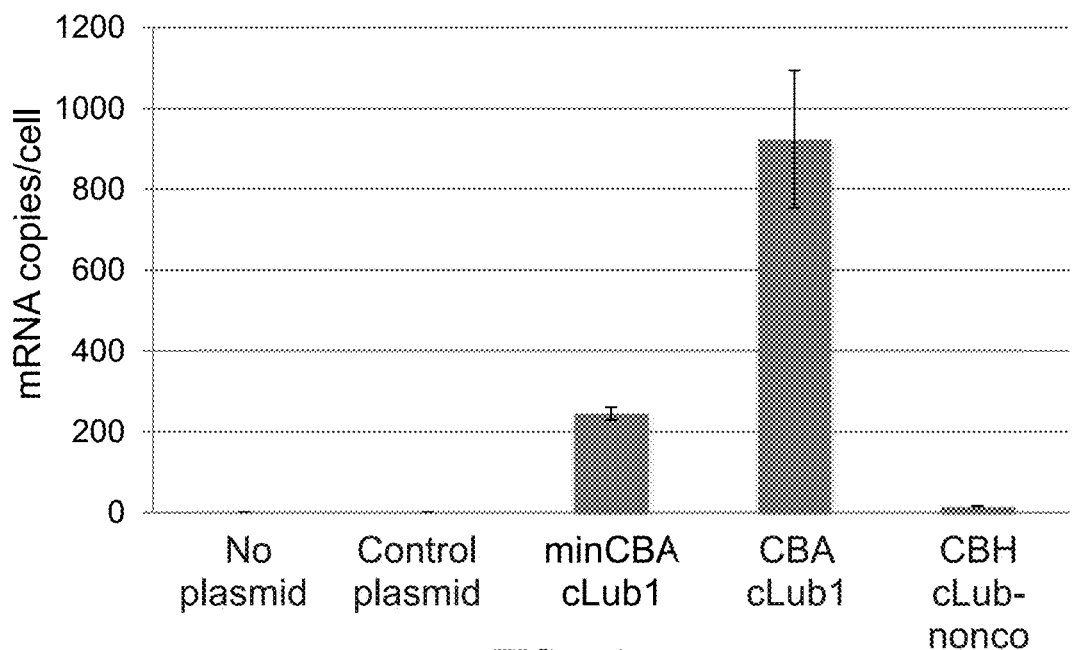
FIG. 11A is a graph showing mRNA copies/cell produced when the minCBA cLub1, CBA CLUB1 and CBH cLub-nonco constructs were transfected into 293 cells.
Figure 11B:
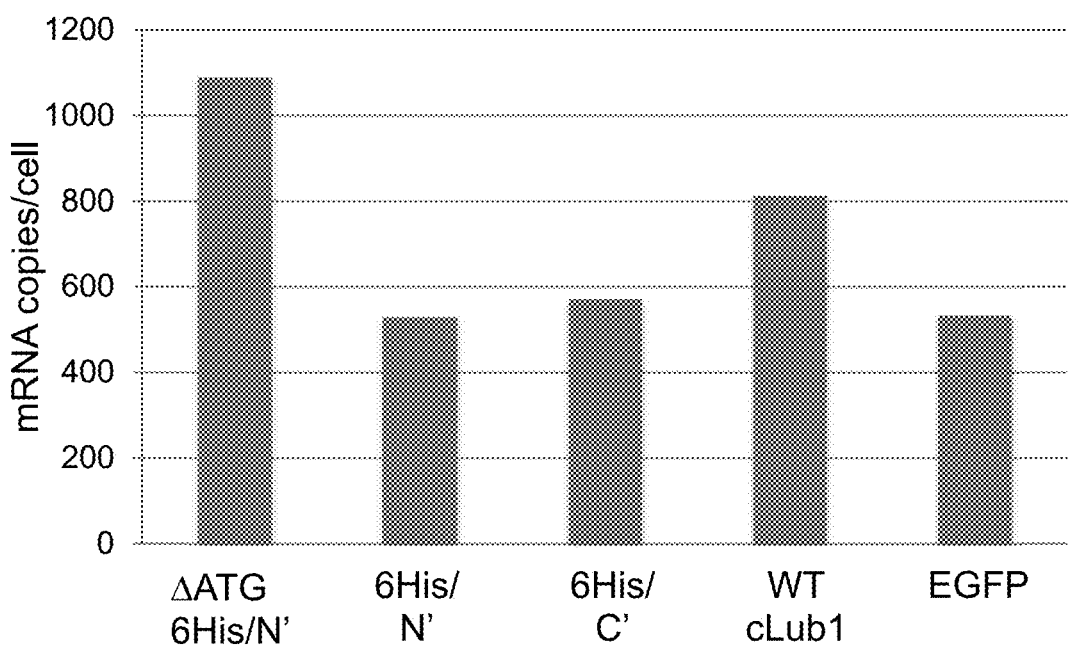
FIG. 11B is a graph showing mRNA copies/cell produced when the ΔATG/6His/N', 6His/N', 6His/C', WT cLub, and EGFP constructs were transfected into 293 cells.

Canine lubricin expression analysis. Expression of cLub1co from the minimal CBA promoter (minCBA-cLub1co) plasmid was confirmed in vitro by demonstrating increased mRNA levels in transfected 293 cells (FIG. 11A). The activity from the minCBA-cLub1co construct with the shorter intron was about 3-fold lower than using the full-length CBA-HI construct (CBA-cLub1co). Very little transcription was observed with plasmid containing the full-length lubricin and non-codon optimized construct (CBH-cLubr). Transcript analysis was also performed for expression cassettes with various modifications (FIGS. 10, 11B). Expression from the minCBA-Lub1co was comparable to expression of EGFP and construct with C-terminal 6×His-tag. Deletion of the putative two ATG codons present in the hybrid intron appeared to enhance expression levels about 2-fold. Additional morphological changes observed in Lub1co transfected cells also suggested Lub1 expression as these changes were not present in the un-transfected or EGFP-plasmid transfected cells (not shown).

Figure 12A:
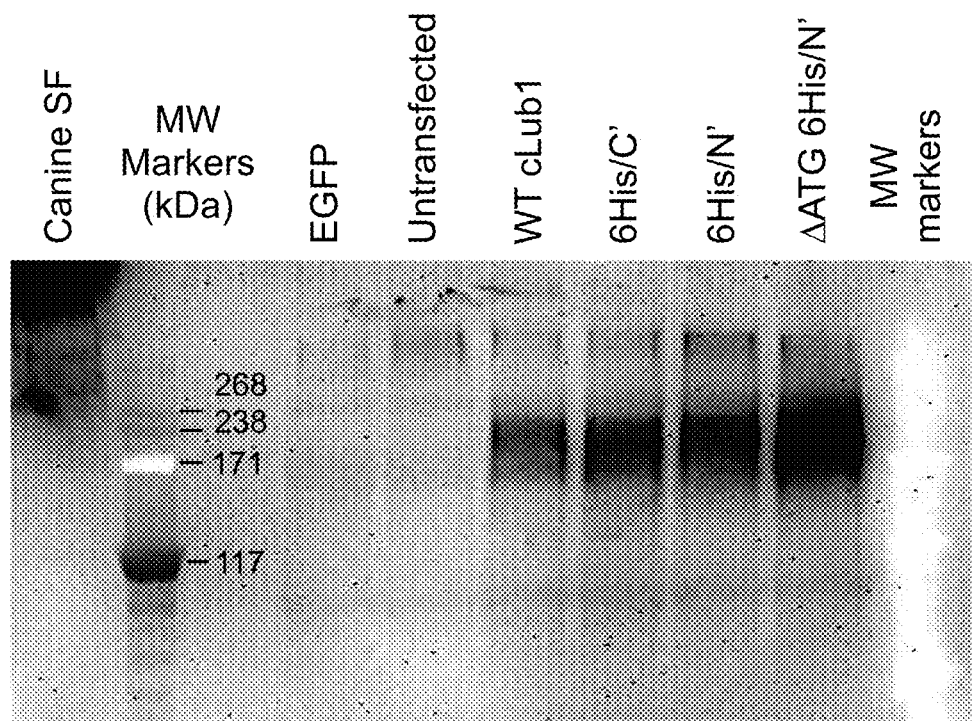
FIG. 12A is an anti-lubricin Western blot showing levels of secreted lubricin in concentrated media (plasmids described above). Canine synovial fluid was used as a positive control.
Figure 12B:
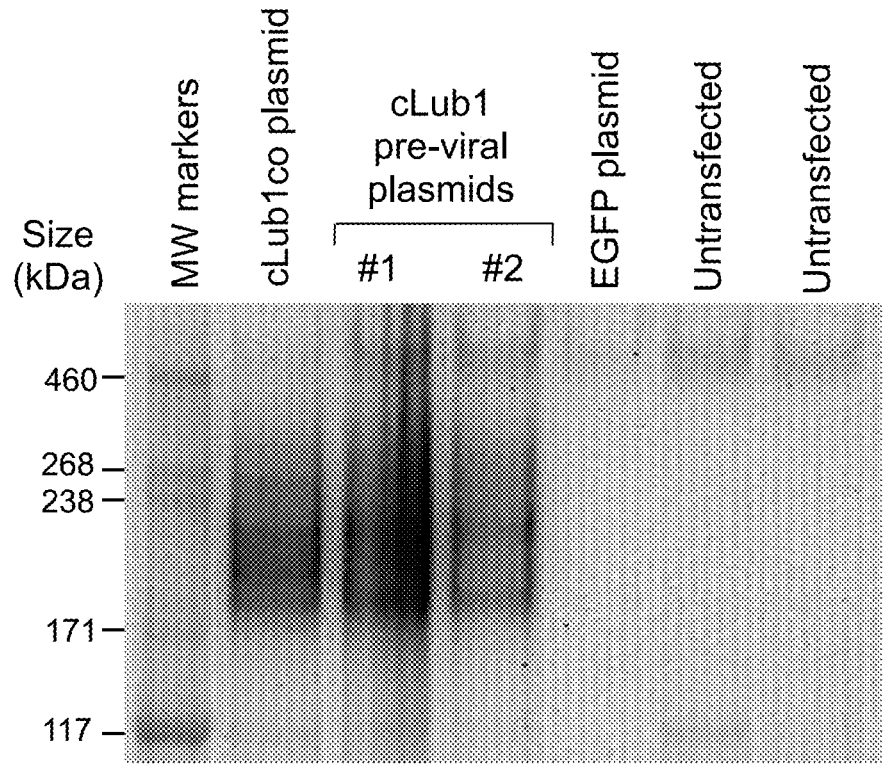
FIG. 12B is a Western blot showing lubricin production from pre-viral lubricin expression plasmids. Two clones were analyzed and compared to expression obtained with the minCBA-cLubco plasmid. Untransfected culture media and EGFP-expression plasmid transfected cells were run as negative controls.

Production of canine Lub1 protein from the various expression plasmids was tested by Western blot analysis using an antibody to lubricin and showed a protein of 250-380 kDa in the concentrated culture media (FIG. 12A). The expected size based on 1339 amino acid is approximately 160 kDa but the larger and diffuse pattern of the signal is likely due to glycosylation. Little detection was seen in un-transfected or EGFP plasmid transfected cells. Additionally, the ΔATG modification appeared to increase lubricin detection similar to observed for elevated transcript levels from this constructs. Protein expression was also confirmed from pre-viral AAV plasmid and showed comparable protein detection (FIG. 12B). In summary, these results demonstrate that the plasmids with canine lubricin expression cassettes expressed and secreted glycosylated lubricin protein.

Figure 13A:
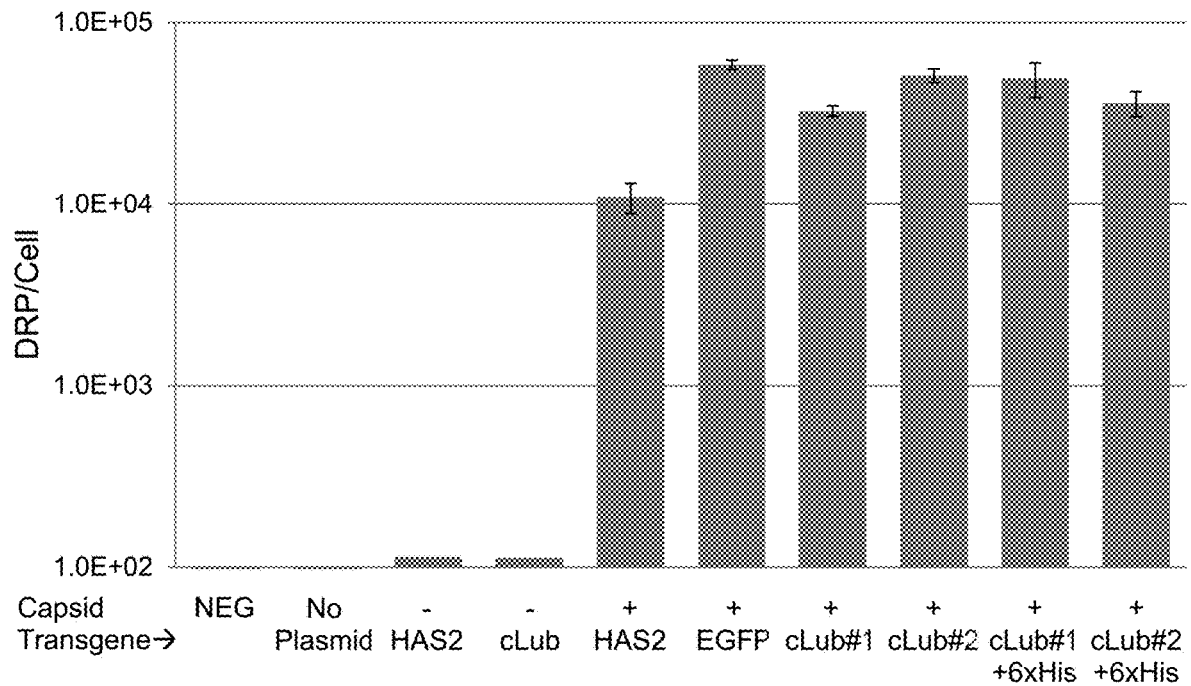
FIG. 13A is a graph showing vector yields in small-scale vector production for AAV2 vectors encoding canine lubricin. Two cLub clones (−/+6×His-tag) were analyzed and compared to packaging of EGFP and HAS2 expression cassettes present pre-viral (ITR-containing) plasmids. Negative controls included un-transfected cells and transfections lacking AAV2 capsid expressing plasmid.
Figure 13B:
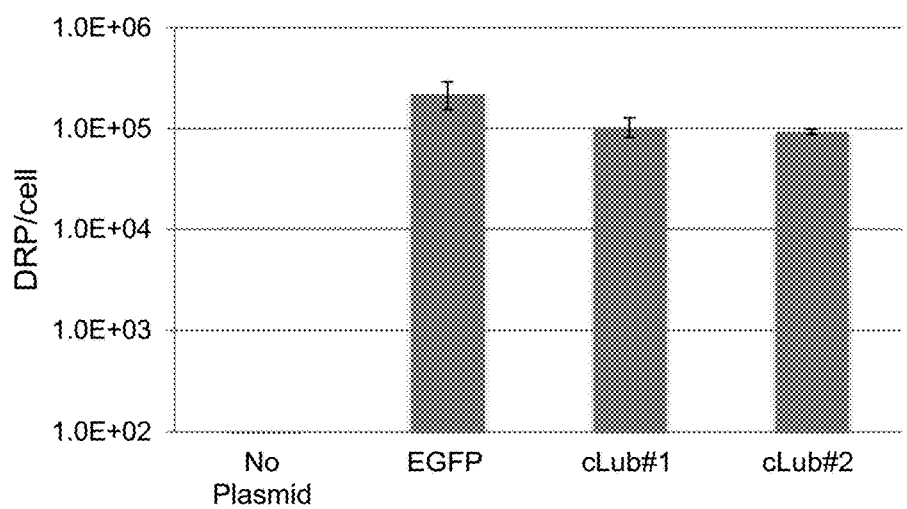
FIG. 13B is a graph showing vector yields in small scale vector production for AAV vectors encoding canine lubricin. Pre-viral plasmids for EGFP and cLub expression cassettes were transfected together with AAV capsid expressing plasmid.
Figure 14:
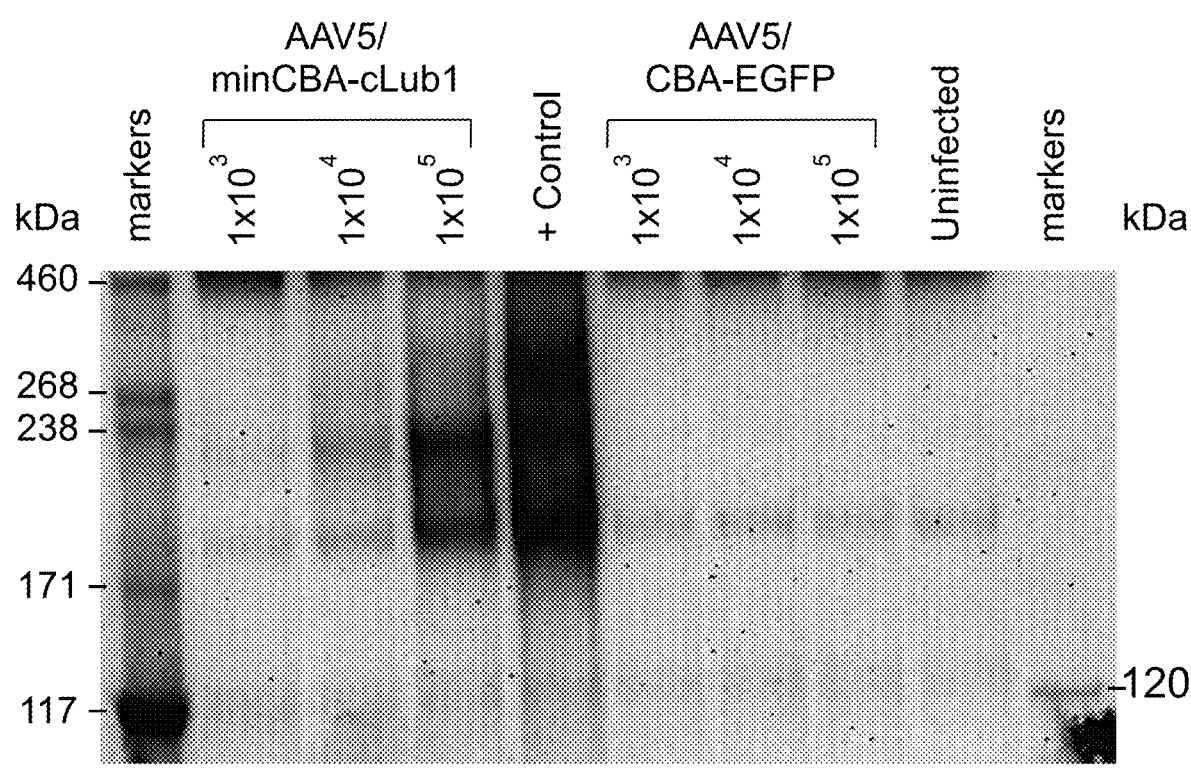
FIG. 14 is an anti-lubricin Western blot showing canine lubricin expression from rAAV5 vector in vitro. Human 293 cells were infected with rAAV5/minCBA-cLub1 at various amounts for 72 h followed by concentration of conditioned culture media. Culture media from AAV5/CBA-EGFP infected cells were used as negative control. Culture media from pre-viral lubricin expression plasmid transfected cells were used as positive control

Generation of rAAV vector with canine lubricin expression cassette. Having confirmed the canine lubricin expression from plasmid vectors, we next tested whether the expression cassette can be packaging into AAV2 and AAV capsid serotypes in a small-scale packaging experiment (FIGS. 13A, B). The data showed comparable packaging efficiency of canine lubricin both with AAV2 and AAV capsids as was observed for EGFP expression vectors. Inclusion of 6×His-tag did not alter rAAV vector yields. About 5-fold lower level of packaging was measured for AAV2 vector with a canine HAS2 expression cassette. A research-scale production of AAV5/minCBA-cLub1 was then performed to evaluate scaling-up vector production. The vector yield was comparable to that of standard AAV2 and AAV5 vectors with EGFP as transgene (data not shown). The rAAV5 vector was then tested for lubricin production and secretion in HEK293 cells in vitro. Analysis of conditioned media by Western blot demonstrated a dose-dependent detection of canine lubricin (FIG. 14). In summary, the data indicates that a shortened version of canine lubricin can be used to generate a rAAV vectors and that the cells infected with this vector can mediate lubricin synthesis and secretion into media.

Example 2d—Conclusion

As indicated above, lubricin as a transgene presents a number of challenges for rAAV generation. First, the size of lubricin cDNA with necessary expression elements exceeds the rAAV packaging capacity and thus, a shorter cDNA version was required. Interestingly, compared to the human lubricin amino acid sequence in the mucin-like domain, no perfect KEPAPTT-repeats exists in the canine sequence (FIG. 16). For generation of a recombinant rAAV vector, any repeating DNA sequences could pose a challenge as repeat sequences can reduce the stability and integrity of virus genomes by causing DNA deletions and rearrangements during virus production. However, the disclosed (and surprising) results indicated that the generation of rAAV virus containing and expressing the novel canine lubricin sequence was feasible, considering that comparable vector yields were obtained when compared to standard EGFP reporter vectors. Furthermore, cells infected with the disclosed vector both produced and secreted canine lubricin. Accordingly, this a first report demonstrating a single rAAV vector strategy for lubricin gene delivery.

Example 3—In Vivo Efficacy Study of AAV-HAS2 in Medial Meniscal Ligament Release (MMR) Model The objective of this study was to evaluate HA synthase-2 gene therapy efficacy using gross observations and histology of the canine OA stifle model. Twelve purpose-bred intact male mongrel dogs (foxhound phenotype, ≈20-23 kg) were anesthetized and the medial meniscal ligament release (MMR) of the right stifle was accomplished arthroscopically (d −14).

Phosphate buffered saline (PBS control) or $5 \times 10^{11}$ DNase resistant particles [drp] of recombinant AAV5 carrying canine hyaluronic acid synthase 2 (cHAS-2), were administered intra-articularly on Day 0 (n=6 dogs/group).

Plasma was collected on Days 0 and 182 from all dogs for joint inflammation biomarker levels. Right and left synovial fluid was collected for HA level analysis on Days 0, 56, 112 and 182 from all PBS control and cHAS-2 treatment groups.

Dogs were euthanized on Day 182, and the cartilage defect induced by meniscal ligament release (indicated by India ink staining) was measured and joint tissues were collected for histopathology according to OA Research Society International (OARSI) standard techniques.

Gross and histologic data were analyzed using Kruskal-Wallis with GraphPad Prism 6 statistical software.

Figure 17:
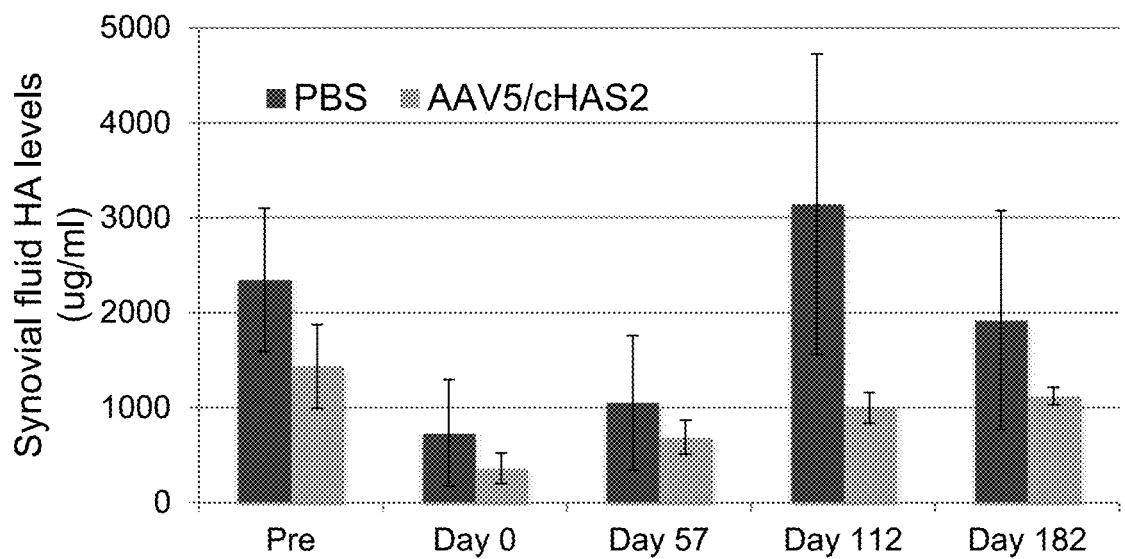
FIG. 17 is a graph showing HA levels in various timepoints in the canine synovial fluid using the MMR model. Synovial fluid was collected a week before OA induction (pre), two weeks after induction and prior to test article administration (day 0) and 57, 112 and 182 days after test article delivery

Total HA levels in synovial fluids were measured and did not show any treatment-related differences in total HA levels (FIG. 17).

Figure 18A:
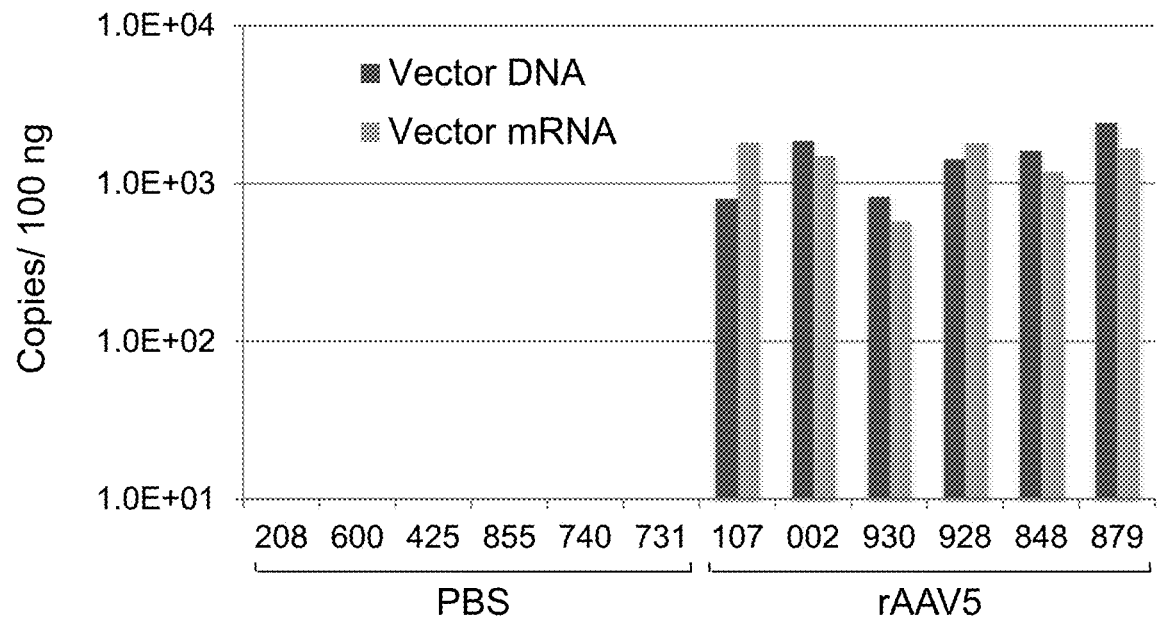
FIG. 18A is a graph showing rAAV5 vector detection and expression in synovial samples from canine OA joints 182 days after vector administration.
Figure 18B:
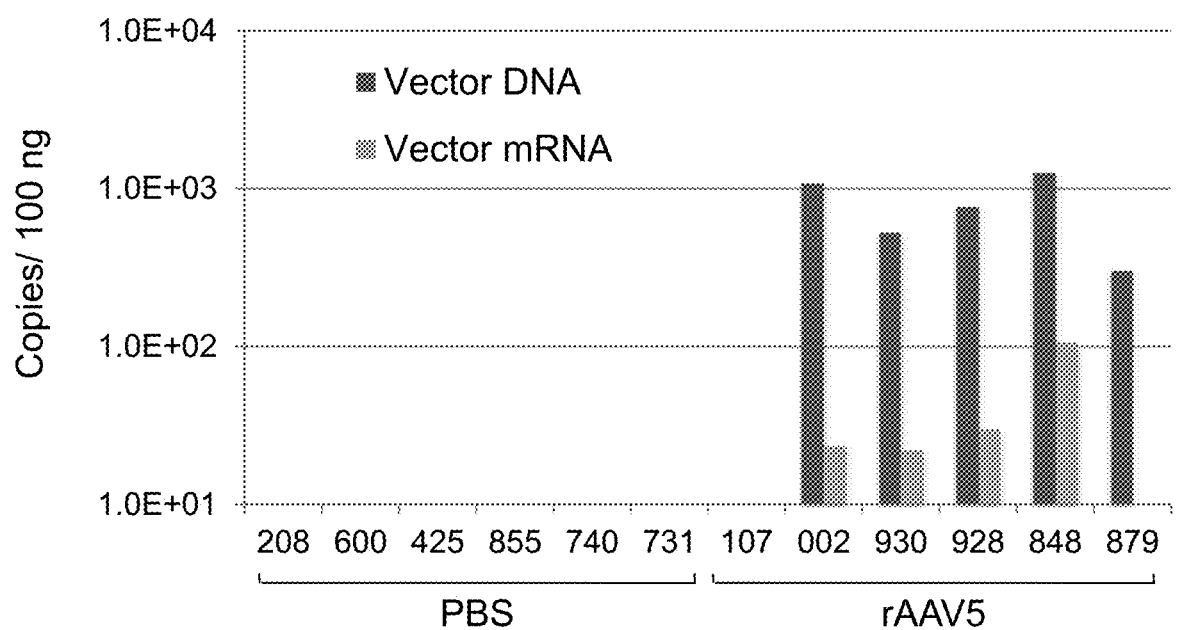
FIG. 18B is a graph showing rAAV5 vector detection and expression in cartilage (femoral condyles) of canine OA joints 182 days after vector administration.
Figure 18C:
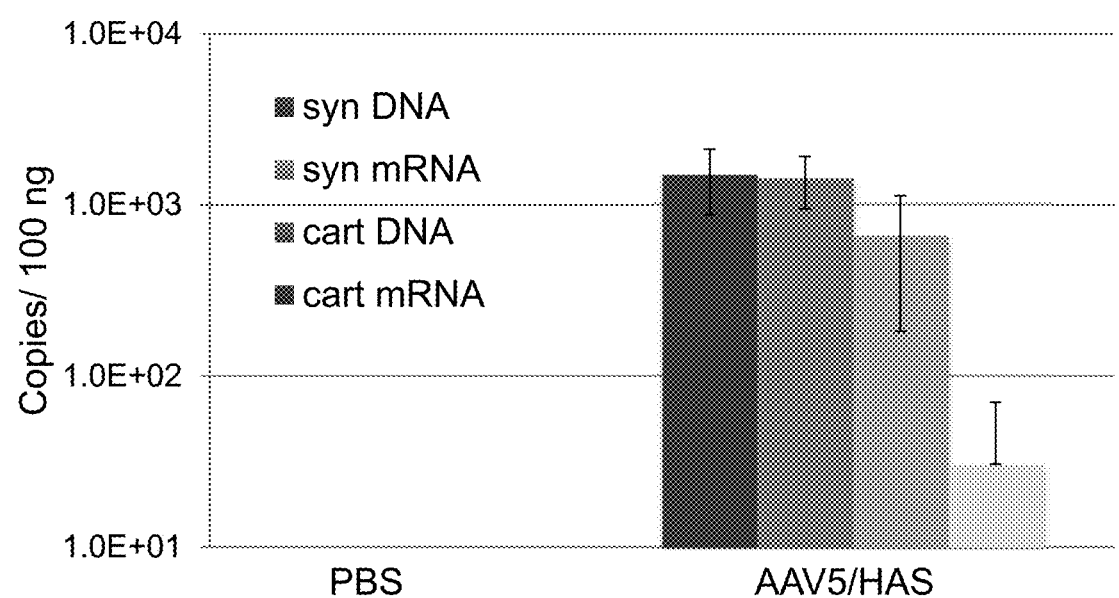
FIG. 18C summarizes rAAV5 vector genome and cHAS2 mRNA detection in synovial and cartilage samples on day 182 in the canine MMR OA model.

Synovial and cartilage samples were collected from the treated joints on day 182 and analyzed for detection of viral genomes (FIG. 18A). Vector derived DNA and mRNA were detected in each individual rAAV5/cHAS-2 injected joint in the synovial (FIG. 18A) and the majority of the cartilage (FIG. 18B) samples. The data is summarized in FIG. 18C showing group average for vector genomes and mRNA in both tissue samples.

There was no evidence of local or systemic toxicity associated with intra-articular administration of HA synthase-2 gene therapy. There was a consistent preservation of the cartilage structure in the cHAS-2 treatment group compared to PBS-treatment. Reduced size and depth of lesions on both medial femoral condyle and medial tibial plateau joint surfaces were more pronounced in the femoral condyle in four of the six rAAV5/cHAS2-treated dogs.

Figure 19:
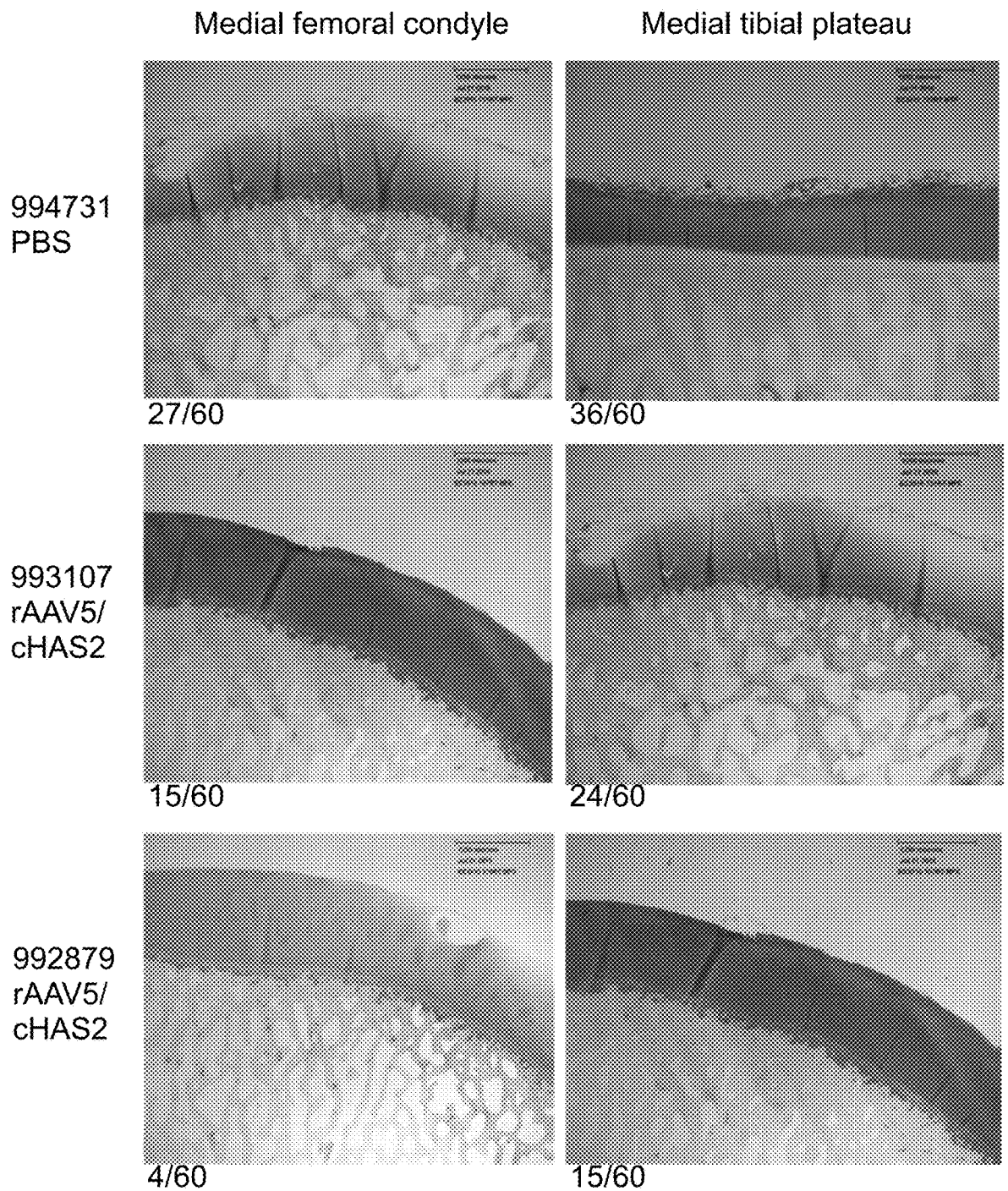
FIG. 19 shows safranin-O stained sections of cartilage surfaces obtained from the medial side from one PBS- and two rAAV5/cHAS2-treated canine joints as examples.

In FIG. 19, the histopathology score based on Cook et al. (2001) is shown in the lower left corner for each medial femoral condyle and medial tibial cartilage images (2×). Dog 994731/PBS had widespread erosion down to the middle zone with considerable loss of proteoglycan in both cartilage surfaces. No chondroprotective effect was observed. Dog 993107, treated with rAAV5/cHAS2, had shallow lesion in the superficial zone of the femoral cartilage, but overall, there was a good preservation of the rest of the cartilage and little loss of proteoglycan. The tibial plateau lesion was deeper into the middle zone with moderate proteoglycan depletion. A chondroprotective effect was observed in femoral condyle as the underlying cartilage is relatively normal. Dog 992879 treated with rAAV5/cHAS2 had some proteoglycan loss in femoral cartilage but the overall morphology was preserved. The tibial plateau had a well-defined focal erosion but the majority of the cartilage was preserved. Thus, there was some evidence of chondroprotection as the lesions were smaller and less severe.

Notably, one of the rAAV5-treated animals having no detectable vector in the cartilage sample also had the largest tibial plateau lesion area (dog 993107, FIG. 19). Conversely, one of the rAAV5-treated animals (dog 992879) having vector detected both in synovium and cartilage, but lacking mRNA detection the in cartilage, had the best cartilage structure.

Accordingly, the presence of the rAAV5-HAS2 vector is associated with the best cartilage structure, and, its absence is associated with the largest tibial plateau lesion area. Thus, despite variability in vector/mRNA detection, the rAAV5 vector expressing HAS2 appears to have elicited the desired clinical result.

Taken together, the results confirmed consistent rAAV5-mediated gene transfer into synovium and cartilage of canine OA joints and demonstrated sustained vector derived expression for at least six months. Histological analysis indicated reduced cartilage pathology and delayed disease progression in the majority of the cHAS-2 treated joints while little differences were observed in the total HA levels in the synovial fluid. The latter may indicate that local expression of HA in the cartilage and synovial tissues had some disease modifying properties without elevating total synovial fluid HA levels. Alternatively, changes in the molecular weight of HA synthesized that could not be detected by measuring total HA levels may have also contributed to beneficial effects by the rAAV5/cHAS-2.

REFERENCES

Sanderson R O et al. Systematic review of the management of canine osteoarthritis. Veterinary Record (2009) 164, 418-424

McIlwraith C W. Frank Milne Lecture: from arthroscopy to gene therapy: 30 years of looking in joints. Am Assoc Equine Pract 2005; 51:65-113.

Cook et al. The OARSI histopathology initiative-recommendations for histological assessments of osteoarthritis in the dog. Osteoarthritis Cartilage, 2010; 18 suppl 3:S66-79.

The invention is further described in the following numbered paragraphs:

1. A method of treating a mammalian subject suffering from osteoarthritis (OA), comprising intra-articularly administering to said mammalian subject a therapeutically effective amount of a recombinant adeno-associated virus (rAAV) comprising a nucleic acid encoding an osteo-protective or osteo-regenerative polypeptide operably linked to a promoter, wherein the polypeptide is expressed in vivo in the mammalian subject in an amount effective to alleviate the symptoms of OA.

2. The method of paragraph 1, wherein the polypeptide is a hyaluronic acid synthase (HAS), i a lubricin, an Interleukin-1 Receptor (IL-1R) antagonist, an Insulin-like growth factor 1 (IGF-1), a fibroblast growth factor 2 (FGF-2), a Transforming growth factor beta 1 (TGFβ1), a Bone Morphogenetic protein 7 (BMP7), a Glucosamine-fructose-6-phosphate aminotransferase (GFAT), an Interleukin 10 (IL-10), a heme oxygenase-1 HO-1, biologically active truncations thereof, or combinations thereof.

3. The method of paragraph 1 or 2, wherein the polypeptide is a HAS2 polypeptide.

4. The method of any one of paragraphs 1-3, wherein the mammalian subject is a human, canine or feline.

5. The method of any one of paragraphs 1-4, wherein the mammalian subject is a canine.

6. The method of paragraph 5, wherein the polypeptide is canine HAS2.

7. The method of paragraph 5 or 6, wherein the HAS2 polypeptide comprises an amino acid sequence having at least 90% identity to the amino acid sequence as set forth in SEQ ID NO: 2, or a fragment, a variant, or a homolog thereof which exhibits HAS2 activity in vivo in the subject.

8. The method of any one of paragraphs 5-7, wherein the HAS2 polypeptide comprises the amino acid sequence set forth in SEQ ID NO: 2.

9. The method of any one of paragraphs 5-8, wherein the nucleic acid encoding the HAS2 polypeptide has a nucleotide sequence having at least 90% identity to the nucleotide sequence set forth in SEQ ID NO: 3.

10. The method of any one of paragraphs 5-9, wherein the rAAV comprises a rAAV vector genome comprising from 5' to 3' the following elements: 5' AAV inverted terminal repeat (ITR), stuffer nucleic acid, a promoter, an intron (IN), a cHAS2 codon-optimized cDNA, a polyadenylation signal (pA), and a 3' AAV ITR.

11. The method of paragraph 10, wherein the promoter is a chicken beta-actin (CBA) promoter.

12. The method of paragraph 1 or 2, wherein the polypeptide is a lubricin polypeptide.

13. The method of paragraph 12, wherein the lubricin polypeptide comprises an amino acid sequence having at least 90% identity to the amino acid sequence set forth in SEQ ID NO: 7, or a fragment, a variant, or a homolog thereof which exhibits Lubricin activity in vivo in the subject.

14. The method of paragraph 13, wherein the lubricin polypeptide comprises the amino acid sequence set forth in SEQ ID NO: 7.

15. The method of paragraph 13 or 14, wherein the nucleic acid encoding the lubricin polypeptide has a nucleotide sequence having at least 90% identity to the nucleotide sequence set forth in SEQ ID NO: 6.

16. The method of any one of paragraphs 13-14, wherein the rAAV comprises a rAAV vector genome encoded by plasmid pITR/minCBA-HI-cLub1co-BGH.

17. The method of any of paragraphs 1-9 or 12-16, wherein the promoter is selected from the group consisting of a CMV IE promoter, a RSV promoter, an HSV-1 TK promoter, a SV40 early promoter, a SV40 late promoter, an adenovirus major late promoter, a phosphoglycerate kinase gene promoter, a metallothionein gene promoter, an α-1 antitrypsin gene promoter, an albumin gene promoter, a collagenase gene promoter, an elastase I gene promoter, a β-actin gene promoter, a CBA promoter, a β-globin gene promoter, a γ-globin gene promoter, an α-fetoprotein gene promoter, and a muscle creatine kinase (CK) gene promoter.

18. The method of paragraph 1, wherein the AAV comprises an AAV2 or an AAV5 capsid.

19. A method of increasing the production of hyaluronic acid in chondrocytes and/or synoviocytes of a canine, comprising the steps of administering a rAAV to the canine, wherein the rAAV comprises a rAAV vector genome comprising nucleic acid encoding an HAS2 enzyme operably linked to a promoter, and wherein following administration the HAS2 enzyme is expressed and catalyzes the production of additional hyaluronic acid, thereby increasing the level of hyaluronic acid (HA) in the canine.

20. The method of paragraph 19, wherein the HAS2 is produced in sufficient quantity to treat the symptoms of OA in canine.

21. The method of paragraph 20, wherein the HA levels are restored to levels found in healthy canines.

22. A method of treating a canine suffering from OA, comprising administering to the canine a therapeutically effective amount of rAAV, wherein the rAAV comprises an AAV vector genome comprising a nucleic acid encoding a HAS2 operably linked to a promoter.

23. A method of treating a human suffering from OA, comprising, administering to the human a therapeutically effective amount of rAAV, wherein the rAAV comprises an AAV vector comprising nucleic acid encoding a HAS2 operably linked to a promoter.

24. The method of any one of paragraphs 19-23, wherein the nucleic acid encoding the HAS2 has at least 90% identity to the nucleotide sequence set forth in SEQ ID NO:3 or encodes an HAS2 that has an amino acid sequence at least 90% identical to the amino acid sequence of SEQ ID NO: 2.

25. The method of any one of paragraphs 19-23, wherein the HAS2 has the amino acid sequence set forth in SEQ ID NO: 2.

26. A method of increasing the production of a lubricin in chondrocytes and/or synoviocytes of a canine, comprising the steps of administering a rAAV to the canine, wherein the rAAV comprises a rAAV vector comprising nucleic acid encoding a lubricin operably linked to a promoter, and wherein following administration the lubricin is expressed thereby increasing the level of lubricin in the canine.

27. The method of paragraph 26, wherein the lubricin is produced in sufficient quantity to treat the symptoms of OA in canine.

28. The method of paragraph 26, wherein the lubricin levels are restored to levels found in healthy canines.

29. A method of treating a canine suffering from OA, comprising, administering to said canine a therapeutically effective amount of rAAV, wherein the rAAV comprises an rAAV vector genome comprising nucleic acid encoding a lubricin operably linked to a promoter.

30. A method of treating a human suffering from OA, comprising administering to said human a therapeutically effective amount rAAV, wherein the rAAV comprises an AAV vector genome comprising nucleic acid encoding a lubricin operably linked to a promoter.

31. The method of any one of paragraphs 26-30, wherein the nucleic acid encoding the lubricin polypeptide has at least 90% identity to the sequence set forth in SEQ ID NO: 6 or the nucleic acid encodes a lubricin that has an amino acid sequence at least 90% identical to the amino acid sequence set forth in SEQ ID NO: 7.

32. The method of any one of paragraphs 26-30, wherein the lubricin has the amino acid sequence set forth in SEQ ID NO: 7.

33. The method of any one of paragraphs 19-32, wherein the promoter is selected from the group consisting of a CMV IE promoter, a RSV promoter, an HSV-1 TK promoter, a SV40 early promoter, a SV40 late promoter, a phosphoglycerate kinase gene promoter, a metallothionein gene promoter, an α-1 antitrypsin gene promoter, an albumin gene promoter, a collagenase gene promoter, an elastase I gene promoter, a CBA promoter, a β-actin gene promoter, a β-globin gene promoter, a γ-globin gene promoter, an α-fetoprotein gene promoter, and a muscle creatine kinase gene promoter.

34. The method of any one of paragraphs 19-25, wherein the rAAV comprises a rAAV vector genome encoded by plasmid Ps-AAV-ITR/CBA-cHAS2co-BGH.

35. The method of any one of paragraphs 26-32, wherein the rAAV comprises a rAAV vector genome encoded by plasmid Ps-AAV-ITR/minCBA-HI-cLub1co-BGH.

36. A method of preventing the development of OA in a mammalian subject at risk thereof, comprising administering to said canine a therapeutically effective amount of rAAV, wherein the rAAV comprises an rAAV vector genome comprising nucleic acid encoding a HAS2 operably linked to a promoter.

37. The method of paragraph 36, wherein the nucleic acid encoding the HAS2 polypeptide has at least 90% identity to the sequence set forth in SEQ ID NO: 2 or encodes a HAS2 that has an amino acid sequence at least 90% identical to the amino acid sequence of SEQ ID NO: 2.

38. The method of paragraph 36 or 37, wherein the HAS2 polypeptide comprises the amino acid sequence set forth in SEQ ID NO: 3.

39. A method of preventing the development of OA in a mammalian subject at risk thereof, comprising administering to said canine a therapeutically effective amount of a rAAV, wherein the rAAV comprises a rAAV vector genome comprising nucleic acid encoding a lubricin operably linked to a promoter.

40. The method of paragraph 39, wherein the nucleic acid encoding the lubricin has at least 90% identity to the sequence as set forth in SEQ ID NO: 6 or the nucleic acid encodes a lubricin that has an amino acid sequence at least 90% identical to the amino acid sequence set forth in SEQ ID NO: 7.

41. The method of paragraph 40, wherein the lubricin polypeptide has the amino acid sequence set forth in SEQ ID NO: 7.

42. The method of any one of paragraphs 36-38, wherein the promoter is selected from the group consisting of a CMV IE promoter, a RSV promoter, an HSV-1 TK promoter, a SV40 early promoter, a SV40 late promoter, a phosphoglycerate kinase gene promoter, a metallothionein gene promoter, an α-1 antitrypsin gene promoter, an albumin gene promoter, a collagenase gene promoter, an elastase I gene promoter, a CBA promoter, a β-actin gene promoter, a β-globin gene promoter, a γ-globin gene promoter, an α-fetoprotein gene promoter, and a muscle creatine kinase gene promoter.

43. The method of paragraphs 26, wherein the rAAV comprises a rAAV vector genome encoded by plasmid Ps-AAV-ITR/CBA-cHAS2co-BGH.

44. The method of paragraphs 26, wherein the rAAV comprises a rAAV vector genome encoded by plasmid Ps-AAV-ITR/minCBA-HI-cLub1co-BGH.

45. The method of any one of paragraphs 19-44, wherein the rAAV is administered intra-articularly.

46. A recombinant plasmid vector comprising a nucleic acid sequence encoding a canine HAS2 polypeptide operably linked to a promoter.

47. The recombinant plasmid of paragraph 46, wherein the nucleic acid sequence encoding the HAS2 polypeptide has at least 90% identity to the sequence as set forth in SEQ ID NO:3 or the nucleic acid encodes a HAS2 polypeptide comprising an amino acid sequence at least 90% identical to the amino acid sequence set forth in SEQ ID NO: 2.

48. The recombinant plasmid of paragraph 46 or 47, wherein the HAS2 polypeptide comprises the amino acid sequence set forth in SEQ ID NO: 2.

49. The recombinant plasmid of any one of paragraphs 46-49, comprising pCBA-HI-cHAS2-BGHpA.

50. A recombinant plasmid vector comprising a nucleic acid sequence encoding a shortened canine lubricin operably linked to a promoter.

51. The recombinant plasmid of paragraph 50, wherein the nucleic acid sequence encoding the lubricin has at least 90% identity to the nucleotide sequence set forth in SEQ ID NO: 6 or the nucleic acid encodes a lubricin comprising an amino acid sequence at least 90% identical to the amino acid sequence set forth in SEQ ID NO: 7.

52. The recombinant plasmid of paragraph 50 or 51, wherein the lubricin polypeptide has an amino acid sequence as set forth in SEQ ID NO: 7.

53. The recombinant plasmid of any one of paragraphs 46-49 or 50-52, wherein the promoter is selected from the group consisting of a CMV IE promoter, a RSV promoter, an HSV-1 TK promoter, a SV40 early promoter, a SV40 late promoter, a phosphoglycerate kinase gene promoter, a metallothionein gene promoter, an α-1 antitrypsin gene promoter, an albumin gene promoter, a collagenase gene promoter, an elastase I gene promoter, a CBA promoter, a β-actin gene promoter, a β-globin gene promoter, a γ-globin gene promoter, an α-fetoprotein gene promoter, and a muscle creatine kinase gene promoter.

54. A recombinant AAV viral vector comprising the nucleotide sequence set forth in SEQ ID NO: 8.

55. A rAAV comprising the rAAV vector of paragraph 53.

56. A pharmaceutical composition comprising the rAAV of paragraph 55, and at least one pharmaceutically or veterinarily acceptable carrier, excipient, or vehicle.

57. A method of treating a mammalian subject suffering from osteoarthritis, comprising, intra-articularly administering to said mammalian subject a therapeutically effective amount of the pharmaceutical composition of paragraph 56.

58. The method of paragraph 57, wherein the mammalian subject is a human or canine animal.

59. An adeno-associated virus (AAV)-based biological delivery and expression system for use in the treatment of OA in mammalian joints by long-term gene expression of HAS2 or lubricin in synovial and/or chondrocyte cells, comprising a rAAV, wherein the rAAV comprises a rAAV vector comprising a nucleic acid sequence encoding HAS2 or lubricin, left and right AAV inverted terminal repeats (L ITR and R ITR), and wherein the expression of the HAS2 or lubricin gene within synovial and/or chondrocyte cells is regulated by a promoter, which is located upstream of the reading frame of the nucleic acid sequence encoding for HAS2 or lubricin and which is specifically activated by increased levels of immune stimulatory substances.

60. The AAV system of paragraph 59, wherein the HAS2 is a mammalian HAS2.

61. The AAV system of paragraph 59 or 60, wherein the HAS2 is a human HAS2.

62. The AAV system of any one of paragraphs 59-61, wherein the promoter is an inflammation-inducible promoter.

63. The AAV system of paragraph 62, wherein the inducible promoter is selected from the following: an NF-KB promoter, an interleukin 6 (Il-6) promoter, an interleukin-1 (Il-1) promoter, a tumor necrosis factor (TNF) promoter, a cyclooxygenase 2 (COX-2) promoter, a complement factor 3 (C3) promoter, a serum amyloid A3 (SAA3) promoter, a macrophage inflammatory protein-1a (MIP-1a) promoter and hybrid constructs thereof.

64. The AAV system according to any one of paragraphs 59-63, wherein the rAAV vector genome comprises nucleic acid encoding a HAS2 comprising the amino acid sequence of SEQ ID NO: 2, a lubricin comprising the amino acid sequence of SEQ ID NO: 7, or a functional variant thereof.

65. The AAV system of any one of paragraphs 59-64, wherein the rAAV vector genome comprises a marker gene that allows monitoring of the vector genome in the synovial and/or chondrocyte cells.

66. The AAV system of any one of paragraphs 59-65, wherein the rAAV vector genome comprises a nucleic acid having at least 80% or 90% sequence identity to the nucleic acid sequence set forth in SEQ ID NO:3 or SEQ ID NO: 6.

67. The AAV system of any one of paragraphs 59-66, wherein the rAAV vector genome comprises a nucleic acid sequence set forth in SEQ ID NO:3 or SEQ ID NO: 6.

68. The AAV system of any one of paragraphs 59-67 for the treatment or prevention of osteoarthritis (OA).

69. A pharmaceutical composition, comprising the AAV system of any one of paragraphs 59-68.

70. A rAAV comprising a rAAV vector, wherein the rAAV vector comprises a nucleic acid sequence encoding a canine HAS2 polypeptide operably linked to a promoter.

71. The rAAV of paragraph 70, wherein the nucleic acid sequence encoding the HAS2 polypeptide has at least 90% identity to the sequence as set forth in SEQ ID NO:3 or the nucleic acid encodes a HAS2 polypeptide comprising an amino acid sequence at least 90% identical to the amino acid sequence set forth in SEQ ID NO: 2.

72. The rAAV of paragraph 70 or 71, wherein the HAS2 polypeptide comprises the amino acid sequence set forth in SEQ ID NO: 2.

73. A rAAV comprising a rAAV vector, wherein the rAAV vector comprises a nucleic acid sequence encoding a shortened canine lubricin operably linked to a promoter.

74. The rAAV of paragraph 73, wherein the nucleic acid sequence encoding the lubricin has at least 90% identity to the nucleotide sequence set forth in SEQ ID NO: 6 or the nucleic acid encodes a lubricin comprising an amino acid sequence at least 90% identical to the amino acid sequence set forth in SEQ ID NO: 7.

75. The rAAV of paragraph 73 or 74, wherein the lubricin polypeptide has an amino acid sequence as set forth in SEQ ID NO: 7.

76. The rAAV of any one of paragraphs 50-53, wherein the rAAV vector comprises the nucleotide sequence as set forth in SEQ ID NO: 8.

77. The rAAV of any one of paragraphs 71-72 or 74-76, wherein the promoter is selected from the group consisting of a CMV IE promoter, a RSV promoter, an HSV-1 TK promoter, a SV40 early promoter, a SV40 late promoter, a phosphoglycerate kinase gene promoter, a metallothionein gene promoter, an α-1 antitrypsin gene promoter, an albumin gene promoter, a collagenase gene promoter, an elastase I gene promoter, a CBA promoter, a β-actin gene promoter, a β-globin gene promoter, a γ-globin gene promoter, an α-fetoprotein gene promoter, and a muscle creatine kinase gene promoter.

78. The rAAV of any one of paragraphs 71-77, wherein the rAAV comprises an AAV2 capsid or a AAV5 capsid.

79. A pharmaceutical composition comprising the rAAV of any one of paragraphs 71-78, and at least one pharmaceutically or veterinarily acceptable carrier, excipient, or vehicle.

80. A method of treating a mammalian subject suffering from osteoarthritis, comprising, intra-articularly administering to said mammalian subject a therapeutically effective amount of the pharmaceutical composition of paragraph 79.

81. The method of paragraph 80, wherein the mammalian subject is a human or canine animal.

82. An isolated nucleic acid having the sequence set forth in SEQ ID NO: 4.

83. An isolated polypeptide having the sequence set forth in SEQ ID NO: 5.

The invention will now be detailed according to the following set of non-limiting claims.

What is claimed is:

1. A recombinant adeno-associated virus (rAAV) comprising a rAAV vector, wherein the rAAV vector comprises a DNA genome comprising a nucleic acid sequence encoding a canine hyaluronan synthase 2 (HAS2) polypeptide operably linked to a promoter, wherein the rAAV comprises an AAV5 capsid, wherein the nucleic acid sequence encodes a HAS2 polypeptide comprising the amino acid sequence set forth in SEQ ID NO:2.

2. The rAAV of claim 1, wherein the nucleic acid sequence encoding the HAS2 polypeptide has the sequence as set forth in SEQ ID NO:3.

3. The rAAV of claim 2, wherein the promoter is selected from the group consisting of a CMV IE promoter, a RSV promoter, an HSV-1 TK promoter, a SV40 early promoter, a SV40 late promoter, a phosphoglycerate kinase gene promoter, a metallothionein gene promoter, an α-1 antitrypsin gene promoter, an albumin gene promoter, a collagenase gene promoter, an elastase I gene promoter, a chicken beta-actin (CBA) promoter, β-actin gene promoter, β-globin gene promoter, a γ-globin gene promoter, an α-fetoprotein gene promoter, and a muscle creatine kinase gene promoter.

4. A pharmaceutical composition comprising the rAAV of claim 1, and optionally at least one pharmaceutically or veterinarily acceptable carrier, excipient, or vehicle.

5. A method of treating a mammalian subject suffering from osteoarthritis (OA), comprising intra-articularly administering to said mammalian subject a therapeutically effective amount of a recombinant adeno-associated virus (rAAV) comprising an rAAV vector, wherein the rAAV vector comprises a DNA genome comprising a nucleic acid encoding a canine hyaluronan synthase 2 (HAS2) polypeptide operably linked to a promoter, wherein the polypeptide is expressed in vivo in the mammalian subject in an amount effective to alleviate the symptoms of OA, wherein the rAAV comprises an AAV5 capsid, and wherein the nucleic acid encodes a HAS2 polypeptide comprising the amino acid sequence set forth in SEQ ID NO:2.

6. The method of claim 5, wherein the nucleic acid encoding the HAS2 polypeptide has the nucleotide sequence set forth in SEQ ID NO:3; and wherein the rAAV comprises a rAAV vector genome comprising from 5' to 3' the following elements: 5' AAV inverted terminal repeat (ITR), stuffer nucleic acid, a promoter, an intron (IN), a cHAS2 codon-optimized cDNA, a polyadenylation signal (pA), and a 3' AAV ITR.

7. A method of increasing the production of hyaluronic acid in chondrocytes and/or synoviocytes of a canine, comprising the steps of administering a rAAV to the canine, wherein the rAAV comprises a rAAV vector, wherein the rAAV vector comprises a DNA genome comprising nucleic acid encoding an HAS2 polypeptide operably linked to a promoter, wherein the rAAV comprises an AAV5 capsid, and wherein following administration the HAS2 polypeptide is expressed and catalyzes the production of additional hyaluronic acid, thereby increasing the level of hyaluronic acid (HA) in the canine, wherein the HAS2 polypeptide comprises the amino acid sequence set forth in SEQ ID NO:2.

8. The method of claim 7, wherein the HAS2 is produced in sufficient quantity to treat the symptoms of OA in canine.

9. The method of claim 7, wherein the HA levels are restored to levels found in healthy canines.

10. The method of claim 7, wherein the nucleic acid encoding the HAS2 polypeptide has the nucleotide sequence set forth in SEQ ID NO:3; and
   wherein the rAAV comprises a rAAV vector genome comprising from 5' to 3' the following elements: 5' AAV inverted terminal repeat (ITR), stuffer nucleic acid, a promoter, an intron (IN), a cHAS2 codon-optimized cDNA, a polyadenylation signal (pA), and a 3' AAV ITR.

11. The rAAV of claim 1, wherein the rAAV vector comprises a CBA-HI-cHAS2-BGHpA expression cassette.

12. The rAAV or claim 1, wherein the DNA genome is single-stranded.

* * * * *

SEQUENCE LISTING

<160> NUMBER OF SEQ ID NOS: 12

<210> SEQ ID NO 1
<211> LENGTH: 1656
<212> TYPE: DNA
<213> ORGANISM: Artificial Sequence
<220> FEATURE:
<223> OTHER INFORMATION: Canine hyaluronic acid synthase 2 (cHAS2) - GenBank XM 539153.3

<400> SEQUENCE: 1

| | | | | | | |
|---|---|---|---|---|---|---|
| atgcattgtg | agaggtttct | atgcatcctg | agaataattg | gaaccacact | ttttggagtg | 60 |
| tctctcctcc | ttggaatcac | agctgcttac | attgttggct | accaatttat | ccaaacagat | 120 |
| aattactact | tctcttttgg | actgtatggt | gccttttag | catcacacct | catcatccaa | 180 |
| agcctgtttg | cctttttgga | gcatcgaaaa | atgaagaaat | ccctagaaac | acccatcaaa | 240 |
| ttgaacaaga | ctgttgctct | tgcatcgct | gccatcaag | aagatccaga | ctacttacga | 300 |
| aaatgtttgc | aatctgtgaa | gaggctaacc | taccctggga | ttaaagttgt | catggtcata | 360 |
| gatgggaact | cggaagatga | cctttatatg | atggacatct | ttagcgaagt | catgggcagg | 420 |
| gacaaatcag | ccacttatat | ctggaagaac | aacttccacg | agaaaggtcc | tggtgagacg | 480 |
| gatgagtcac | ataaagaaag | ctcgcaacat | gtcacccagt | tggtcttgtc | aacaaaagt | 540 |
| atttgcatca | tgcaaaaatg | gggtggaaaa | agagaagtca | tgtacacggc | cttcagagca | 600 |
| ctgggacgaa | gtgtggatta | tgtacaggtt | tgtgattcag | acaccatgct | tgaccctgcc | 660 |
| tcatctgtgg | agatggtgaa | agttttagaa | gaagacccca | tggttggagg | tgtcggggga | 720 |
| gatgtccaga | ttttaaacaa | gtatgattcc | tggatctcct | tcctcagcag | tgtgagatac | 780 |
| tggatggctt | ttaacataga | aagggcctgc | cagtcttatt | ttgggtgtgt | ccagtgcatt | 840 |
| agtggacctc | tgggaatgta | cagaaactcc | ttgctgcatg | aatttgtgga | agactggtac | 900 |
| aatcaggaat | ttatgggcag | ccaatgtagt | tttggggacg | accggcatct | aacgaaccga | 960 |
| gtgctgagtc | tgggctatgc | aacaaaatac | acagctcgat | ccaagtgcct | acggagacg | 1020 |
| cctatagagt | atctcagatg | gttaaaccag | cagacccgct | ggagcaagtc | ctacttccga | 1080 |
| gagtggctgt | acaatgcgat | gtggttccat | aaacatcact | tgtggatgac | ctatgaggcc | 1140 |
| gttatcactg | gattcttccc | tttctttctc | attgccacag | tgatccagct | cttctacagg | 1200 |
| ggtaaaattt | ggaacatcct | cctcttcttg | ttaactgtcc | agttagtagg | tctcataaaa | 1260 |
| tcctcctttg | ccagctgcct | tagaggaaat | attgtcatgg | tcttcatgtc | cctctactca | 1320 |
| gtgctataca | tgtcaagttt | acttcctgcc | aaaatgttg | ccattgccac | gataaacaaa | 1380 |
| gctgggtggg | gcacatctgg | aaggaaaacc | attgtcgtta | atttcatagg | actcattcca | 1440 |
| gtatcggttt | ggtttacaat | cctcctgggt | ggtgtgattt | tcaccatttta | taaggaatct | 1500 |
| aaaaagccat | tctcagaatc | caagcagaca | gttctcattg | ttggaacgtt | gctctatgca | 1560 |
| tgctattggg | tcatgctttt | gacgctgtat | gtggttctca | tcaataagtg | tggcaggagg | 1620 |
| aagaagggac | aacagtatga | catggtgctc | gatgta | | | 1656 |

<210> SEQ ID NO 2
<211> LENGTH: 552
<212> TYPE: PRT
<213> ORGANISM: Artificial Sequence
<220> FEATURE:
<223> OTHER INFORMATION: cHAS2 polypeptide

<400> SEQUENCE: 2

Met His Cys Glu Arg Phe Leu Cys Ile Leu Arg Ile Ile Gly Thr Thr
1               5                   10                  15

Leu Phe Gly Val Ser Leu Leu Leu Gly Ile Thr Ala Ala Tyr Ile Val
            20                  25                  30

Gly Tyr Gln Phe Ile Gln Thr Asp Asn Tyr Tyr Phe Ser Phe Gly Leu
        35                  40                  45

Tyr Gly Ala Phe Leu Ala Ser His Leu Ile Ile Gln Ser Leu Phe Ala
    50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Gln Ser Val Lys Arg Leu Thr Tyr Pro
            100                 105                 110

Gly Ile Lys Val Val Met Val Ile Asp Gly Asn Ser Glu Asp Asp Leu
        115                 120                 125

Tyr Met Met Asp Ile Phe Ser Glu Val Met Gly Arg Asp Lys Ser Ala
    130                 135                 140

Thr Tyr Ile Trp Lys Asn Asn Phe His Glu Lys Gly Pro Gly Glu Thr
145                 150                 155                 160

Asp Glu Ser His Lys Glu Ser Ser Gln His Val Thr Gln Leu Val Leu
                165                 170                 175

Ser Asn Lys Ser Ile Cys Ile Met Gln Lys Trp Gly Gly Lys Arg Glu
            180                 185                 190

Val Met Tyr Thr Ala Phe Arg Ala Leu Gly Arg Ser Val Asp Tyr Val
    195                 200                 205

Gln Val Cys Asp Ser Asp Thr Met Leu Asp Pro Ala Ser Ser Val Glu
210                 215                 220

Met Val Lys Val Leu Glu Glu Asp Pro Met Val Gly Gly Val Gly Gly
225                 230                 235                 240

Asp Val Gln Ile Leu Asn Lys Tyr Asp Ser Trp Ile Ser Phe Leu Ser
                245                 250                 255

Ser Val Arg Tyr Trp Met Ala Phe Asn Ile Glu Arg Ala Cys Gln Ser
            260                 265                 270

Tyr Phe Gly Cys Val Gln Cys Ile Ser Gly Pro Leu Gly Met Tyr Arg
    275                 280                 285

Asn Ser Leu Leu His Glu Phe Val Glu Asp Trp Tyr Asn Gln Glu Phe
290                 295                 300

Met Gly Ser Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
            340                 345                 350

Arg Trp Ser Lys Ser Tyr Phe Arg Glu Trp Leu Tyr Asn Ala Met Trp
    355                 360                 365

Phe His Lys His His Leu Trp Met Thr Tyr Glu Ala Val Ile Thr Gly
370                 375                 380

Phe Phe Pro Phe Phe Leu Ile Ala Thr Val Ile Gln Leu Phe Tyr Arg
385                 390                 395                 400

Gly Lys Ile Trp Asn Ile Leu Leu Phe Leu Leu Thr Val Gln Leu Val
                405                 410                 415

Gly Leu Ile Lys Ser Ser Phe Ala Ser Cys Leu Arg Gly Asn Ile Val

```
                420             425             430
Met Val Phe Met Ser Leu Tyr Ser Val Leu Tyr Met Ser Ser Leu Leu
                    435                 440                 445

Pro Ala Lys Met Phe Ala Ile Ala Thr Ile Asn Lys Ala Gly Trp Gly
            450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
                        485                 490                 495

Tyr Lys Glu Ser Lys Lys Pro Phe Ser Glu Ser Lys Gln Thr Val Leu
                500                 505                 510

Ile Val Gly Thr Leu Leu Tyr Ala Cys Tyr Trp Val Met Leu Leu Thr
                    515                 520                 525

Leu Tyr Val Val Leu Ile Asn Lys Cys Gly Arg Arg Lys Lys Gly Gln
                530                 535                 540

Gln Tyr Asp Met Val Leu Asp Val
545                 550
```

<210> SEQ ID NO 3
<211> LENGTH: 1656
<212> TYPE: DNA
<213> ORGANISM: Artificial Sequence
<220> FEATURE:
<223> OTHER INFORMATION: Codon-optimized cHAS2

<400> SEQUENCE: 3

```
atgcactgcg agcggtttct gtgcatcctg aggatcatcg caccaccct gttcggcgtg      60
tccctgctgc tgggcatcac cgccgcctac atcgtgggct accagttcat ccagaccgac     120
aactactact tcagcttcgg cctgtacggc gccttcctgg ccagccacct gatcatccag     180
agcctgttcg ccttcctcga gcaccggaag atgaagaagt ccctggaaac ccccatcaag     240
ctgaacaaga ccgtggccct gtgtatcgct gcctaccagg aagatcccga ctacctgcgg     300
aagtgcctgc agagcgtgaa gaggctgacc taccccggca tcaaggtggt catggtcatc     360
gacggcaaca gcgaggacga cctgtacatg atggacatct tcagcgaagt gatgggcagg     420
gacaagagcg ccacctacat ctggaagaac aacttccacg agaagggccc tggcgaaacc     480
gacgagagca caaagaaag cagccagcac gtgacccagc tggtgctgag caacaagagc     540
atctgcatca tgcagaagtg gggcggcaag agggaagtga tgtacaccgc cttcagagcc     600
ctgggcagaa gcgtggacta cgtccaagtg tgcgacagcg acaccatgct ggaccccgcc     660
agcagcgtgg aaatggtcaa ggtgctggaa gaggacccca tggtcggagg cgtgggcggc     720
gacgtgcaga tcctgaacaa atacgacagc tggatcagct tcctgagcag cgtgcggtac     780
tggatggcct tcaacatcga gagggcctgc cagagctact cggctgcgt gcagtgcatc     840
agcggccctc tggcatgta ccggaacagc ctgctgcacg agttcgtcga ggactggtac     900
aaccaggaat tcatgggcag ccagtgcagc ttcggcgacg acaggcacct gaccaacagg     960
gtgctgagcc tgggctacgc caccaagtac accgccaggt ccaagtgcct gaccgagaca    1020
cccatcgagt acctgcggtg gctgaaccag cagaccaggt ggtccaagtc ctacttcaga    1080
gagtggctgt acaacgccat ggttccac aagcaccacc tgtggatgac ctacgaggcc    1140
gtgatcaccg gattcttccc tttcttcctg atcgccaccg tgattcagct gttctacagg    1200
ggcaagatct ggaatatcct gctgttcctg ctgaccgtcc agctcgtggg cctgatcaag    1260
agcagcttcg ccagctgcct gagggcaac atcgtgatgg tgttcatgag cctgtacagc    1320
```

| | |
|---|---:|
| gtgctgtaca tgtcctccct gctgcccgcc aagatgttcg ccattgccac catcaacaag | 1380 |
| gccggctggg gcacaagcgg cagaaagacc atcgtggtca acttcatcgg cctgatcccc | 1440 |
| gtgtccgtgt ggttcaccat cctgctgggc ggcgtgatct tcaccatcta caaagagagc | 1500 |
| aagaagccct tcagcgagag caagcagacc gtgctgatcg tgggaaccct gctgtacgcc | 1560 |
| tgctactggg tcatgctgct gaccctgtac gtggtgctga ttaacaagtg cggcaggcgg | 1620 |
| aagaagggcc agcagtacga catggtgctg gacgtg | 1656 |

```
<210> SEQ ID NO 4
<211> LENGTH: 4020
<212> TYPE: DNA
<213> ORGANISM: Artificial Sequence
<220> FEATURE:
<223> OTHER INFORMATION: Canine Full length lubricin

<400> SEQUENCE: 4
```

| | |
|---|---:|
| atgcagtgga aaatacttcc catatacttg ctgctcctct ctgttttctt gattcagcaa | 60 |
| gtttcttctc aagatttacc aagctgtgca gggagatgtg gggaagggta ttctagagat | 120 |
| gccatctgca actgtgatta taactgtcaa cactacatgg agtgctgccc tgatttcaag | 180 |
| aaagcctgca ctgtggagct ttcctgtaaa ggtcgctgct tcgagtcctt tgcacgaggg | 240 |
| agggagtgtg actgtgactc agactgtaag aagtatggca agtgctgtcc cgattatgag | 300 |
| gattttgtg gaagagtgca taatcccaca tcacctccat cttcaaagac tgcacctcca | 360 |
| tctccaggag catctcaaac catcaaatca acagccaaac gttcacccaa agcaccaaat | 420 |
| aagaagaaga ctaagaaagt tatagaatca gaggaaataa cagaagaaca ttctgtttct | 480 |
| gaaaaccaag agtcttcttc ctcctcttcc tcttcctctt caactattcg aaaaatcaag | 540 |
| tcttccaaaa attcagcagc taataaagaa ttaagaagaa acccaaagt aaaagataac | 600 |
| aagaaggaaa gaactcctaa aaagaaacct ccgccagaac caccagttgt agatgaagct | 660 |
| ggaagtggac tggacaatgg tgacatcaag ctcaccccca ctcctgacat tcctaccacc | 720 |
| caacgcaata aggttaccac atctcccaag tttacaacag gcaaaccaat aaatcctaaa | 780 |
| cctagtcttc cacctaatac tgatacatcc aaagagacct cttcaacacc taataaggag | 840 |
| acaacagtga aaagtaaaga actttagca acaaagaga cttcaagtaa agcaaaagag | 900 |
| aagattactt cagccaaaga gacacgaagt gcagagaaaa cacctgctaa agattttgta | 960 |
| cccacaacca agctcctgt taaatctaca cccaaagctg aaagtacaac caaatctcct | 1020 |
| gctcccacca ccaccaagga gcccactcct accaccacca agaagcctgc acccactacc | 1080 |
| cccaagaaac ctgctcccac tactcccaag gagcctgtac ccactaccac caaggggcca | 1140 |
| cccaccacgc ccaagaaacc tgaacccacc actcccaagg atcctgctcc caccaccacc | 1200 |
| aaggagccca ctcccaccac ccccaagaag cctgctccca ctactcccaa ggagcctgta | 1260 |
| cccattacca ccaaggagcc tgaacccacc accccaaga gcctgaacc caccactccc | 1320 |
| aaggagcctg ctcccaccac tcccaaggag cctgtaccca ctaccaccaa ggagcctgaa | 1380 |
| cccaccactc ccaaggagcc tgcacccacc accccaagg agcctgctcc cactactccc | 1440 |
| aaggagccta cctactactc accaaggag ccacccacca cccccaagaa gcctgaaccc | 1500 |
| accactccca aggagcctgc tccaccact cccaaggagc ctgtacccac taccaccaag | 1560 |
| gagcctgaac ccaccactcc caaggagctt gcacccacca cccccaagga gcctgctccc | 1620 |
| actactccca aggagcctgt acctactacc accaaggagc cacccaccac ccccaagaag | 1680 |

-continued

```
cctgaaccca ccactcccaa ggagcctgca cccaccaccc ccaaggagcc tgctcccact    1740
actcccaagg agccacctac cacccccaag aagcctgaac ccaccactcc caaagaggct    1800
gctcccacca ccaagaaacc agctgccacc actcccaagg agcctgcacc cactatcact    1860
aaggagcctg caccaactac tcccaacaag cctgaaccca ccactcccaa agagcctgtg    1920
cccacaaccc ccaaggagcc tgaacccact cccctaagg aacctgctcc taccaccacc    1980
aaggaccctg cacctaccag tcccaaggaa cctactccca ccgccccaa ggagcctgta    2040
cctactgccc caaggagcc tgaacccatg gccccaaga agcctgtacc cactgccccc    2100
aagcagccta cacccaccac ccccaaggag ccttcaccca ctgtcccaa ggagcctgaa    2160
cctatggccc caaggagcc tgtacccaca gctcccaaga acctgcacc caccgccccc    2220
aaggaccctg cacccaccgc ccccaaggag cctgaaccca ctgccccaa taaggaatct    2280
gcacccacca catccaagga acaggttccc atcaccacca aggagcccac acccaaactc    2340
ccgaaggagc ctgctccagc ctctcttgag acgcctgctc caaccacctc agacgccttt    2400
actacaacta cgactatgga gcctcccact actcccaaga accctgctga gtcaactcct    2460
aagtttcctg cagaacccac accaaagcct cttgaaaaca gtcccaaaga accagttgta    2520
cctataacca aggctcctga agtgaccaaa cctgaaatga ctacaacagc taaagataaa    2580
acaacagaaa aagacataat acctgaaatt acaactgctg tacctaagat tacaacccag    2640
gagacagcaa ctccaacaga agaaacgacc actgagtcca aaacaagtac aaccacacaa    2700
gtaacatcta ccacatcatc caaaaacact cctaaagcaa caactctcgc acccaaagta    2760
atgactgcaa cacaaaagac aactacaact gaagagacta tgaataaacc tgaagaaacc    2820
acagctgtgc caaggatac agctacgagt actaaagtct caactcctag accccgaaag    2880
ccaaccaaag caccaaagaa gcccacttct accaaaaagc caaacacaat acctaaagaa    2940
aaaaaaccaa agactacacc aactccccca agatgactac tcgacaat gcccaaatta    3000
cacctacct cttcagtgga agccatgctc caaactacca ccagccccaa ccaaagacct    3060
aactcagaaa tagttgaagt aaatccaaat gaagatacag atgctgctgg aaaaaaacct    3120
cacatgttcc ccaggccccc tgtgttaact cctatattta tcccagggac tgatatctta    3180
gtgagaggat ccaatcaaga cattgccatc aatcccatgc tttcagatga gactaattta    3240
tgcaacggta agccagtaga tggactgact actttgcgca atggaaccat ggtcgcattt    3300
cgaggtcatt atttctggat gctgagtcca tccaatccac catctccacc tcgtaaaatt    3360
actgaagttt ggggtattcc ctcccccatt gatactgttt ttactaggtg caactgtgaa    3420
ggaaaaactt tcttctttaa gggttcccag tactggcgtt tcaccaatga tataaaagat    3480
gcagggtatc ccaaacaaat tgtaaaagga tttggaggac taaatggaag aatagtggca    3540
gctctctcaa tagctaaata caaggacaga cctgaatctg tgtattttt caagagaggt    3600
ggcagcgttc agcagtacac ttataaacag gaacccatca aaaagtgcac tggaagaagg    3660
cccgctatca attacccagt gtatggagaa acaacacagg ttagaagacg tcgctttgaa    3720
cgcgccatag gaccttctca aacacacacc atcagaattc actattcacc catcagagtc    3780
tcttatcaag ataaaggttt cctccataat gaagtcaaaa tgagttcaca gtggagagga    3840
tttccaaatg tggttacttc agctatagca ctgcccaaca tcagaaaacc tgatggctat    3900
gattactacg cctttctag gaatcaatac tataacattg atgtacccag cagaacagca    3960
agagttgtta ctactcgttt tgggaggacc ttatccaata tctggtacaa ctgtccttag    4020
```

-continued

```
<210> SEQ ID NO 5
<211> LENGTH: 1339
<212> TYPE: PRT
<213> ORGANISM: Artificial Sequence
<220> FEATURE:
<223> OTHER INFORMATION: full-length lubricin polypeptide - translation
      of SEQ ID NO: 4

<400> SEQUENCE: 5

Met Gln Trp Lys Ile Leu Pro Ile Tyr Leu Leu Leu Ser Val Phe
1               5                   10                  15

Leu Ile Gln Gln Val Ser Ser Gln Asp Leu Pro Ser Cys Ala Gly Arg
                20                  25                  30

Cys Gly Glu Gly Tyr Ser Arg Asp Ala Ile Cys Asn Cys Asp Tyr Asn
                35                  40                  45

Cys Gln His Tyr Met Glu Cys Cys Pro Asp Phe Lys Lys Ala Cys Thr
        50                  55                  60

Val Glu Leu Ser Cys Lys Gly Arg Cys Phe Glu Ser Phe Ala Arg Gly
65                  70                  75                  80

Arg Glu Cys Asp Cys Asp Ser Asp Cys Lys Tyr Gly Lys Cys Cys
                    85                  90                  95

Pro Asp Tyr Glu Asp Phe Cys Gly Arg Val His Asn Pro Thr Ser Pro
                100                 105                 110

Pro Ser Ser Lys Thr Ala Pro Pro Ser Pro Gly Ala Ser Gln Thr Ile
                115                 120                 125

Lys Ser Thr Ala Lys Arg Ser Pro Lys Ala Pro Asn Lys Lys Lys Thr
        130                 135                 140

Lys Lys Val Ile Glu Ser Glu Glu Ile Thr Glu Glu His Ser Val Ser
145                 150                 155                 160

Glu Asn Gln Glu Ser Ser Ser Ser Ser Ser Ser Ser Ser Thr Ile
                165                 170                 175

Arg Lys Ile Lys Ser Ser Lys Asn Ser Ala Ala Asn Lys Glu Leu Lys
                180                 185                 190

Lys Lys Pro Lys Val Lys Asp Asn Lys Lys Glu Arg Thr Pro Lys Lys
        195                 200                 205

Lys Pro Pro Pro Glu Pro Val Val Asp Glu Ala Gly Ser Gly Leu
        210                 215                 220

Asp Asn Gly Asp Ile Lys Leu Thr Pro Thr Pro Asp Ile Pro Thr Thr
225                 230                 235                 240

Gln Arg Asn Lys Val Thr Thr Ser Pro Lys Phe Thr Thr Gly Lys Pro
                245                 250                 255

Ile Asn Pro Lys Pro Ser Leu Pro Pro Asn Thr Asp Thr Ser Lys Glu
                260                 265                 270

Thr Ser Thr Pro Asn Lys Glu Thr Thr Val Lys Ser Lys Glu Thr
        275                 280                 285

Leu Ala Asn Lys Glu Thr Ser Ser Lys Ala Lys Glu Lys Ile Thr Ser
        290                 295                 300

Ala Lys Glu Thr Arg Ser Ala Glu Lys Thr Pro Ala Lys Asp Phe Val
305                 310                 315                 320

Pro Thr Thr Lys Ala Pro Val Lys Ser Thr Pro Lys Ala Glu Ser Thr
                325                 330                 335

Thr Lys Ser Pro Ala Pro Thr Thr Lys Glu Pro Thr Pro Thr Thr
        340                 345                 350

Thr Lys Lys Pro Ala Pro Thr Thr Pro Lys Lys Pro Ala Pro Thr Thr
        355                 360                 365
```

-continued

```
Pro Lys Glu Pro Val Pro Thr Thr Lys Gly Pro Pro Thr Thr Pro
    370                 375                 380
Lys Lys Pro Glu Pro Thr Thr Pro Lys Asp Pro Ala Pro Thr Thr Thr
385                 390                 395                 400
Lys Glu Pro Thr Pro Thr Thr Pro Lys Lys Pro Ala Pro Thr Thr Pro
                405                 410                 415
Lys Glu Pro Val Pro Ile Thr Thr Lys Glu Pro Gly Pro Thr Thr Pro
                420                 425                 430
Lys Lys Pro Glu Pro Thr Thr Pro Lys Glu Pro Ala Pro Thr Thr Pro
                435                 440                 445
Lys Glu Pro Val Pro Thr Thr Lys Glu Pro Glu Pro Thr Thr Pro
                450                 455                 460
Lys Glu Pro Ala Pro Thr Thr Pro Lys Glu Pro Ala Pro Thr Thr Pro
465                 470                 475                 480
Lys Glu Pro Val Pro Thr Thr Lys Glu Pro Pro Thr Thr Pro Lys
                485                 490                 495
Lys Pro Glu Pro Thr Thr Pro Lys Glu Pro Ala Pro Thr Thr Pro Lys
            500                 505                 510
Glu Pro Val Pro Thr Thr Lys Glu Pro Glu Pro Thr Thr Pro Lys
            515                 520                 525
Glu Leu Ala Pro Thr Thr Pro Lys Glu Pro Ala Pro Thr Thr Pro Lys
        530                 535                 540
Glu Pro Val Pro Thr Thr Lys Glu Pro Pro Thr Thr Pro Lys Lys
545                 550                 555                 560
Pro Glu Pro Thr Thr Pro Lys Glu Pro Ala Pro Thr Thr Pro Lys Glu
                565                 570                 575
Pro Ala Pro Thr Thr Pro Lys Glu Pro Pro Thr Thr Pro Lys Lys Pro
                580                 585                 590
Glu Pro Thr Thr Pro Lys Glu Ala Ala Pro Thr Thr Lys Lys Pro Ala
                595                 600                 605
Ala Thr Thr Pro Lys Glu Pro Ala Pro Thr Ile Thr Lys Glu Pro Ala
        610                 615                 620
Pro Thr Thr Pro Asn Lys Pro Glu Pro Thr Thr Pro Lys Glu Pro Val
625                 630                 635                 640
Pro Thr Thr Pro Lys Glu Pro Glu Pro Thr Pro Pro Lys Glu Pro Ala
                645                 650                 655
Pro Thr Thr Thr Lys Asp Pro Ala Pro Thr Ser Pro Lys Glu Pro Thr
                660                 665                 670
Pro Thr Ala Pro Lys Glu Pro Val Pro Thr Ala Pro Lys Glu Pro Glu
                675                 680                 685
Pro Met Ala Pro Lys Lys Pro Val Pro Thr Ala Pro Lys Gln Pro Thr
                690                 695                 700
Pro Thr Thr Pro Lys Glu Pro Ser Pro Thr Val Pro Lys Glu Pro Glu
705                 710                 715                 720
Pro Met Ala Pro Lys Glu Pro Val Pro Thr Ala Pro Lys Lys Pro Ala
                725                 730                 735
Pro Thr Ala Pro Lys Asp Pro Ala Pro Thr Ala Pro Lys Glu Pro Glu
                740                 745                 750
Pro Thr Ala Pro Asn Lys Glu Ser Ala Pro Thr Thr Ser Lys Glu Gln
                755                 760                 765
Val Pro Ile Thr Thr Lys Glu Pro Thr Pro Lys Leu Pro Lys Glu Pro
            770                 775                 780
Ala Pro Ala Ser Leu Glu Thr Pro Ala Pro Thr Thr Ser Asp Ala Phe
```

-continued

```
            785                 790                 795                 800
        Thr Thr Thr Thr Thr Met Glu Pro Pro Thr Thr Pro Lys Asn Pro Ala
                        805                 810                 815
        Glu Ser Thr Pro Lys Phe Pro Ala Glu Pro Thr Pro Lys Pro Leu Glu
                        820                 825                 830
        Asn Ser Pro Lys Glu Pro Val Val Pro Ile Thr Lys Ala Pro Glu Val
                        835                 840                 845
        Thr Lys Pro Glu Met Thr Thr Ala Lys Asp Lys Thr Thr Glu Lys
                850                     855                 860
        Asp Ile Ile Pro Glu Ile Thr Thr Ala Val Pro Lys Ile Thr Thr Gln
        865                 870                 875                 880
        Glu Thr Ala Thr Pro Thr Glu Glu Thr Thr Thr Glu Ser Lys Thr Ser
                            885                 890                 895
        Thr Thr Thr Gln Val Thr Ser Thr Thr Ser Ser Lys Asn Thr Pro Lys
                        900                 905                 910
        Ala Thr Thr Leu Ala Pro Lys Val Met Thr Ala Thr Gln Lys Thr Thr
                        915                 920                 925
        Thr Thr Glu Glu Thr Met Asn Lys Pro Glu Glu Thr Thr Ala Val Pro
                930                 935                 940
        Lys Asp Thr Ala Thr Ser Thr Lys Val Ser Thr Pro Arg Pro Arg Lys
        945                 950                 955                 960
        Pro Thr Lys Ala Pro Lys Lys Pro Thr Ser Thr Lys Lys Pro Asn Thr
                            965                 970                 975
        Ile Pro Lys Arg Lys Lys Pro Lys Thr Thr Pro Thr Pro Lys Met
                        980                 985                 990
        Thr Thr Ser Thr Met Pro Lys Leu  His Pro Thr Ser  Ser  Val Glu Ala
                        995                 1000                1005
        Met Leu  Gln Thr Thr Thr Ser  Pro Asn Gln Arg Pro  Asn Ser Glu
                1010                1015                1020
        Ile Val  Glu Val Asn Pro Asn  Glu Asp Thr Asp Ala  Ala Gly Lys
                1025                1030                1035
        Lys Pro  His Met Phe Pro Arg  Pro Pro Val Leu Thr  Pro Ile Phe
                1040                1045                1050
        Ile Pro  Gly Thr Asp Ile Leu  Val Arg Gly Ser Asn  Gln Asp Ile
                1055                1060                1065
        Ala Ile  Asn Pro Met Leu Ser  Asp Glu Thr Asn Leu  Cys Asn Gly
                1070                1075                1080
        Lys Pro  Val Asp Gly Leu Thr  Thr Leu Arg Asn Gly  Thr Met Val
                1085                1090                1095
        Ala Phe  Arg Gly His Tyr Phe  Trp Met Leu Ser Pro  Ser Asn Pro
                1100                1105                1110
        Pro Ser  Pro Pro Arg Lys Ile  Thr Glu Val Trp Gly  Ile Pro Ser
                1115                1120                1125
        Pro Ile  Asp Thr Val Phe Thr  Arg Cys Asn Cys Glu  Gly Lys Thr
                1130                1135                1140
        Phe Phe  Phe Lys Gly Ser Gln  Tyr Trp Arg Phe Thr  Asn Asp Ile
                1145                1150                1155
        Lys Asp  Ala Gly Tyr Pro Lys  Gln Ile Val Lys Gly  Phe Gly Gly
                1160                1165                1170
        Leu Asn  Gly Arg Ile Val Ala  Ala Leu Ser Ile Ala  Lys Tyr Lys
                1175                1180                1185
        Asp Arg  Pro Glu Ser Val Tyr  Phe Phe Lys Arg Gly  Gly Ser Val
                1190                1195                1200
```

Gln Gln Tyr Thr Tyr Lys Gln Glu Pro Ile Lys Lys Cys Thr Gly
    1205              1210                 1215

Arg Arg Pro Ala Ile Asn Tyr Pro Val Tyr Gly Glu Thr Thr Gln
    1220              1225                 1230

Val Arg Arg Arg Arg Phe Glu Arg Ala Ile Gly Pro Ser Gln Thr
    1235              1240                 1245

His Thr Ile Arg Ile His Tyr Ser Pro Ile Arg Val Ser Tyr Gln
    1250              1255                 1260

Asp Lys Gly Phe Leu His Asn Glu Val Lys Met Ser Ser Gln Trp
    1265              1270                 1275

Arg Gly Phe Pro Asn Val Val Thr Ser Ala Ile Ala Leu Pro Asn
    1280              1285                 1290

Ile Arg Lys Pro Asp Gly Tyr Asp Tyr Tyr Ala Phe Ser Arg Asn
    1295              1300                 1305

Gln Tyr Tyr Asn Ile Asp Val Pro Ser Arg Thr Ala Arg Val Val
    1310              1315                 1320

Thr Thr Arg Phe Gly Arg Thr Leu Ser Asn Ile Trp Tyr Asn Cys
    1325              1330                 1335

Pro

<210> SEQ ID NO 6
<211> LENGTH: 2949
<212> TYPE: DNA
<213> ORGANISM: Artificial Sequence
<220> FEATURE:
<223> OTHER INFORMATION: Codon-optimized truncated cLub

<400> SEQUENCE: 6
atgcagtgga agatcctgcc tatctacctg ctcctgctga gcgtgttcct gatccagcaa    60
gtgtccagcc aggacctgcc cagctgcgcc ggaagatgcg gcgagggcta cagcagggac   120
gccatctgca actgcgacta caactgccag cactacatgg aatgctgccc cgacttcaag   180
aaggcctgca ccgtcgagct gagctgcaag ggccggtgct tcgagagctt cgccaggggc   240
agagagtgcg actgcgacag cgactgcaag aaatacggca gtgctgccc tgactacgag   300 gacttctgcg gcagggtgca aaccccccac cagcccccta gcagcaagac cgcccctcca   360
tctcctggcg ccagccagac catcaagagc accgccaaga gtcccccaa ggcccccaac   420 aagaaaaaga ccaagaaagt gatcgagagc gaggaaatca ccgaggaaca cagcgtgtcc   480
gagaatcaag agagcagcag cagctccagc tccagcagca gcaccatccg gaagatcaag   540
agcagcaaga acagcgccgc caacaaagag ctgaagaaga gcccaaagt caaggacaac   600 aagaaagagc ggacccccaa gaagaaaccc cccccagagc ccctgtggt ggatgaggcc   660 ggcagcggcc tggacaacgg cgacatcaag ctgacccca ccccgacat ccccaccacc   720 cagaggaaca agtgaccac ctcccccaag ttcaccaccg gcaagcccat caaccccaag   780
cccagcctgc cccccaacac cgacaccagc aagaaaacca gcagcacccc taacaaagag   840
acaaccgtca gagcaaaga gacactggct aacaagaaa cctccagcaa ggccaaagag   900
aagatcacca cgccaaaga gactcggagc gccgagaaaa cccccgccaa ggacttcgtg   960
cccaccacca aggccctgt gaagtccacc cctaaggccg agtctaccac caagagccct  1020 gccccccacca ccaccaaaga gccaaccct acaaccacca gaaaccgc tcctaccaca  1080 cccaagaagc cagccccaac tacccctaaa gaacccgtgc ctaccaccac aaagggccct  1140
cccacaaccc ctaagaaacc tgagcccacc accccccaagg acccgctcc cacaacaaca  1200

```
aaagagccca ccccccactac acccaaaaag cctgctccta caactcccaa agagcccgtc    1260
ccaaccacaa ccgagccagc ccctgccagc ctggaaaccc ctgcccctac taccagcgac    1320
gcgttcacca ccacaaccac catggaaccc ccaccactc ctaagaatcc cgccgagagc     1380
acccccaagt ttcccgccga gcctacccct aagcccctgg aaaacagccc caagaacct    1440 gtggtgccta tcaccaaagc ccccgaagtg accaagcccg agatgaccac cacagccaag   1500
gacaagacca ccgagaagga catcatccct gagatcacca ccgccgtgcc caaaatcacc   1560
acccaagaga cagccaccc caccgaggaa accaccaccg agagcaagac cagcaccacc    1620
acacaagtga cctccaccac aagctccaag aaccccca aagccaccac cctggccccc    1680
aaagtgatga ccgccaccca gaaaaccact accaccgaag agactatgaa caagcccgaa   1740
gagacaacag ccgtgcctaa ggacaccgcc acctccacca aggtgtccac ccccagaccc   1800
cggaagccca ccaaggctcc aaagaagccc acctctacca agaagcctaa caccatcccc   1860
aagaggaaga aacccaagac cacccctacc cccccaagat gacaaccag caccatgccc    1920 aagctgcacc ccacctccag cgtggaagcc atgctgcaga ccaccacctc tcccaaccag   1980
aggcccaaca gcgagatcgt ggaagtgaac cccaacgagg acaccgacgc cgctggcaag   2040
aaaccccaca tgttccccag gcctcccgtg ctgacccctc tcttcatccc cggcaccgac   2100
atcctcgtgc ggggcagcaa ccaggatatc gccatcaacc ctatgctgag cgacgagaca   2160
aacctgtgca acggcaagcc cgtggacggc ctgaccaccc tgagaaacgg caccatggtg   2220
gccttcaggg gccactactt ctggatgctg agccccagca accctcccag ccctcctcgg   2280
aagatcaccg aagtgtgggg catccccagc cccatcgaca ccgtgttcac caggtgcaat   2340
tgcgagggca agacattctt cttcaagggc tcccaatact ggcggttcac caacgacatc   2400
aaggacgccg gctaccccaa gcagatcgtg aagggcttcg gcggcctgaa cggcaggatc   2460
gtggccgccc tgtctatcgc caagtacaag gacaggcccg agagcgtgta cttcttcaag   2520
aggggcggca gcgtgcagca gtacacctac aagcaagagc ccatcaagaa gtgcaccggc   2580
agaaggcccg ccatcaacta ccccgtgtac ggcgaaacca cccaagtgcg gaggcggaga   2640
ttcgagaggg ccatcggccc tagccagacc cacaccatca ggatccacta cagcccatc    2700 agggtgtcct accaggacaa gggcttcctg cacaacgaag tgaagatgag cagccagtgg   2760
cggggcttcc ccaacgtcgt gaccagcgcc attgccctgc caacatccg gaagcccgac    2820 ggctacgact actacgcctt cagccggaac cagtactaca acatcgacgt gcccagcagg   2880
accgccaggg tggtcaccac cagattcggc aggaccctga gcaacatctg gtacaactgc   2940
ccctgatga                                                          2949
```

<210> SEQ ID NO 7
<211> LENGTH: 981
<212> TYPE: PRT
<213> ORGANISM: Artificial Sequence
<220> FEATURE:
<223> OTHER INFORMATION: Truncated codon-optimized cLUB polypeptide - translation of SEQ ID NO: 6

<400> SEQUENCE: 7

Met Gln Trp Lys Ile Leu Pro Ile Tyr Leu Leu Leu Ser Val Phe
1               5                   10                  15

Leu Ile Gln Gln Val Ser Ser Gln Asp Leu Pro Ser Cys Ala Gly Arg
            20                  25                  30

Cys Gly Glu Gly Tyr Ser Arg Asp Ala Ile Cys Asn Cys Asp Tyr Asn

-continued

```
                35                  40                  45
Cys Gln His Tyr Met Glu Cys Cys Pro Asp Phe Lys Lys Ala Cys Thr
 50                  55                  60
Val Glu Leu Ser Cys Lys Gly Arg Cys Phe Glu Ser Phe Ala Arg Gly
 65                  70                  75                  80
Arg Glu Cys Asp Cys Asp Ser Asp Cys Lys Lys Tyr Gly Lys Cys Cys
                 85                  90                  95
Pro Asp Tyr Glu Asp Phe Cys Gly Arg Val His Asn Pro Thr Ser Pro
            100                 105                 110
Pro Ser Ser Lys Thr Ala Pro Pro Ser Pro Gly Ala Ser Gln Thr Ile
            115                 120                 125
Lys Ser Thr Ala Lys Arg Ser Pro Lys Ala Pro Asn Lys Lys Lys Thr
            130                 135                 140
Lys Lys Val Ile Glu Ser Glu Glu Ile Thr Glu Glu His Ser Val Ser
145                 150                 155                 160
Glu Asn Gln Glu Ser Ser Ser Ser Ser Ser Ser Ser Ser Ser Thr Ile
                165                 170                 175
Arg Lys Ile Lys Ser Ser Lys Asn Ser Ala Ala Asn Lys Glu Leu Lys
            180                 185                 190
Lys Lys Pro Lys Val Lys Asp Asn Lys Lys Glu Arg Thr Pro Lys Lys
            195                 200                 205
Lys Pro Pro Pro Glu Pro Pro Val Val Asp Glu Ala Gly Ser Gly Leu
            210                 215                 220
Asp Asn Gly Asp Ile Lys Leu Thr Pro Thr Pro Asp Ile Pro Thr Thr
225                 230                 235                 240
Gln Arg Asn Lys Val Thr Thr Ser Pro Lys Phe Thr Gly Lys Pro
                245                 250                 255
Ile Asn Pro Lys Pro Ser Leu Pro Pro Asn Thr Asp Thr Ser Lys Glu
            260                 265                 270
Thr Ser Ser Thr Pro Asn Lys Glu Thr Thr Val Lys Ser Lys Glu Thr
            275                 280                 285
Leu Ala Asn Lys Glu Thr Ser Ser Lys Ala Lys Glu Lys Ile Thr Ser
            290                 295                 300
Ala Lys Glu Thr Arg Ser Ala Glu Lys Thr Pro Ala Lys Asp Phe Val
305                 310                 315                 320
Pro Thr Thr Lys Ala Pro Val Lys Ser Thr Pro Lys Ala Glu Ser Thr
                325                 330                 335
Thr Lys Ser Pro Ala Pro Thr Thr Thr Lys Glu Pro Thr Pro Thr Thr
            340                 345                 350
Thr Lys Lys Pro Ala Pro Thr Thr Pro Lys Lys Pro Ala Pro Thr Thr
            355                 360                 365
Pro Lys Glu Pro Val Pro Thr Thr Thr Lys Gly Pro Thr Thr Thr Pro
            370                 375                 380
Lys Lys Pro Glu Pro Thr Thr Pro Lys Asp Pro Ala Pro Thr Thr Thr
385                 390                 395                 400
Lys Glu Pro Thr Pro Thr Thr Pro Lys Lys Pro Ala Pro Thr Thr Pro
                405                 410                 415
Lys Glu Pro Val Pro Thr Thr Thr Glu Pro Ala Pro Ala Ser Leu Glu
            420                 425                 430
Thr Pro Ala Pro Thr Thr Ser Asp Ala Phe Thr Thr Thr Thr Thr Met
            435                 440                 445
Glu Pro Pro Thr Thr Pro Lys Asn Pro Ala Glu Ser Thr Pro Lys Phe
            450                 455                 460
```

```
Pro Ala Glu Pro Thr Pro Lys Pro Leu Glu Asn Ser Pro Lys Glu Pro
465                 470                 475                 480

Val Val Pro Ile Thr Lys Ala Pro Glu Val Thr Lys Pro Glu Met Thr
                485                 490                 495

Thr Thr Ala Lys Asp Lys Thr Thr Glu Lys Asp Ile Ile Pro Glu Ile
            500                 505                 510

Thr Thr Ala Val Pro Lys Ile Thr Thr Gln Glu Thr Ala Thr Pro Thr
            515                 520                 525

Glu Glu Thr Thr Thr Glu Ser Lys Thr Ser Thr Thr Thr Gln Val Thr
        530                 535                 540

Ser Thr Thr Ser Ser Lys Asn Thr Pro Lys Ala Thr Thr Leu Ala Pro
545                 550                 555                 560

Lys Val Met Thr Ala Thr Gln Lys Thr Thr Thr Glu Glu Thr Met
                565                 570                 575

Asn Lys Pro Glu Glu Thr Thr Ala Val Pro Lys Asp Thr Ala Thr Ser
            580                 585                 590

Thr Lys Val Ser Thr Pro Arg Pro Arg Lys Pro Thr Lys Ala Pro Lys
        595                 600                 605

Lys Pro Thr Ser Thr Lys Lys Pro Asn Thr Ile Pro Lys Arg Lys Lys
    610                 615                 620

Pro Lys Thr Thr Pro Thr Pro Pro Lys Met Thr Thr Ser Thr Met Pro
625                 630                 635                 640

Lys Leu His Pro Thr Ser Ser Val Glu Ala Met Leu Gln Thr Thr Thr
                645                 650                 655

Ser Pro Asn Gln Arg Pro Asn Ser Glu Ile Val Glu Val Asn Pro Asn
            660                 665                 670

Glu Asp Thr Asp Ala Ala Gly Lys Lys Pro His Met Phe Pro Arg Pro
        675                 680                 685

Pro Val Leu Thr Pro Ile Phe Ile Pro Gly Thr Asp Ile Leu Val Arg
    690                 695                 700

Gly Ser Asn Gln Asp Ile Ala Ile Asn Pro Met Leu Ser Asp Glu Thr
705                 710                 715                 720

Asn Leu Cys Asn Gly Lys Pro Val Asp Gly Leu Thr Thr Leu Arg Asn
            725                 730                 735

Gly Thr Met Val Ala Phe Arg Gly His Tyr Phe Trp Met Leu Ser Pro
            740                 745                 750

Ser Asn Pro Pro Ser Pro Pro Arg Lys Ile Thr Glu Val Trp Gly Ile
        755                 760                 765

Pro Ser Pro Ile Asp Thr Val Phe Thr Arg Cys Asn Cys Glu Gly Lys
    770                 775                 780

Thr Phe Phe Phe Lys Gly Ser Gln Tyr Trp Arg Phe Thr Asn Asp Ile
785                 790                 795                 800

Lys Asp Ala Gly Tyr Pro Lys Gln Ile Val Lys Gly Phe Gly Gly Leu
            805                 810                 815

Asn Gly Arg Ile Val Ala Ala Leu Ser Ile Ala Lys Tyr Lys Asp Arg
            820                 825                 830

Pro Glu Ser Val Tyr Phe Phe Lys Arg Gly Gly Ser Val Gln Gln Tyr
        835                 840                 845

Thr Tyr Lys Gln Glu Pro Ile Lys Lys Cys Thr Gly Arg Arg Pro Ala
    850                 855                 860

Ile Asn Tyr Pro Val Tyr Gly Glu Thr Thr Gln Val Arg Arg Arg Arg
865                 870                 875                 880
```

-continued

```
Phe Glu Arg Ala Ile Gly Pro Ser Gln Thr His Thr Ile Arg Ile His
                885                 890                 895

Tyr Ser Pro Ile Arg Val Ser Tyr Gln Asp Lys Gly Phe Leu His Asn
            900                 905                 910

Glu Val Lys Met Ser Ser Gln Trp Arg Gly Phe Pro Asn Val Val Thr
        915                 920                 925

Ser Ala Ile Ala Leu Pro Asn Ile Arg Lys Pro Asp Gly Tyr Asp Tyr
    930                 935                 940

Tyr Ala Phe Ser Arg Asn Gln Tyr Tyr Asn Ile Asp Val Pro Ser Arg
945                 950                 955                 960

Thr Ala Arg Val Val Thr Thr Arg Phe Gly Arg Thr Leu Ser Asn Ile
                965                 970                 975

Trp Tyr Asn Cys Pro
            980

<210> SEQ ID NO 8
<211> LENGTH: 23
<212> TYPE: DNA
<213> ORGANISM: Artificial Sequence
<220> FEATURE:
<223> OTHER INFORMATION: BGH-Forward Primer

<400> SEQUENCE: 8
tctagttgcc agccatctgt tgt                                              23

<210> SEQ ID NO 9
<211> LENGTH: 18
<212> TYPE: DNA
<213> ORGANISM: Artificial Sequence
<220> FEATURE:
<223> OTHER INFORMATION: BGH-Reverse Primer

<400> SEQUENCE: 9
tgggagtggc accttcca                                                    18

<210> SEQ ID NO 10
<211> LENGTH: 21
<212> TYPE: DNA
<213> ORGANISM: Artificial Sequence
<220> FEATURE:
<223> OTHER INFORMATION: BGH Probe

<400> SEQUENCE: 10
tcccccgtgc cttccttgac c                                                21

<210> SEQ ID NO 11
<211> LENGTH: 1404
<212> TYPE: PRT
<213> ORGANISM: Artificial Sequence
<220> FEATURE:
<223> OTHER INFORMATION: Human PRG4 transcript variant A amino acid
      sequence

<400> SEQUENCE: 11

Met Ala Trp Lys Thr Leu Pro Ile Tyr Leu Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45

Asn Cys Gln His Tyr Met Glu Cys Cys Pro Asp Phe Lys Arg Val Cys
    50                  55                  60
```

```
Thr Ala Glu Leu Ser Cys Lys Gly Arg Cys Phe Ser Phe Glu Arg
65                  70                  75                  80

Gly Arg Glu Cys Asp Cys Asp Ala Gln Cys Lys Lys Tyr Asp Lys Cys
            85                  90                  95

Cys Pro Asp Tyr Glu Ser Phe Cys Ala Glu Val His Asn Pro Thr Ser
                100                 105                 110

Pro Pro Ser Ser Lys Lys Ala Pro Pro Ser Gly Ala Ser Gln Thr
        115                 120                 125

Ile Lys Ser Thr Thr Lys Arg Ser Pro Lys Pro Asn Lys Lys Lys
        130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser
                165                 170                 175

Ser Thr Ile Arg Lys Ile Lys Ser Ser Lys Asn Ser Ala Ala Asn Arg
                180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
            245                 250                 255

Pro Ile Asn Pro Arg Pro Ser Leu Pro Pro Asn Ser Asp Thr Ser Lys
                260                 265                 270

Glu Thr Ser Leu Thr Val Asn Lys Glu Thr Thr Val Glu Thr Lys Glu
        275                 280                 285

Thr Thr Thr Thr Asn Lys Gln Thr Ser Thr Asp Gly Lys Glu Lys Thr
        290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
            340                 345                 350

Thr Thr Pro Lys Glu Pro Ala Ser Thr Thr Lys Glu Pro Thr Pro
            355                 360                 365

Thr Thr Ile Lys Ser Ala Pro Thr Thr Pro Lys Glu Pro Ala Pro Thr
        370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
            405                 410                 415

Thr Lys Glu Pro Ala Pro Thr Thr Lys Ser Ala Pro Thr Thr Pro
            420                 425                 430

Lys Glu Pro Ala Pro Thr Thr Pro Lys Lys Pro Ala Pro Thr Thr Pro
            435                 440                 445

Lys Glu Pro Ala Pro Thr Thr Pro Lys Glu Pro Thr Pro Thr Thr Pro
            450                 455                 460

Lys Glu Pro Ala Pro Thr Thr Lys Glu Pro Ala Pro Thr Thr Pro Lys
465                 470                 475                 480
```

```
Glu Pro Ala Pro Thr Ala Pro Lys Lys Pro Ala Pro Thr Thr Pro Lys
                485                 490                 495
Glu Pro Ala Pro Thr Thr Pro Lys Glu Pro Ala Pro Thr Thr Thr Lys
            500                 505                 510
Glu Pro Ser Pro Thr Thr Pro Lys Glu Pro Ala Pro Thr Thr Thr Lys
            515                 520                 525
Ser Ala Pro Thr Thr Thr Lys Glu Pro Ala Pro Thr Thr Lys Ser
            530                 535                 540
Ala Pro Thr Thr Pro Lys Glu Pro Ser Pro Thr Thr Lys Glu Pro
545                 550                 555                 560
Ala Pro Thr Thr Pro Lys Glu Pro Ala Pro Thr Thr Pro Lys Lys Pro
            565                 570                 575
Ala Pro Thr Thr Pro Lys Glu Pro Ala Pro Thr Thr Pro Lys Glu Pro
            580                 585                 590
Ala Pro Thr Thr Thr Lys Lys Pro Ala Pro Thr Thr Pro Lys Glu Pro
            595                 600                 605
Ala Pro Thr Thr Pro Lys Glu Thr Ala Pro Thr Thr Pro Lys Lys Leu
            610                 615                 620
Thr Pro Thr Thr Pro Glu Lys Leu Ala Pro Thr Thr Pro Glu Lys Pro
625                 630                 635                 640
Ala Pro Thr Thr Pro Glu Leu Ala Pro Thr Thr Pro Glu Glu Pro
            645                 650                 655
Thr Pro Thr Thr Pro Glu Glu Pro Ala Pro Thr Thr Pro Lys Ala Ala
            660                 665                 670
Ala Pro Asn Thr Pro Lys Glu Pro Ala Pro Thr Thr Pro Lys Glu Pro
            675                 680                 685
Ala Pro Thr Thr Pro Lys Glu Pro Ala Pro Thr Thr Pro Lys Glu Thr
            690                 695                 700
Ala Pro Thr Thr Pro Lys Gly Thr Ala Pro Thr Thr Leu Lys Glu Pro
705                 710                 715                 720
Ala Pro Thr Thr Pro Lys Lys Pro Ala Pro Lys Glu Leu Ala Pro Thr
                725                 730                 735
Thr Thr Lys Glu Pro Thr Ser Thr Thr Ser Asp Lys Pro Ala Pro Thr
            740                 745                 750
Thr Pro Lys Gly Thr Ala Pro Thr Thr Pro Lys Glu Pro Ala Pro Thr
            755                 760                 765
Thr Pro Lys Glu Pro Ala Pro Thr Thr Pro Lys Gly Thr Ala Pro Thr
            770                 775                 780
Thr Leu Lys Glu Pro Ala Pro Thr Thr Pro Lys Lys Pro Ala Pro Lys
785                 790                 795                 800
Glu Leu Ala Pro Thr Thr Thr Lys Gly Pro Thr Ser Thr Thr Ser Asp
                805                 810                 815
Lys Pro Ala Pro Thr Thr Pro Lys Glu Thr Ala Pro Thr Thr Pro Lys
            820                 825                 830
Glu Pro Ala Pro Thr Thr Pro Lys Lys Pro Ala Pro Thr Thr Pro Glu
            835                 840                 845
Thr Pro Pro Pro Thr Thr Ser Glu Val Ser Thr Pro Thr Thr Thr Lys
            850                 855                 860
Glu Pro Thr Thr Ile His Lys Ser Pro Asp Glu Ser Thr Pro Glu Leu
865                 870                 875                 880
Ser Ala Glu Pro Thr Pro Lys Ala Leu Glu Asn Ser Pro Lys Glu Pro
            885                 890                 895
Gly Val Pro Thr Thr Lys Thr Pro Ala Ala Thr Lys Pro Glu Met Thr
```

```
                 900             905             910
Thr Thr Ala Lys Asp Lys Thr Thr Glu Arg Asp Leu Arg Thr Thr Pro
        915             920             925

Glu Thr Thr Thr Ala Ala Pro Lys Met Thr Lys Glu Thr Ala Thr Thr
    930             935             940

Thr Glu Lys Thr Thr Glu Ser Lys Ile Thr Ala Thr Thr Gln Val
945             950             955             960

Thr Ser Thr Thr Thr Gln Asp Thr Thr Pro Phe Lys Ile Thr Thr Leu
            965             970             975

Lys Thr Thr Thr Leu Ala Pro Lys Val Thr Thr Lys Lys Thr Ile
        980             985             990

Thr Thr Thr Glu Ile Met Asn Lys Pro Glu Glu Thr Ala Lys Pro Lys
        995             1000            1005

Asp Arg Ala Thr Asn Ser Lys Ala Thr Thr Pro Lys Pro Gln Lys
    1010            1015            1020

Pro Thr Lys Ala Pro Lys Lys Pro Thr Ser Thr Lys Lys Pro Lys
    1025            1030            1035

Thr Met Pro Arg Val Arg Lys Pro Lys Thr Thr Pro Thr Pro Arg
    1040            1045            1050

Lys Met Thr Ser Thr Met Pro Glu Leu Asn Pro Thr Ser Arg Ile
    1055            1060            1065

Ala Glu Ala Met Leu Gln Thr Thr Thr Arg Pro Asn Gln Thr Pro
    1070            1075            1080

Asn Ser Lys Leu Val Glu Val Asn Pro Lys Ser Glu Asp Ala Gly
    1085            1090            1095

Gly Ala Glu Gly Glu Thr Pro His Met Leu Leu Arg Pro His Val
    1100            1105            1110

Phe Met Pro Glu Val Thr Pro Asp Met Asp Tyr Leu Pro Arg Val
    1115            1120            1125

Pro Asn Gln Gly Ile Ile Ile Asn Pro Met Leu Ser Asp Glu Thr
    1130            1135            1140

Asn Ile Cys Asn Gly Lys Pro Val Asp Gly Leu Thr Thr Leu Arg
    1145            1150            1155

Asn Gly Thr Leu Val Ala Phe Arg Gly His Tyr Phe Trp Met Leu
    1160            1165            1170

Ser Pro Phe Ser Pro Pro Ser Pro Ala Arg Arg Ile Thr Glu Val
    1175            1180            1185

Trp Gly Ile Pro Ser Pro Ile Asp Thr Val Phe Thr Arg Cys Asn
    1190            1195            1200

Cys Glu Gly Lys Thr Phe Phe Phe Lys Asp Ser Gln Tyr Trp Arg
    1205            1210            1215

Phe Thr Asn Asp Ile Lys Asp Ala Gly Tyr Pro Lys Pro Ile Phe
    1220            1225            1230

Lys Gly Phe Gly Gly Leu Thr Gly Gln Ile Val Ala Ala Leu Ser
    1235            1240            1245

Thr Ala Lys Tyr Lys Asn Trp Pro Glu Ser Val Tyr Phe Phe Lys
    1250            1255            1260

Arg Gly Gly Ser Ile Gln Gln Tyr Ile Tyr Lys Gln Glu Pro Val
    1265            1270            1275

Gln Lys Cys Pro Gly Arg Arg Pro Ala Leu Asn Tyr Pro Val Tyr
    1280            1285            1290

Gly Glu Thr Thr Gln Val Arg Arg Arg Arg Phe Glu Arg Ala Ile
    1295            1300            1305
```

```
Gly Pro Ser Gln Thr His Thr Ile Arg Ile Gln Tyr Ser Pro Ala
    1310                1315                1320

Arg Leu Ala Tyr Gln Asp Lys Gly Val Leu His Asn Glu Val Lys
    1325                1330                1335

Val Ser Ile Leu Trp Arg Gly Leu Pro Asn Val Val Thr Ser Ala
    1340                1345                1350

Ile Ser Leu Pro Asn Ile Arg Lys Pro Asp Gly Tyr Asp Tyr Tyr
    1355                1360                1365

Ala Phe Ser Lys Asp Gln Tyr Tyr Asn Ile Asp Val Pro Ser Arg
    1370                1375                1380

Thr Ala Arg Ala Ile Thr Thr Arg Ser Gly Gln Thr Leu Ser Lys
    1385                1390                1395

Val Trp Tyr Asn Cys Pro
    1400

<210> SEQ ID NO 12
<211> LENGTH: 5050
<212> TYPE: DNA
<213> ORGANISM: Artificial Sequence
<220> FEATURE:
<223> OTHER INFORMATION: Human PRG4 transcript variant A nucleic acid
      sequence

<400> SEQUENCE: 12
aaactcatct atcctttacg gcaagggtac ctacggtacc tgaaaacaac gatggcatgg      60
aaaacacttc ccatttacct gttgttgctg ctgtctgttt tcgtgattca gcaagtttca     120
tctcaagatt tatcaagctg tgcagggaga gtgggggaag ggtattctag atgccacc      180 tgcaactgtg attataactg tcaacactac atggagtgct gccctgattt caagagagtc     240
tgcactgcgg agctttcctg taaggccgc tgctttgagt ccttcgagag agggagggag      300
tgtgactgcg acgcccaatg taagaagtat gacaagtgct gtcccgatta tgagagtttc     360
tgtgcagaag tgcataatcc cacatcacca ccatcttcaa agaaagcacc tccaccttca     420
ggagcatctc aaaccatcaa atcaacaacc aaacgttcac ccaaaccacc aaacaagaag     480
aagactaaga aagttataga atcagaggaa ataacagaag aacattctgt ttctgaaaat     540
caagagtcct cctcctcctc ctcctcttcc tcttcttctt caacaattcg gaaaatcaag     600
tcttccaaaa attcagctgc taatagaaa ttacagaaga aactcaaagt aaaagataac      660
aagaagaaca gaactaaaaa gaaacctacc cccaaaccac cagttgtaga tgaagctgga     720
agtggattgg acaatggtga cttcaaggtc acaactcctg acacgtctac caccccaacac    780 aataaagtca gcacatctcc caagatcaca acagcaaaac caataaatcc cagacccagt     840
cttccaccta attctgatac atctaaagag acgtctttga cagtgaataa agagacaaca     900
gttgaaacta agaaactac tacaacaaat aaacagactt caactgatgg aaaagagaag      960
actacttccg ctaagagac acaaagtata gagaaaacat ctgctaaaga tttagcaccc    1020
acatctaaag tgctggctaa acctacaccc aaagctgaaa ctacaaccaa aggccctgct    1080
ctcaccactc ccaaggagcc cacgcccacc actcccaagg agcctgcatc taccacaccc    1140
aaagagccca cacctaccac catcaagtct gcacccacca ccccaaggga gcctgcaccc    1200
accaccacca gtctgcaccc accactcccc aaggagcctg cacccaccac accaaggag    1260 cctgcaccca ccactcccaa ggagcctgca cccaccacca caaggagcc tgcacccacc    1320 accaccaagt ctgcacccac cactcccaag gagcctgcac ccaccacccc caagaagcct    1380
```

```
gccccaacta cccccaagga gcctgcaccc accactccca aggagcctac acccaccact   1440
cccaaggagc ctgcacccac caccaaggag cctgcaccca ccactcccaa agagcctgca   1500
cccactgccc ccaagaagcc tgccccaact accccccaagg agcctgcacc caccactccc   1560
aaggagcctg cacccaccac caccaaggag ccttcaccca ccactcccaa ggagcctgca   1620
cccaccacca ccaagtctgc acccaccact accaaggagc ctgcacccac cactaccaag   1680 tctgcacccca ccactcccaa ggagccttca cccaccacca ccaaggagcc tgcacccacc   1740
actcccaagg agcctgcacc caccaccccc aagaagcctg ccccaactac ccccaaggag   1800
cctgcaccca ccactcccaa ggaacctgca cccaccacca ccaagaagcc tgcacccacc   1860
actcccaaag agcctgcccc aactaccccc aaggagactg cacccaccac ccccaagaag   1920
ctcacgccca cccccccga gaagctcgca cccaccaccc ctgagaagcc cgcacccacc   1980 accccctgagg agctcgcacc caccacccct gaggagccca cacccaccac ccctgaggag   2040
cctgctccca ccactcccaa ggcagcggct cccaacaccc ctaaggagcc tgctccaact   2100
acccctaagg agcctgctcc aactaccccct aaggagcctg ctccaactac ccctaaggag   2160
actgctccaa ctacccctaa agggactgct ccaactaccc tcaaggaacc tgcacccact   2220
actcccaaga gcctgccccc caaggagctt gcacccacca ccaccaagga gcccacatcc   2280
accacctctg acaagcccgc tccaactacc cctaagggga ctgctccaac taccccctaag   2340 gagcctgctc caactacccc taaggagcct gctccaacta ccccctaaggg gactgctcca   2400 actaccctca aggaacctgc acccactact cccaagaagc ctgccccaa ggagcttgca   2460 cccaccacca caaggggcc cacatccacc acctctgaca gcctgctcc aactacacct   2520 aaggagactg ctccaactac ccccaaggag cctgcaccca ctaccccccaa gaagcctgct   2580 ccaactactc ctgagacacc tcctccaacc acttcagagg tctctactcc aactaccacc   2640
aaggagccta ccactatcca caaaagccct gatgaatcaa ctcctgagct ttctgcagaa   2700
cccacaccaa aagctcttga aaacagtccc aaggaacctg gtgtacctac aactaagact   2760
cctgcagcga ctaaacctga aatgactaca acagctaaag acaagacaac agaaagagac   2820
ttacgtacta cacctgaaac tacaactgct gcacctaaga tgacaaaaga dacagcaact   2880
acaacagaaa aaactaccga atccaaaata acagctacaa ccacacaagt aacatctacc   2940
acaactcaag ataccacacc attcaaaatt actactctta aaacaactac tcttgcaccc   3000
aaagtaacta caacaaaaaa gacaattact accactgaga ttatgaacaa acctgaagaa   3060
acagctaaac caaaagacag agctactaat tctaaagcga caactcctaa accctcaaaag   3120 ccaaccaaag caccccaaaa acccacttct accaaaaagc caaaaacaat gcctagagtg   3180
agaaaaccaa agacgacacc aactccccgc aagatgacat caacaatgcc agaattgaac   3240
cctacctcaa gaatagcaga agccatgctc caaaccacca ccagacctaa ccaaactcca   3300
aactccaaac tagttgaagt aaatccaaag agtgaagatg caggtggtgc tgaaggagaa   3360
acacctcata tgcttctcag gccccatgtg ttcatgcctg aagttactcc cgacatggat   3420
tacttaccga gagtacccaa tcaaggcatt atcatcaatc ccatgctttc cgatgagacc   3480
aatatatgca atggtaagcc agtagatgga ctgactactt tgcgcaatgg gacattagtt   3540
gcattccgag gtcattattt ctggatgcta agtccattca gtccaccatc tccagctcgc   3600
agaattactg aagtttgggg tattccttcc cccattgata ctgttttac taggtgcaac   3660 tgtgaaggaa aaactttctt ctttaaggat tctcagtact ggcgttttac caatgatata   3720
aaagatgcag ggtaccccaa accaattttc aaaggatttg gaggactaac tggacaaata   3780
```

```
gtggcagcgc tttcaacagc taaatataag aactggcctg aatctgtgta ttttttcaag    3840
agaggtggca gcattcagca gtatatttat aaacaggaac ctgtacagaa gtgccctgga    3900
agaaggcctg ctctaaatta tccagtgtat ggagaaacga cacaggttag gagacgtcgc    3960
tttgaacgtg ctataggacc ttctcaaaca cacaccatca gaattcaata ttcacctgcc    4020
agactggctt atcaagacaa aggtgtcctt cataatgaag ttaaagtgag tatactgtgg    4080
agaggacttc caaatgtggt tacctcagct atatcactgc ccaacatcag aaaacctgac    4140
ggctatgatt actatgcctt ttctaaagat caatactata acattgatgt gcctagtaga    4200
acagcaagag caattactac tcgttctggg cagaccttat ccaaagtctg gtacaactgt    4260
ccttagactg atgagcaaag gaggagtcaa ctaatgaaga aatgaataat aaattttgac    4320
actgaaaaac attttattaa taaagaatat tgacatgagt ataccagttt atatataaaa    4380
atgtttttaa acttgacaat cattacacta aaacagattt gataatctta ttcacagttg    4440
ttattgttta cagaccattt aattaatatt tcctctgttt attcctcctc tccctcccat    4500
tgcatggctc acacctgtaa aagaaaaaag aatcaaattg aatatatctt ttaagaattc    4560
aaaactagtg tattcactta ccctagttca ttataaaaaa tatctaggca ttgtggatat    4620
aaaactgttg ggtattctac aacttcaatg gaaattatta caagcagatt aatccctctt    4680
tttgtgacac aagtacaatc taaaagttat attggaaaac atggaaatat taaaatttta    4740
cacttttact agctaaaaca taatcacaaa gctttatcgt gttgtataaa aaaattaaca    4800
atataatggc aataggtaga gatacaacaa atgaatataa cactataaca cttcatattt    4860
tccaaatctt aatttggatt taaggaagaa atcaataaat ataaatata agcacatatt    4920 tattatatat ctaaggtata caaatctgtc tacatgaagt ttacagattg gtaaatatca    4980
cctgctcaac atgtaattat ttaataaaac tttggaacat taaaaaaata aattggaggc    5040
ttaaggatta                                                          5050
```